(12) United States Patent
Hryhorenko et al.

(10) Patent No.: US 10,379,105 B2
(45) Date of Patent: *Aug. 13, 2019

(54) ANTIBODIES TO ARIPIPRAZOLE HAPTENS AND USE THEREOF

(71) Applicant: Janssen Pharmaceutica NV, Beerse (BE)

(72) Inventors: Eric Hryhorenko, Hilton, NY (US); Banumathi Sankaran, Lexington, MA (US); Thomas R. DeCory, Pittsford, NY (US); Theresa Tubbs, Rochester, NY (US); Linda Colt, Rochester, NY (US); Bart M. Remmerie, Ghent (BE); Rhys Salter, Doylestown, PA (US); Ronghui Lin, Ambler, PA (US)

(73) Assignee: Janssen Pharmaceutica NV, Beerse (BE)

( * ) Notice: Subject to any disclaimer, the term of this patent is extended or adjusted under 35 U.S.C. 154(b) by 148 days.

This patent is subject to a terminal disclaimer.

(21) Appl. No.: 15/474,881

(22) Filed: Mar. 30, 2017

(65) Prior Publication Data
US 2017/0204198 A1   Jul. 20, 2017

Related U.S. Application Data

(62) Division of application No. 13/971,429, filed on Aug. 20, 2013, now Pat. No. 9,611,332.

(60) Provisional application No. 61/691,544, filed on Aug. 21, 2012.

(51) Int. Cl.
| *C07K 14/44* | (2006.01) |
| *G01N 33/94* | (2006.01) |
| *G01N 33/50* | (2006.01) |
| *C07K 16/44* | (2006.01) |
| *C07D 215/227* | (2006.01) |

(52) U.S. Cl.
CPC ..... *G01N 33/5008* (2013.01); *C07D 215/227* (2013.01); *C07K 16/44* (2013.01); *G01N 33/5005* (2013.01); *G01N 33/94* (2013.01); *C07K 2317/14* (2013.01); *G01N 2800/302* (2013.01); *G01N 2800/52* (2013.01)

(58) Field of Classification Search
CPC .... C07K 16/44; C07K 2317/14; G01N 33/94; G01N 33/5008; G01N 33/5005; G01N 2800/52; G01N 2800/302; C07D 215/227
See application file for complete search history.

(56) References Cited

U.S. PATENT DOCUMENTS

| 4,166,452 A | 9/1979 | Generales, Jr. |
| 5,120,643 A | 6/1992 | Ching et al. |
| 5,527,709 A | 6/1996 | Danielson et al. |
| 5,559,041 A | 9/1996 | Kang et al. |
| 5,587,458 A | 12/1996 | King et al. |
| 5,641,870 A | 6/1997 | Rinderknecht et al. |
| 5,714,389 A | 2/1998 | Charlton et al. |
| 5,761,894 A | 6/1998 | Evans et al. |
| 6,034,078 A | 3/2000 | Fairburst J et al. |
| 6,139,800 A | 10/2000 | Chandler |
| 6,228,660 B1 | 5/2001 | May et al. |
| 7,163,681 B2 | 1/2007 | Giles-Komar et al. |
| 7,416,700 B2 | 8/2008 | Buechler et al. |
| 7,772,240 B2 | 8/2010 | Bang-Andersen et al. |
| 7,901,949 B2 | 3/2011 | Raj |
| 8,058,405 B2 | 11/2011 | Demuth et al. |
| 8,088,594 B2 | 1/2012 | Salamone et al. |
| 9,012,648 B2 | 4/2015 | Haspeslagh et al. |
| 9,303,041 B2 | 4/2016 | Donahue et al. |
| 9,304,126 B2 | 4/2016 | Donahue et al. |
| 9,394,354 B2 | 7/2016 | Haspeslagh et al. |
| 9,410,972 B2 | 8/2016 | Hryhorenko et al. |
| 9,434,693 B2 | 9/2016 | Wall et al. |
| 9,453,002 B2 | 9/2016 | Ahmad et al. |
| 9,465,041 B2 | 10/2016 | Hryhorenko et al. |
| 9,494,607 B2 | 11/2016 | Hryhorenko et al. |
| 9,494,608 B2 | 11/2016 | Hryhorenko et al. |
| 9,504,682 B2 | 11/2016 | Lin et al. |
| 9,611,332 B2 | 4/2017 | Hryhorenko et al. |
| 9,664,700 B2 | 5/2017 | Hryhorenko et al. |
| 9,751,953 B2 | 9/2017 | Hryhorenko et al. |
| 9,795,685 B2 * | 10/2017 | Lin ..................... A61K 31/496 |
| 9,850,318 B2 | 12/2017 | Hryhorenko et al. |
| 2003/0087306 A1 | 5/2003 | Christensen et al. |
| 2003/0143233 A1 | 7/2003 | Goshorn et al. |
| 2003/0202975 A1 | 10/2003 | Tedder |
| 2004/0127489 A1 | 7/2004 | Pickar et al. |
| 2005/0163708 A1 | 7/2005 | Robinson et al. |
| 2006/0046967 A1 | 3/2006 | Satyam |
| 2006/0235005 A1 | 10/2006 | Goff |
| 2006/0251592 A1 | 11/2006 | Hendler et al. |
| 2006/0289787 A1 | 12/2006 | Ohman et al. |

(Continued)

FOREIGN PATENT DOCUMENTS

| CN | 101821244 | 9/2010 |
| CN | 102260290 A | 11/2011 |

(Continued)

OTHER PUBLICATIONS

Abdel-Baki, A., et al., "Pharmacotherapy Challenges in Patients with First-Episode Psychosis", Journal of Affective Disorders, vol. 138, pp. S3-S14 (2012).

(Continued)

*Primary Examiner* — Shafiqul Haq

(57) ABSTRACT

Disclosed is an antibody which binds to aripiprazole, which can be used to detect aripiprazole in a sample such as in a competitive immunoassay method. The antibody can be used in a lateral flow assay device for point-of-care detection of aripiprazole, including multiplex detection of aripiprazole, olanzapine, quetiapine, and risperidone in a single lateral flow assay device.

8 Claims, 20 Drawing Sheets

(56) References Cited

U.S. PATENT DOCUMENTS

| | | |
|---|---|---|
| 2007/0015290 A1 | 1/2007 | Raj |
| 2007/0231883 A1 | 10/2007 | Lindstrom et al. |
| 2008/0187529 A1 | 8/2008 | Shitara et al. |
| 2008/0260812 A1 | 10/2008 | Matsuyama et al. |
| 2009/0325193 A1 | 12/2009 | Grenier et al. |
| 2010/0069356 A1 | 3/2010 | Grant et al. |
| 2010/0144781 A1 | 6/2010 | Fu et al. |
| 2010/0203129 A1 | 8/2010 | Andersen et al. |
| 2010/0266502 A1 | 10/2010 | Kimura |
| 2011/0230520 A1 | 9/2011 | Sartor et al. |
| 2011/0245224 A1 | 10/2011 | Barvian et al. |
| 2012/0004165 A1 | 1/2012 | Keil et al. |
| 2012/0071636 A1 | 3/2012 | Salamone et al. |
| 2014/0057297 A1 | 2/2014 | Hryhorenko et al. |
| 2014/0057298 A1 | 2/2014 | Hryhorenko et al. |
| 2014/0057300 A1 | 2/2014 | Hryhorenko et al. |
| 2014/0057301 A1 | 2/2014 | Hryhorenko et al. |
| 2014/0057302 A1 | 2/2014 | Hryhorenko et al. |
| 2014/0057303 A1 | 2/2014 | Hryhorenko et al. |
| 2014/0057304 A1 | 2/2014 | Hryhorenko et al. |
| 2014/0057305 A1 | 2/2014 | Hryhorenko et al. |
| 2014/0057306 A1 | 2/2014 | Hryhorenko et al. |
| 2014/0155585 A1 | 6/2014 | Haspeslagh et al. |
| 2014/0162997 A1 | 6/2014 | Wall et al. |
| 2014/0163206 A1 | 6/2014 | Lin et al. |
| 2014/0213766 A1 | 7/2014 | Donahue et al. |
| 2014/0213767 A1 | 7/2014 | Haspeslagh et al. |
| 2014/0221616 A1 | 8/2014 | Donahue et al. |
| 2015/0051225 A1 | 2/2015 | Ahmad et al. |
| 2018/0117169 A1* | 5/2018 | Lin ................ A61K 31/496 |
| 2018/0149637 A1* | 5/2018 | Hryhorenko ........... C07K 16/44 |

FOREIGN PATENT DOCUMENTS

| | | |
|---|---|---|
| EP | 0582368 B1 | 1/2001 |
| EP | 0583820 A1 | 3/2002 |
| EP | 2316468 A1 | 5/2011 |
| EP | 2343296 A1 | 7/2011 |
| JP | A-06-94712 | 4/1994 |
| JP | A-H07-247271 | 9/1995 |
| JP | A-2003-516423 | 5/2003 |
| JP | 2006-502698 | 1/2006 |
| JP | 2010-533291 | 10/2010 |
| WO | WO 1995/34652 | 12/1995 |
| WO | WO 2001/042787 A2 | 6/2001 |
| WO | WO 2003/074566 A2 | 9/2003 |
| WO | WO 2003/082877 | 10/2003 |
| WO | WO 2003/103835 | 12/2003 |
| WO | WO 2004/014895 | 2/2004 |
| WO | WO 2005/000901 | 1/2005 |
| WO | WO 2005/028458 | 3/2005 |
| WO | WO 2005/033073 | 4/2005 |
| WO | WO 2005/089082 | 9/2005 |
| WO | WO 2005/118139 | 12/2005 |
| WO | WO 2006/137785 | 12/2006 |
| WO | WO-2007/035348 A2 | 3/2007 |
| WO | WO 2009/040409 | 4/2009 |
| WO | WO 2010/015029 | 2/2010 |
| WO | WO 2010/104749 | 9/2010 |
| WO | WO-2010/151711 A1 | 12/2010 |
| WO | WO-2011/012715 A1 | 2/2011 |
| WO | WO 2011/022089 A1 | 2/2011 |
| WO | WO-2011/042450 A1 | 4/2011 |
| WO | WO 2011/082076 | 7/2011 |
| WO | WO 2011/112657 | 9/2011 |
| WO | WO 2011/115733 | 9/2011 |
| WO | WO 2011/163594 A2 | 11/2011 |
| WO | WO 2011/159537 | 12/2011 |
| WO | WO 2012/003418 | 1/2012 |
| WO | WO 2012/012595 | 1/2012 |
| WO | WO-2013/024047 A1 | 2/2013 |
| WO | WO-2013/024048 A1 | 2/2013 |
| WO | WO 2013/088255 | 6/2013 |

OTHER PUBLICATIONS

Aliouane, L., et al., "Synthesis of Difluoromethylphosphonamidates by Directed Addition of Amine", Tetrahedron Letters, vol. 52, pp. 3681-3685 (2011).

Annuziato, M., et al., "p-Maleimidophenyl Isocyanate: A Novel Heterobifunctional Linker for Hydroxyl to Thiol Coupling", Bioconjugate Chemistry, vol. 4, pp. 212-218 (1993).

Billah, MD., et al. "Directed Immobilization of Reduced Antibody Fragments onto a Novel SAM on Gold for Myoglobin Impedance Immunosensing", Bioelectrochemistry, vol. 80, pp. 49-54 (2010).

Bodin, A., et al., "Identification and Allergenic Activity of Hydroxyaldehydes—A New Type of Oxidation Product from an Ethylated Non-Ionic Surfactant", Contact Dermatitis, vol. 44, pp. 207-212 (2001).

Brinkley, Michael, "A Brief Survey of Methods for Preparing Protein Conjugates with Dyes, Haptens, and Cross-Linking Reagents", Bioconjugate Chemistry, vol. 3, pp. 2-13 (1992).

Carter, P., et al., "High Level *Escherichia coli* Expression and Production of a Bivalent Humanized Antibody Fragment", Biotechnology, vol. 10, pp. 163-167.

Chamow, S., et al., "Conjugation of Soluble CD4 without Loss of Biological Activity via a Novel Carbohydrate-Directed Cross-Linking Reagent", The Journal of Biological Chemistry, vol. 267, No. 22, Issue of Aug. 5, pp. 15916-15922 (1992).

Chappey, O., et al., "Monoclonal Antibodies in Hapten Immunossays", Pharmaceutical Research, vol. 9, No. 11, pp. 1375-1379 (1992).

Cleland, W. W., "Dithiothreitol, a New Protective Reagent for SH Groups", Biochemistry, vol. 3, No. 4, pp. 480-482 (1964).

Dai, R., et al., "A High-Throughput Assay for Evaluating State Dependence and Subtype Selectivity of Cav2 Calcium Channel Inhibitors", ASSAY and Drug Development Technologies, vol. 6, No. 2, pp. 195-212 (2008).

Danilova, N., et al., "Production and Characterization of Anti-Theophylline Monoclonal Antibodies Suitable for Immunoassay", Immunology Letters, vol. 29, pp. 79-84 (1991).

Davis, P., et al., "Development and Validation of an LC-MS/MS Method for the Determination of Quetiapine and Four Related Metabolites in Human Plasma", Journal of Pharmaceutical and Biomedical Analysis, vol. 51, pp. 1113-1119 (2010).

Diago-Meseguer, J., et al., "A New Reagent for Activating Carboxyl Groups, Preparation and Reactions of N,N-Bis[2-oxo-3-oxazolidinyl)phosphorodiamidic Chloride", Syntheses, vol. 7(1), pp. 547-551 (1980).

Dixon, W.J., "Efficient Analysis of Experimental Observations", Ann. Rev. Pharmacol. Toxicol., vol. 20, pp. 441-462 (1980).

European Search Report dated Jul. 18, 2016, in EP Patent Application No. 13830412.6.

Fiedler, H., et al., "Surface Chemical Characterization of Maleic Acid Mono[2-4-alkylpiperazinyl)ethyl esters]. 1. The Complex Adsorption Behavior of an Ampholytic Surfactant", Langmuir, vol. 10 pp. 3959-3965 (1994).

Finley, F., et al., "An Integrated Multiassay Approach to the Discovery of Small-Molecule N-Type Voltage-Gated Calcium Channel Antagonists", ASSAY and Drug Development Technologies, vol. 8, No. 6, pp. 685-694 (2010).

Gentaur Molecular Products, Data Sheet, Enzyme Immunoassay for the Detection of Olanzapine in Urine or Serum, p. 2 (May 2012).

Ghetie, V., et al., "Preparation and Characterization of Conjugates of Recombinant CD4 and Deglycosylated Ricin A Chain Using Different Cross-Linkers", Bioconjugate Chemistry, vol. 1, pp. 24-31 (1990).

Goodrow et al., "Strategies for immunoassay hapten design," Immunoanalysis of Agrochemicals 1995, ACS symposium Series, Chapter 9, vol. 586, pp. 119-139.

Gorja, D., et al., "Novel N-Indolylmethyl Substituted Olanzapine Derivatives: Their Design, Synthesis and Evaluation as PDE4B Inhibitors+", Organic & Bimolecular Chemistry, vol. 11, pp. 2075-2079 (2013).

(56) References Cited

OTHER PUBLICATIONS

Heykants, J., et al., "The Pharmacokinetics of Risperidone in Humans: A Summary", J. Clinical Psychiatry, vol. 55(5), pp. 13-17 (1994).
Holliger, P. et al. "Specific killing of lymphoma cells by cytotoxic T-cells mediated by a bispecific diabody," Protein Engineering, 1996; 9(3): 299-305.
Hermanson, G.T., Bioconjugate Techniques, Zero-Length Cross-Linkers, 1996; 169-186.
Hermanson, G.T., Bioconjugate Techniques, Preparation of Hapten-Carrier Immunogen Conjugates, 1996; 419-455.
Huang, M-L, et al., "Pharmacokinetics of the Novel Antipsychotic Agent Risperidone and the Prolactin Response in Healthy Subjects", Clinical Pharmacology Therapeutics, vol. 54, pp. 257-268 (1993).
Huse, W., et al., "Generation of a Large Combinatorial Library of the Immunoglobulin Repertoire in Phage Lambda":, Research Article, pp. 1275-1281 (Dec. 1989).
International Search Report for Application No. PCT/US2013/055700 dated Oct. 10, 2013.
International Search Report for Application No. PCT/US2013/055712 dated Dec. 13, 2013.
International Search Report for Application No. PCT/US2013/055724 dated Sep. 24, 2013.
International Search Report for corresponding Application No. PCT/US2013/055729 dated Oct. 31, 2013.
International Search Report dated Jan. 16, 2014 for Application No. PCT/US2013/55733.
International Search Report dated Mar. 13, 2014 for Application No. PCT/US2013/55775.
International Search Report dated Jan. 16, 2014 for Application No. PCT/US2013/55780.
International Search Report dated Mar. 10, 2014 for Application No. PCT/US2013/55787.
International Search Report dated Jan. 16, 2014 for Application No. PCT/US2013/55794.
International Search Report dated Mar. 10, 2014 for Application No. PCT/US2013/55803.
International Search Report dated Jan. 30, 3014 for Application No. PCT/US2013/55817.
International Search Report dated Mar. 3, 2014 for Application No. PCT/US2013/55826.
International Search Report dated Jan. 16, 2014 for Application No. PCT/US2013/55830.
International Search Report dated Mar. 4, 2014 for Application No. PCT/US2013/55834.
International Search Report dated Oct. 31, 2013 for Application No. PCT/US2013/055282.
International Search Report dated Oct. 11, 2013 for Application No. PCT/US2013/055263.
International Search Report dated Feb. 27, 2014 for Application No. PCT/US2013/055694.
Kim, S., et al., "An Experimental Model for Peripheral Neuropahty Produced by Segmental Spinal Nerve Ligation in the Rat", Pain, vol. 50, pp. 355-363 (1992).
Kirley, Terence L., Reduction and Fluorescent Labeling of Cyst€ine-Containing Proteins for Subsequent Structural Analyses, Analytical Biochemistry, vol. 180, pp. 231-236 (1989).
Kirschbaum et al., "Therapeutic monitoring of Aripiprazole by HPLC with column-switching and spectrometric detection," Clinical Chemistry, 2005; 51( 9):1718-1721.
Kitagawa, T. et al., "Preparation and Characterization of Heterobifunctional Cross-linking Reagents for Protein Modifications," Chem. Pharm. Bull., 1981; 29 (4): 1130-1135.
Kohler, C., et al., "Continuous Cultures of Fused Cells Secreting Antibody of Predefined Specificity", Nature, vol. 256, Aug. 7, 1975 pp. 495-497.

Konig, W., et al., "A New Method for Synthesizing Peptides: Activation of Carboxyl Molecules With Dicyclohexylcarbodiimide by Adding 1-Hydroxybenzopartriazles", Chem. Ber. vol. 103, pp. 788-798 (1970).
Kubo, M., et al., "Development and Validation of an LC-MS/MS method for the quantitative determination of aripiprazole and its main metabolite, OPC-14857, in human plasma," J Chromatogoraphy B, 2005, vol. 822, No. 1-2, pp. 294-299.
Li, Z., et al., "Synthesis and Characteristization of N-Benzoyl-N'-Carboxyalkyl Substituted Thiourea Derivatives", Phosphorus, Sulfur and Silicon, vol. 178, pp. 293-297 (2003).
Lieberman, J., et al., "Effectiveness of Antipsychotic Drugs in Patients with Chronic Schizophrenia", The New England Journal of Medicine, vol. 353, pp. 1209-1223 (2005).
Liu, H., et al., "Organophosphorus Compound DEPBT as a Coupling Reagent for Oligopeptides and Peptoids Synthesis: Studies on Its Mechanism", Chinese Chemical Letters, vol. 13, No. 7, pp. 601-604 (2002).
Maddox, D., et al., "Elevated Serum Levels in Human Pregnancy of a Molecule Immunochemically Similar to Eospiophil Granule major Basic Protein", J. Exp. Medicine, vol. 158, pp. 1211-1226 (1983).
Malachowski, W., et al. The Chemistry of Phosphapeptides: Formation of Functionalized Phosphonochloridates Under Mild Conditions and Their Reaction With Alcohols and Amines, Journal of Organic Chemistry, vol. 59, pp. 7616-7624 (1994).
Modena, D., et al, Production and Characterization of Murne Monoclonal Antibodies to Polypeptide Hormones and Their Fragments, Annali Dell'Istitto Superiore di Sanita, vol. 27, No. 1, pp. 167-174 (1991).
Needleman, S., et al., "A General Method Applicable to the Search for Similarities in the Amino Acid Sequence of Two Proteins", J. Molecular Biology, vol. 48, pp. 443-453 (1970).
Nielsen, C., et al., "Anti-Allodynic Efficacy of the $_\chi$-Conopeptide, Xen2174, in Rats with Neuropathic Pain", Pain, vol. 118, p. 112-124 (2005).
Nolli, M., et al., "Antibodies Against the Antibiotics: An Overview", Annali, Istituto Superiore di Sanita, vol. 27, No. 1, pp. 149-154 (1991).
Park, J., et al., "Novel Cyanine Dyes with Vinylsulfone Group for Labeling Biomolecules", Bioconjugate Chemistry, pp. 350-362 (2012).
Penning, T., et al., "Synthesis of Potent Leukotriene $A_4$ Hydrolase Inhibitors. Identification of 3-[Methyl]4-(phenhlmethyl)phenooxy]propyl]amino]propanoic Acid", J. Medical Chemistry, vol. 45, pp. 3482-3490 (2002).
Posthuma-Trumpie et al., "Lateral flow (immuno)assay: its strength, weakness, oppertunities and threats. A literature survey," Anal Bioanal Chem, 2009; 393:569-582.
Pruhs, S., et al., "Upscaling the Solid-Phase Synthesis of a Tetrahydrocarabazole in Chemical Development" Organic Process Research & Development, vol. 10, pp. 441-445 (2006).
Rich, D. et al. "Analogues of the Cytostatic Cyclic Tetrapeptide Chlamydocin. Synthesis of Nβ-(N-Maleoylglycyl) and Nβ-(tert-Butyloxycarbonyl) Derivatives of cyclo (Gly-L-Phe-D-Pro-L-Dap)," Journal of Medicinal Chemistry, 1981; 24(5): 567-572.
Schmid, K., et al., "Distribution of Cyclopropenoid Fatty Acids in Malvaceous Plant Parts", Phytochemistry, vol. 27, No. 9,pp. 2831-2834 (1988).
Smith, T., et al., "Comparison of Biosequences", Advances in Applied Mathematics, vol. 2, pp. 482-489 (1981).
Su, J., et al., "Modification of the Clozapine structure by Parallel Synthesis", Bioorganic & Medicinal Chemistry Letters, vol. 16, p. 4548-4553 (2006).
Subasinghe, N., et al., "A Novel Series of Pyrazolylpiperidine N-Type Calcium Channel Blockers", Bioorganic & Medicinal Chemistry Letters, vol. 22, pp. 4080-4083 (2012).
Urban, J., Aripiprazole has 1-15 Functionally Selective Actions at Dopamine D2 Receptor-Mediated Signaling Pathways, Neuropsychopharmacology, 2006; 32(1):67-77.
Van Os, J., et al., "Schizophrenia", Lancet, vol. 374, pp. 635-645 (2009).

(56) References Cited

OTHER PUBLICATIONS

Wang Hongyun et al., "LC-MS/MS determination of aripiprazole and dehydroaripiprazole in human plasma," Chinese Journal of Pharmaceutical Analysis, 2011; 3(7):1278-1282.

Westermann et al., "Simple, rapid and sensitive determination of epinephrine and norepinephrine in unire and plasma by non-competitive enzyme immunoassay, compared with HPLC method," Clin. Lab., 2002; 48:61-71.

Wilbur, D., et al., Reagents for Astatination of Biomolecules; Comparison of the In Vivo Distribution and Stability of Some Radioiodinated/Astatinated Benzamidyl and nido-Carboranyl Compounds, Bioconjugate Chemistry, vol. 15, pp. 203-223 (2004).

Woestenborghs, R., et al, "On the Selectivity of Some Recently Developed RIA's", Methodological Surveys in Biochemistry and Analysis. vol. 20, pp. 241-246 (1990).

Wu, X., et al. "A New Homobifunctional p-Nitro Phenyl Ester XCoupling Reagent for the Preparation of Neoglycoproteins", Organic Letters, vol. 6, No. 24, pp. 4407-4410 (2004).

Alphs et al., "Onset of efficacy with acute long-acting injectable paliperidone palmitate treatment in markedly to severely ill patients with schizophrenia: post hoc analysis of a randomized, double-blind clinical trial," Annals of General Psychiatry, 2011, 10(12): 1-10.

Huang, H-C, et al., Detection and Quantification of Aripiprazole and its Metabolite, Dehydroaripiprazole, by Gas Chromatography-Mass Spectrometry in Blood Samples of Psychiatric Patients, J. Chromatogr. B, 2007; 856:57-61.

Mitchell, PB., Therapeutic Drug Monitoring of Psychotropic Medications, Br. J. Clin. Pharmacol., 2000; 49(4) ;303-312.

Tsai, C-J et al., The Quantitative Detection of Aripiprazole and its Main Metabolite by using Capillary-Electrophoresis, J. Chin. Med. Assoc., 2011; 74:267-271.

\* cited by examiner

ANTIBODIES TO ARIPIPRAZOLE HAPTENS AND USE THEREOF

CROSS-REFERENCE TO RELATED APPLICATIONS

This application is a divisional application of U.S. patent application Ser. No. 13/971,429, filed Aug. 20, 2013, published Feb. 27, 2014, as US2014/0057299, which claims the benefit of U.S. Provisional Patent Application No. 61/691,544, filed Aug. 21, 2012, the contents of both of which are incorporated by reference in their entireties.

FIELD OF THE INVENTION

The present invention relates to the field of immunoassays, and in particular to antibodies that bind to aripiprazole which can be used in immunoassays for detection of aripiprazole.

BACKGROUND

Schizophrenia is a chronic and debilitating psychiatric disorder affecting approximately 0.45-1% of the world's population (van Os, J.; Kapur, S. "Schizophrenia" *Lancet* 2009, 374, 635-645). The principal goals of treatment are to achieve sustained remission from psychotic symptoms, reduce the risk and consequences of relapse, and improve patient functioning and overall quality of life. While many patients with schizophrenia are able to achieve symptom stability with the available antipsychotic medications, poor adherence to medication is a common reason for relapse with daily administered oral medications. Several studies (Abdel-Baki, A.; Ouellet-Plamondon, C.; Malla, A. "Pharmacotherapy Challenges in Patients with First-Episode Psychosis" *Journal of Affective Disorders* 2012, 138, S3-S14) investigating the outcomes of non-compliance have shown that patients with schizophrenia who do not take their medication as prescribed have higher rates of relapse, hospital admission and suicide as well as increased mortality. It is estimated that 40 to 75% of patients with schizophrenia have difficulty adhering to a daily oral treatment regimen (Lieberman, J. A.; Stroup, T. S.; McEvoy, J. P.; Swartz, M. S.; Rosenheck, R. A.; Perkins, D. O.; Keefe, R. S. E.; Davis, S. M.; Davis, C. E.; Lebowitz, B. D.; Severe, J.; Hsiao, J. K. "Effectiveness of Antipyschotic Drugs in Patients with Chronic Schizophrenia" *New England Journal of Medicine* 2005, 353(12), 1209-1223).

Therapeutic drug monitoring (TDM) is the quantification of serum or plasma concentrations of drugs, including anti-psychotic drugs, for treatment monitoring and optimization. Such monitoring permits, for example, the identification of patients that are not adhering to their medication regimen, that are not achieving therapeutic doses, that are non-responsive at therapeutic doses, that have suboptimal tolerability, that have pharmacokinetic drug-drug interactions, or that have abnormal metabolism resulting in inappropriate plasma concentrations. Considerable individual variability exists in the patient's ability to absorb, distribute, metabolize, and excrete anti-psychotic drugs. Such differences can be caused by concurrent disease, age, concomitant medication or genetic peculiarities. Different drug formulations can also influence the metabolism of anti-psychotic drugs. TDM permits dose optimization for individual patients, improving therapeutic and functional outcomes. TDM further permits a prescribing clinician to ensure compliance with prescribed dosages and achievement of effective serum concentrations.

To date, methods for determining the levels of serum or plasma concentrations of anti-psychotic drugs involve the use of liquid chromatography (LC) with UV or mass spectrometry detection, and radioimmunoassays (see, for example, Woestenborghs et al., 1990 "On the selectivity of some recently developed RIA's" in Methodological Surveys in Biochemistry and Analysis 20:241-246. Analysis of Drugs and Metabolites, Including Anti-infective Agents; Heykants et al., 1994 "The Pharmacokinetics of Risperidone in Humans: A Summary", J Clin Psychiatry 55/5, suppl:13-17; Huang et al., 1993 "Pharmacokinetics of the novel anti-psychotic agent risperidone and the prolactin response in healthy subjects", Clin Pharmacol Ther 54:257-268). Radioimmunoassays detect one or both of risperidone and paliperidone. Salamone et al. in U.S. Pat. No. 8,088,594 disclose a competitive immunoassay for risperidone using antibodies that detect both risperidone and paliperidone but not pharmacologically inactive metabolites. The antibodies used in the competitive immunoassay are developed against a particular immunogen. ID Labs Inc. (London, Ontario, Canada) markets an ELISA for olanzapine, another anti-psychotic drug, which also utilizes a competitive format. The Instructions For Use indicate that the assay is designed for screening purposes and intended for forensic or research use, and is specifically not intended for therapeutic use. The Instructions recommend that all positive samples should be confirmed with gas chromatography/mass spectrometry (GC-MS), and indicate that the antibody used detects olanzapine and clozapine (see ID Labs Inc., "Instructions For Use Data Sheet IDEL-F083", Rev. Date Aug. 8, 2011). Some of these methods, namely HPLC and GC/MS, can be expensive and labor-intensive, and are generally only performed in large or specialty labs having the appropriate equipment.

A need exists for other methods for determining the levels of anti-psychotic drugs, particularly methods that can be performed in a prescribing clinician's office (where the treatment for an individual patient can be adjusted accordingly in a much more timely manner) and in other medical settings lacking LC or GC/MS equipment or requiring rapid test results.

Aripiprazole is:

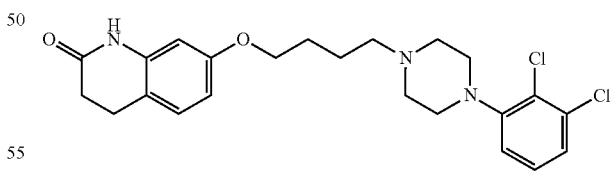

SUMMARY OF THE INVENTION

The present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i).

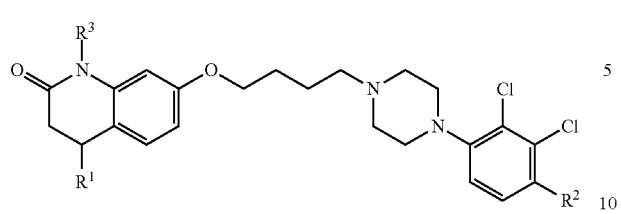

Formula I wherein:
R¹ is H,

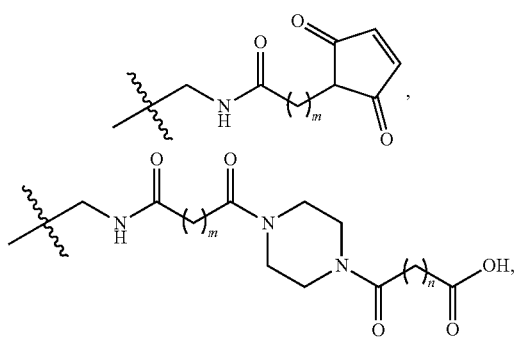

NH$_2$, NHC(O)(CH$_2$)$_m$CO$_2$H, or Z—(Y)$_p$-G;
R³ is H, or W—(Y)$_p$-G; provided that two of R¹, R², R³ must be H, and further provided that R¹, R² and R³ may not all be H simultaneously;
wherein:
Z is selected from the group consisting of:
—N(R⁴)—, —O—, —S—, -alkyl-, -alkoxyalkyl-, -aminoalkyl-, -thioalkyl-, -heteroalkyl-, -alkylcarbonyl-,

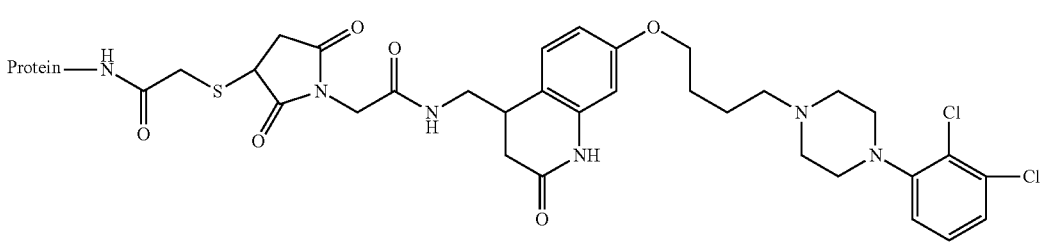

wherein:
W is selected from the group consisting of:
—C(O)—, -alkyl-, -alkoxyalkyl-, -aminoalkyl-, -thioalkyl-, -heteroalkyl-, -alkylcarbonyl-;
R⁴ is H, an alkyl group, cycloalkyl group, aralkyl group or substituted or unsubstituted aryl group;
Y is an organic spacer group;
G is a functional linking group capable of binding to a carrier;
p is 0 or 1;
m is 1, 2, 3, 4, or 5; and
n is 1, 2, 3, 4, or 5.

Presently preferred embodiments of the antibody of the subject invention are the antibodies designated 3C1, 3D7, and 5C7, generated against the compound having Formula II.

Formula II (Compound 6)

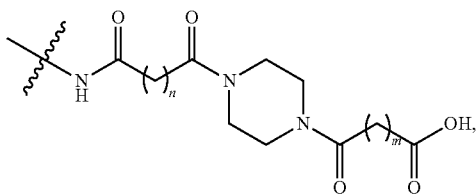

Compound 6

The antibodies of the subject invention can be provided in assay kits and assay devices, with a presently preferred device being a lateral flow assay device which provides for point-of-care analysis.

The invention further provides a method of producing an antibody which binds to aripiprazole, the method comprising: (i) selecting a host cell for antibody production; and (ii) inoculating the host with a conjugate of a compound of Formula I and an immunogenic carrier, wherein the host produces an antibody which binds to aripiprazole. Further provided is a method of producing a hybridoma cell line capable of producing a monoclonal antibody which binds to aripiprazole. The method comprises: (i) selecting a host for antibody production; (ii) inoculating the host with a conjugate of a compound of Formula I and an immunogenic carrier; (iii) fusing a cell line from the inoculated host with a continuously dividing cell to create a fused cell capable of producing a monoclonal antibody which binds to aripiprazole; and (iv) cloning the fused cell so as to obtain a hybridoma cell line.

The invention further provides a method of detecting aripiprazole in a sample. The method comprises: (i) contacting a sample with an antibody according to the subject invention which is labeled with a detectable marker, wherein the labeled antibody and aripiprazole present in the sample form a labeled complex; and (ii) detecting the labeled complex so as to detect aripiprazole in the sample.

Further provided is a competitive immunoassay method for detecting aripiprazole in a sample. The method comprises: (i) contacting a sample with an antibody according to the subject invention, and with aripiprazole or a competitive binding partner of aripiprazole, wherein one of the antibody and the aripiprazole or competitive binding partner thereof is labeled with a detectable marker, and wherein sample aripiprazole competes with the aripiprazole or competitive binding partner thereof for binding to the antibody; and (ii) detecting the label so as to detect sample aripiprazole.

Further objects, features and advantages of the present invention will be apparent to those skilled in the art from detailed consideration of the preferred embodiments that follow.

DETAILED DESCRIPTION OF PREFERRED EMBODIMENTS

Figure 1:
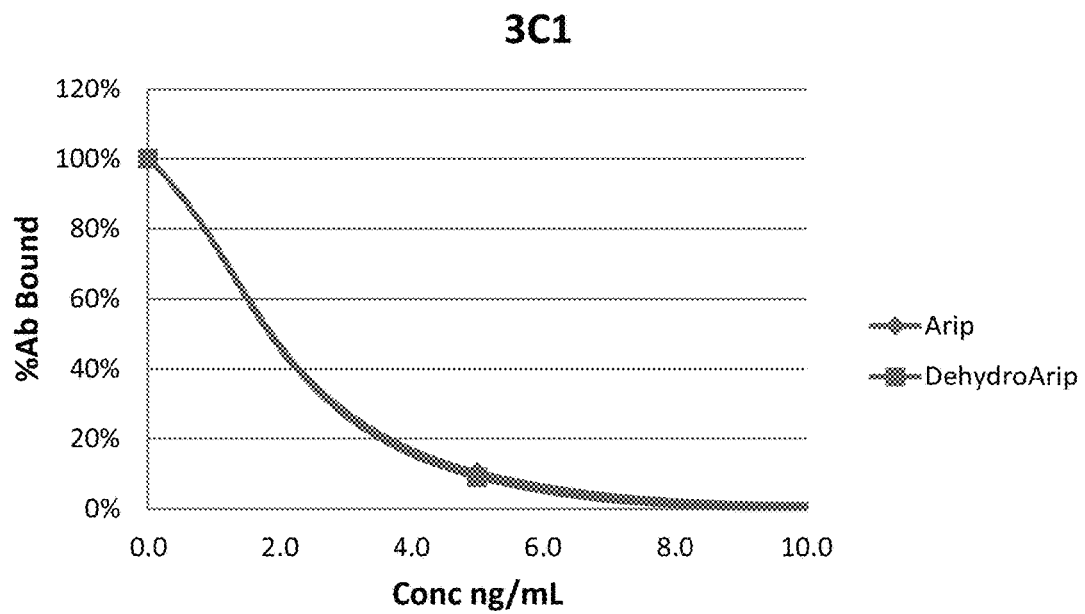
FIG. 1 shows Competitive ELISA results generated with hybridoma 3C1.

The invention provides an isolated antibody which binds to aripiprazole. The invention further provides an assay kit and an assay device comprising the antibody. Also provided are methods of producing the antibody and of producing a hybridoma cell line capable of producing the antibody. Further provided is a method of detecting aripiprazole in a sample, including a competitive immunoassay method.

In one embodiment, the present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i).

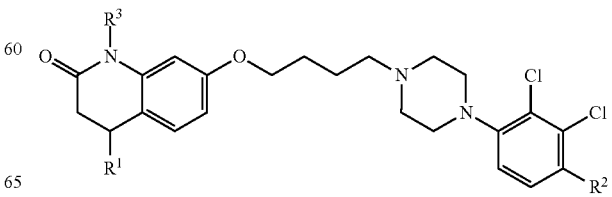

Formula I wherein:
$R^1$ is H,

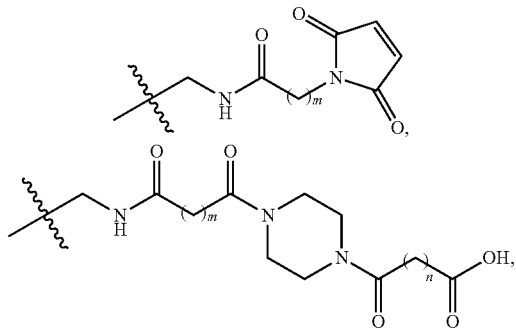

$CH_2NH_2$,
$CH_2NHC(O)(CH_2)_mCO_2H$, or $Z-(Y)_p-G$;
$R^2$ is H,

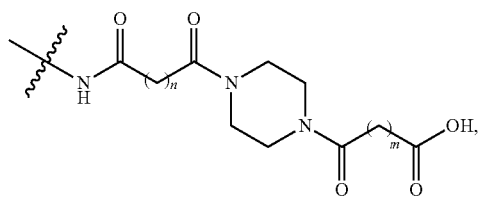

$NH_2$, $NHC(O)(CH_2)_mCO_2H$, or $Z-(Y)_p-G$;
$R^3$ is H, or $W-(Y)_p-G$; provided that two of $R^1$, $R^2$, $R^3$ must be H, and further provided that $R^1$, $R^2$ and $R^3$ may not all be H simultaneously;
wherein:
Z is selected from the group consisting of:
—$N(R^4)$—, —O—, —S—, -alkyl-, -alkoxyalkyl-, -aminoalkyl-, -thioalkyl-, -heteroalkyl-, -alkylcarbonyl-,

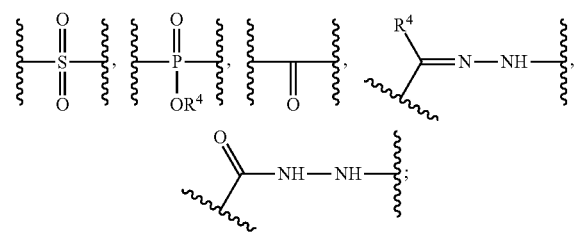

wherein:
W is selected from the group consisting of:
—C(O)—, -alkyl-, -alkoxyalkyl-, -aminoalkyl-, -thioalkyl-, -heteroalkyl-, -alkylcarbonyl-;
$R^4$ is H, an alkyl group, cycloalkyl group, aralkyl group or substituted or unsubstituted aryl group;
Y is an organic spacer group;
G is a functional linking linking group capable of binding to a carrier;
p is 0 or 1;
m is 1, 2, 3, 4, or 5; and
n is 1, 2, 3, 4, or 5.

In a further embodiment, the present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i); wherein:
$R^1$ is H,

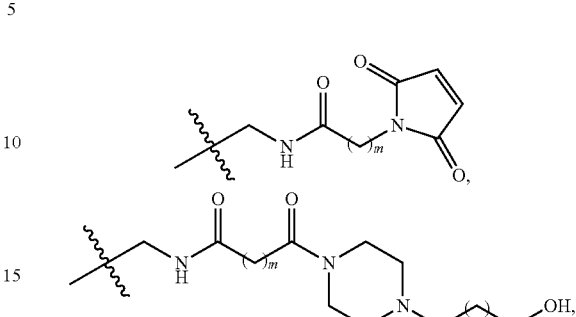

$CH_2NH_2$,
$CH_2NHC(O)(CH_2)_mCO_2H$, or $Z-(Y)_p-G$;
$R^2$ is H,

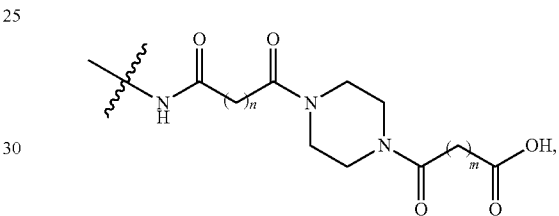

$NH_2$, $NHC(O)(CH_2)_mCO_2H$, or $Z-(Y)_p-G$;
$R^3$ is H, provided that either $R^1$ or $R^2$ must be H, and further provided that both $R^1$ and $R^2$ may not be H simultaneously;
wherein:
Z is selected from the group consisting of:
—$N(R^4)$—, —O—, —S—, -alkyl-, -alkoxyalkyl-, -aminoalkyl-, -thioalkyl-, -heteroalkyl-, -alkylcarbonyl-,

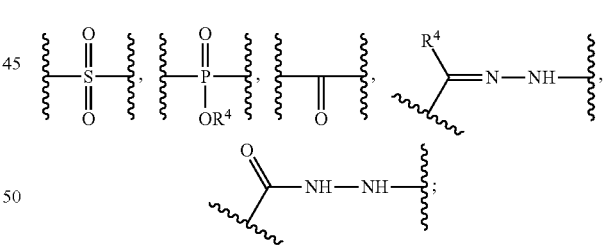

$R^4$ is H, an alkyl group, cycloalkyl group, aralkyl group or substituted or unsubstituted aryl group;
Y is an organic spacer group;
G is a functional linking group capable of binding to a carrier;
p is 0, or 1;
m is 1, 2, 3, 4, or 5;
n is 1, 2, 3, 4, or 5.

In a further embodiment, the present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i); wherein:

$R^1$ is H, or $CH_2NH-(Y)_p-G$;
$R^2$ is H, or $NH-(Y)_p-G$;
$R^3$ is H, provided that either $R^1$ or $R^2$ must be H, and further provided that both $R^1$ and $R^2$ may not be H simultaneously; wherein:
Y is an organic spacer group;
G is a functional linking group capable of binding to a carrier; and
p is 1.

In a further embodiment, the present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i); wherein:
$R^1$ is H,

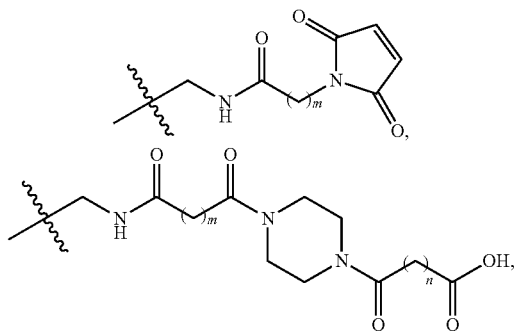

$CH_2NH_2$, or
$CH_2NHC(O)(CH_2)_mCO_2H$;
$R^2$ is H,

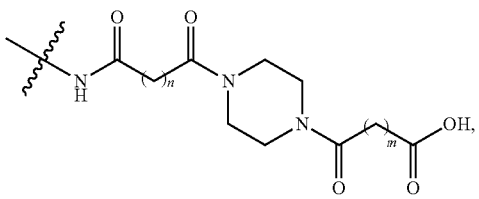

$NH_2$, or $NHC(O)(CH_2)_nCO_2H$; provided that either $R^1$ or $R^2$ must be H, and further provided that both $R^1$ and $R^2$ may not be H simultaneously;
$R^3$ is H;
m is 1, 2, 3, 4, or 5;
n is 1, 2, 3, 4, or 5.

In a further embodiment, the present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i); wherein: $R^1$ is H, $CH_2NH_2$, or $CH_2NHC(O)(CH_2)_mCO_2H$; $R^2$ is H, $NH_2$, or $NHC(O)(CH_2)_nCO_2H$; provided that either $R^1$ or $R^2$ must be H, and further provided that both $R^1$ and $R^2$ may not be H simultaneously;
$R^3$ is H;
m is 1, 2 or 3;
n is 1, 2 or 3.

In a further embodiment, the present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i); wherein:
$R^1$ is H, $CH_2NH_2$, or $CH_2NHC(O)(CH_2)_mCO_2H$;
$R^2$ is H, $NH_2$, or $NHC(O)(CH_2)_nCO_2H$; provided that either $R^1$ or $R^2$ must be H, and further provided that both $R^1$ and $R^2$ may not be H simultaneously;
$R^3$ is H;
m is 2;
n is 2.

In a preferred embodiment, the present invention is directed to an isolated antibody or a binding fragment thereof, which binds to aripiprazole and which: (i) is generated in response to a conjugate of a compound of Formula III and an immunogenic carrier; or (ii) competes for an epitope which is the same as an epitope bound by the antibody of (i).

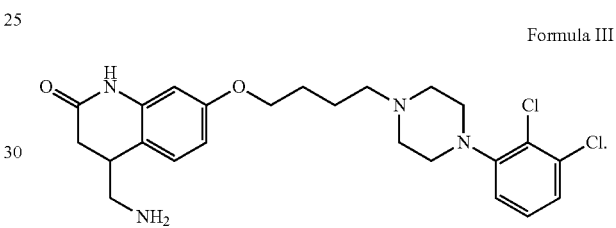

Formula III

In a further preferred embodiment, the present invention is directed to an isolated antibody or a binding fragment thereof, which binds to aripiprazole and which: (i) is generated in response to a conjugate of a compound of Formula IV and an immunogenic carrier; or (ii) competes for an epitope which is the same as an epitope bound by the antibody of (i).

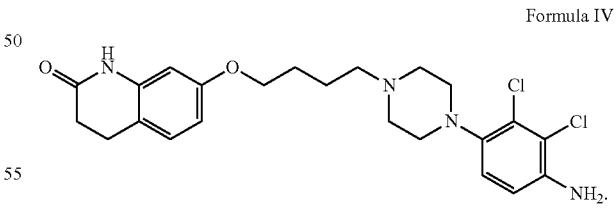

Formula IV

In another preferred embodiment, the present invention is directed to an isolated antibody or a binding fragment thereof, which binds to aripiprazole and which: (i) is generated in response to a conjugate of a compound of Formula V and an immunogenic carrier; or (ii) competes for an epitope which is the same as an epitope bound by the antibody of (i).

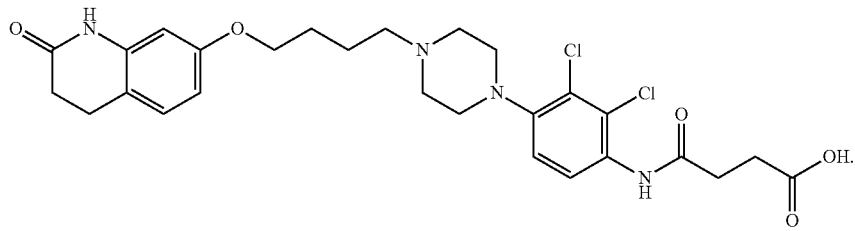

Formula V

In an additional preferred embodiment, the present invention is directed to an isolated antibody or a binding fragment thereof, which binds to aripiprazole and which: (i) is generated in response to a conjugate of a compound of Formula VI and an immunogenic carrier; or (ii) competes for an epitope which is the same as an epitope bound by the antibody of (i).

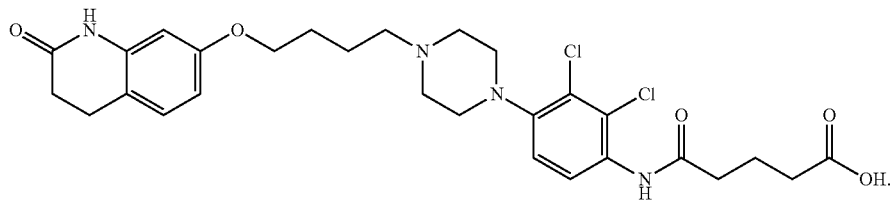

Formula VI

In yet another additional preferred embodiment, the present invention is directed to an isolated antibody or a binding fragment thereof, which binds to aripiprazole and which: (i) is generated in response to a conjugate of a compound of Formula VII and an immunogenic carrier; or (ii) competes for an epitope which is the same as an epitope bound by the antibody of (i).

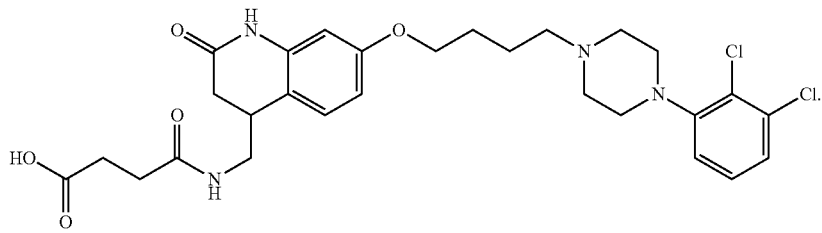

Formula VII

In yet an additional additional preferred embodiment, the present invention is directed to an isolated antibody or a binding fragment thereof, which binds to aripiprazole and which: (i) is generated in response to a conjugate of a compound of Formula VIII and an immunogenic carrier; or (ii) competes for an epitope which is the same as an epitope bound by the antibody of (i).

Formula VIII

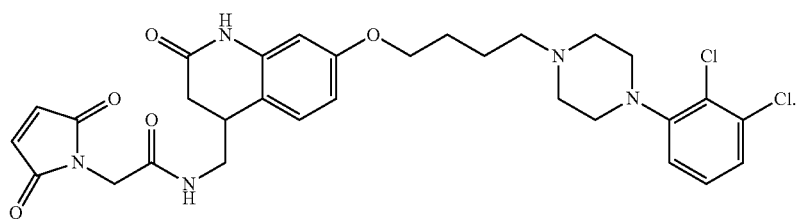

Preferably, the antibody of the subject invention is generated in response to a conjugate of a compound selected from the compounds of: Formula I, Formula III, Formula IV, Formula V, Formula VI, Formula VII, and Formula VIII; and an immunogenic carrier.

Further details of the compounds described by the formulas above and the conjugates formed by the compounds and an immunogenic carrier are provided in the section below entitled "Compounds, Conjugates and Immunogens".

Further details of the antibodies of the subject invention are provided in the section below entitled "Antibodies".

The subject invention further provides an assay kit comprising the antibody, as well as an assay device comprising the antibody. Preferably, the assay device is a lateral flow assay device. Further details of the assay kits and assay devices are provided below in the section entitled "Assay Kits and Devices".

The invention further provides a method of producing an antibody which binds to aripiprazole, the method comprising: (i) selecting a host cell for antibody production; and (ii) inoculating the host with a conjugate of a compound of Formula I and an immunogenic carrier, wherein the host produces an antibody which binds to aripiprazole. In additional embodiments, the conjugate used in the method can be a conjugate of a compound selected from the compounds of: Formula III, Formula IV, Formula V, Formula VI, Formula VII, and Formula VIII; and an immunogenic carrier. Further details on the production of the antibodies of the subject invention are provided in the section below entitled "Antibodies".

Further provided is a method of producing a hybridoma cell line capable of producing a monoclonal antibody which binds to aripiprazole. The method comprises: (i) selecting a host for antibody production; (ii) inoculating the host with a conjugate of a compound of Formula I and an immunogenic carrier; (iii) fusing a cell line from the inoculated host with a continuously dividing cell to create a fused cell capable of producing a monoclonal antibody which binds to aripiprazole; and (iv) cloning the fused cell so as to obtain a hybridoma cell line. In additional embodiments, the conjugate used in the method can be a conjugate of a compound selected from the compounds of: Formula III, Formula IV, Formula V, Formula VI, Formula VII, and Formula VIII; and an immunogenic carrier. Further details of the production of hybridomas in accordance with the subject invention are provided in the section below entitled "Antibodies".

The invention further provides a method of detecting aripiprazole in a sample. The method comprises: (i) contacting a sample with an antibody according to the subject invention which is labeled with a detectable marker, wherein the labeled antibody and aripiprazole present in the sample form a labeled complex; and (ii) detecting the labeled complex so as to detect aripiprazole in the sample. Further details of the method of detecting aripiprazole in accordance with the subject invention are provided in the section below entitled "Immunoassays".

Further provided is a competitive immunoassay method for detecting aripiprazole in a sample. The method comprises: (i) contacting a sample with an antibody according to the subject invention, and with aripiprazole or a competitive binding partner of aripiprazole, wherein one of the antibody and the aripiprazole or competitive binding partner thereof is labeled with a detectable marker, and wherein sample aripiprazole competes with the aripiprazole or competitive binding partner thereof for binding to the antibody; and (ii) detecting the label so as to detect sample aripiprazole. Further details of the competitive immunoassay method of detecting aripiprazole in accordance with the subject invention are provided in the section below entitled "Immunoassays".

In a preferred embodiment of the subject invention, the detection of aripiprazole is accompanied by the detection of one or more analytes in addition to aripiprazole. Preferably the one or more analytes are anti-psychotic drugs other than aripiprazole, and more preferably the anti-psychotic drugs other than aripiprazole are selected from the group consisting of: risperidone, paliperidone, quetiapine, olanzapine, and metabolites thereof.

As discussed above, the antibodies of the subject invention can be used in assays to detect the presence and/or amount of the anti-psychotic drug in patient samples. Such detection permits therapeutic drug monitoring enabling all of the benefits thereof. Detection of levels of anti-psychotic drugs may be useful for many purposes, each of which represents another embodiment of the subject invention, including: determination of patient adherence or compliance with prescribed therapy; use as a decision tool to determine whether a patient should be converted from an oral anti-psychotic regimen to a long-acting injectable anti-psychotic regimen; use as a decision tool to determine if the dose level or dosing interval of oral or injectable anti-psychotics should be increased or decreased to ensure attainment or maintenance of efficacious or safe drug levels; use as an aid in the initiation of anti-psychotic drug therapy by providing evidence of the attainment of minimum pK levels; use to determine bioequivalence of anti-psychotic drug in multiple formulations or from multiple sources; use to assess the impact of polypharmacy and potential drug-drug interactions; and use as an indication that a patient should be excluded from or included in a clinical trial and as an aid in the subsequent monitoring of adherence to clinical trial medication requirements.

Compounds, Conjugates and Immunogens

In relation to the compounds and conjugates and immunogens, the following abbreviations are used: AIBN is azobisisobutyronitrile; AMAS is N-(α-maleimidoacetoxy) succinimide ester; BTG is bovine thyroglobulin; Bu₃N is tributylamine; DMF is N,N-dimethylformamide; EDTA is ethylenediaminetetraaceticacid; EtOH is ethyl alcohol; KLH is keyhole limpet hemocyanin; NBS is N-bromo succinimide; SATA is N-succinimidyl S-acetylthioacetate; THF is tetrahydrofuran; TFA is trifluoroacetic acid; DCC is dicyclohexylcarbodiimide; DIC is diisopropylcarbodiimide; DMAP is N,N-dimethyl-4-aminopyridine; EDC is 1-ethyl-3(3-dimethylaminopropyl) carbodiimidehydrochloride; NHS is N-hydroxysuccinimide; TFP is Tetrafluorophenyl; PNP is p-nitrophenyl; TBTU is O-(Benzotriazol-1-yl)-N,N, N',N'-tetramethyluronium tetrafluoroborate; HOBT is N-Hydroxybenzotriazole; DEPBT is 3-(diethoxyphosphoryloxy)-1,2,3-benzotrazin-4(3H)-one; BOP-Cl is Bis(2-oxo-3-oxazolidinyl)phosphonic chloride; DTT is dithioerythritol.

The term "conjugate" refers to any substance formed from the joining together of separate parts. Representative conjugates include those formed by the joining together of a small molecule, such as the compounds of Formula I, and a large molecule, such as a carrier or a polyamine polymer, particularly a protein. In the conjugate the small molecule may be joined at one or more active sites on the large molecule.

The term "hapten" refers to a partial or incomplete antigen. A hapten is a protein-free substance, which is not capable of stimulating antibody formation, but which does react with antibodies. The antibodies are formed by coupling a hapten to a high molecular weight immunogenic carrier, and then injecting this coupled product, i.e., an immunogen, into a human or animal subject.

The term "immunogen" refers to a substance capable of eliciting, producing, or generating an immune response in an organism.

An "immunogenic carrier," as used herein, is an immunogenic substance, commonly a protein, that can join at one or more positions with haptens, thereby enabling the production of antibodies that can bind with these haptens. Examples of immunogenic carrier substances include, but are not limited to, proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Various protein types may be employed as immunogenic carriers, including without limitation, albumins, serum proteins, lipoproteins, etc. Illustrative proteins include bovine serum albumin, keyhole limpet hemocyanin, egg ovalbumin, bovine thyroglobulin, fraction V human serum albumin, rabbit albumin, pumpkin seed globulin, diphtheria toxoid, tetanus toxoid, botilinus toxin, succinylated proteins, and synthetic poly(aminoacids) such as polylysine.

Immunogenic carriers can also include poly amino-polysaccharides, which are a high molecular weight polymers built up by repeated condensations of monosaccharides. Examples of polysaccharides are starches, glycogen, cellulose, carbohydrate gums such as gum arabic, agar, and so forth. The polysaccharide also contains poly(amino acid) residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

The term "derivative" refers to a chemical compound or molecule made from a parent compound by one or more chemical reactions.

The term "analogue" of a chemical compound refers to a chemical compound that contains a chain of carbon atoms and the same particular functional groups as a reference compound, but the carbon chain of the analogue is longer or shorter than that of the reference compound.

A "label," "detector molecule," "reporter" or "detectable marker" is any molecule which produces, or can be induced to produce, a detectable signal. The label can be conjugated to an analyte, immunogen, antibody, or to another molecule such as a receptor or a molecule that can bind to a receptor such as a ligand, particularly a hapten or antibody. A label can be attached directly or indirectly by means of a linking or bridging moiety. Non-limiting examples of labels include radioactive isotopes (e.g., $^{125}$I), enzymes (e.g. β-galactosidase, peroxidase), enzyme fragments, enzyme substrates, enzyme inhibitors, coenzymes, catalysts, fluorophores (e.g., rhodamine, fluorescein isothiocyanate or FITC, or Dylight 649), dyes, chemiluminescers and luminescers (e.g., dioxetanes, luciferin), or sensitizers.

As used herein, a "spacer" refers to a portion of a chemical structure which connects two or more substructures such as haptens, carriers, immunogens, labels or binding partners through a functional linking group. These spacer groups are composed of the atoms typically present and assembled in ways typically found in organic compounds and so may be referred to as "organic spacing groups". The chemical building blocks used to assemble the spacers will be described hereinafter in this application. Among the preferred spacers are straight or branched, saturated or unsaturated carbon chains. These carbon chains may also include one or more heteroatoms within the chain, one or more heteroatoms replacing one or more hydrogens of any carbon atom in the chain, or at the termini of the chains. By "heteroatoms" is meant atoms other than carbon which are chosen from the group consisting of oxygen, nitrogen, phosphorous and sulfur, wherein the nitrogen, phosphorous and sulfur atoms may exist in any oxidation state and may have carbon or other heteroatoms bonded to them. The spacer may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. Preferred chain lengths are between 1 to 20 atoms.

A "functional linking group" refers to a reactive group that is present on a hapten and may be used to provide an available reactive site through which the hapten portion may be coupled to another moiety through formation of a covalent chemical bond to produce a conjugate of a hapten with another moiety (such as a label or carrier). The hapten may be linked in this way to a moiety such as biotin to form a competitive binding partner.

Spacer groups may be used to link the hapten to the carrier. Spacers of different lengths allow one to attach the hapten with differing distances from the carrier for presentation to the immune system of the animal or human being immunized for optimization of the antibody formation process. Attachment to different positions in the hapten molecule allows the opportunity to present specific sites on the hapten to the immune system to influence antibody recognition. The spacer may contain hydrophilic solubilizing groups to make the hapten derivative more soluble in aqueous media. Examples of hydrophilic solubilizing groups include but are not limited to polyoxyalkyloxy groups, for example, polyethylene glycol chains; hydroxyl, carboxylate and sulfonate groups.

The term "nucleophilic group" or "nucleophile" refers to a species that donates an electron-pair to form a chemical bond in a reaction. The term "electrophilic group" or "electrophile" refers to a species that accepts an electron-pair from a nucleophile to form a chemical bond in a reaction.

The term "substituted" refers to substitution of an atom or group of atoms in place of a hydrogen atom on a carbon atom in any position on the parent molecule. Non limiting examples of substituents include halogen atoms, amino, hydroxy, carboxy, alkyl, aryl, heteroalkyl, heteroaryl, cyano, alkoxy, nitro, aldehyde and ketone groups.

The term "alkyl" refers to saturated or unsaturated linear and branched chain radicals of up to 12 carbon atoms, unless otherwise indicated, and is specifically intended to include radicals having any degree or level of saturation. Alkyl includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated monocyclic or bicyclic hydrocarbon ring radical composed of from 3 to 10 carbon atoms. Alkyl substituents may optionally be present on the ring. Examples include cyclopropyl, 1,1-dimethyl cyclobutyl, 1,2,3-trimethylcyclopentyl, cyclohexyl and cyclohexenyl.

The term "heteroalkyl" refers to an alkyl group that includes one or more heteroatoms within the chain, one or more heteroatoms replacing one or more hydrogens of any carbon atom in the chain, or at termini of the chains.

The term "aminoalkyl" refers to at least one primary or secondary amino group bonded to any carbon atom along an alkyl chain.

The term "alkoxy" refers to straight or branched chain radicals of up to 12 carbon atoms, unless otherwise indicated, bonded to an oxygen atom. Examples include but are not limited to methoxy, ethoxy, propoxy, isopropoxy and butoxy.

The term "alkoxyalkyl" refers to at least one alkoxy group bonded to any carbon atom along an alkyl chain.

The term "thioalkyl" refers to at least one sulfur group bonded to any carbon atom along an alkyl chain. The sulfur group may be at any oxidation state and includes sulfoxides, sulfones and sulfates.

The term "carboxylate group" includes carboxylic acids and alkyl, cycloalkyl, aryl or aralkyl carboxylate esters.

The term "alkylcarbonyl" refers to a group that has a carbonyl group bonded to any carbon atom along an alkyl chain.

The term "heteroaryl" refers to 5- to 7-membered mono- or 8- to 10-membered bicyclic aromatic ring radicals, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "aryl" refers to monocyclic or bicyclic aromatic ring radicals containing from 6 to 12 carbons in the ring. Alkyl substituents may optionally be present on the ring. Examples include phenyl, biphenyl and napththalene.

The term "aralkyl" refers to a $C_{1-6}$ alkyl group containing an aryl substituent. Examples include benzyl, phenylethyl or 2-naphthylmethyl.

The term "acyl" refers to the group $-C(O)R_a$, where $R_a$ is hydrogen, alkyl, cycloalkyl, heteroalkyl, aryl, aralkyl and heteroaryl. An "acylating agent" adds the $-C(O)R_a$ group to a molecule.

The term "sulfonyl" refers to the group $-S(O)_2R_b$, where $R_b$ is hydrogen, alkyl, cycloalkyl, heteroalkyl, haloalkyl, aryl, aralkyl and heteroaryl. A "sulfonylating agent" adds the $-S(O)_2R_a$ group to a molecule.

Spacers bearing reactive functional linking groups for the attachment of haptens to carrier moieties may be prepared by a wide variety of methods. The spacer may be formed using a molecule that is differentially functionalized or activated with groups at either end to allow selective sequential reaction with the hapten and the carrier, but the same reactive moiety may also be used at both ends. The groups selected for reaction with the hapten and the functional linking group to be bound to the carrier are determined by the type of functionality on the hapten and the carrier that the hapten is to be bonded with. Spacers and methods of attachment to haptens and carriers include but are not limited to those described by Brinkley, M., A., *Bioconjugate Chem.* 1992, 3:2-13, Hermanson, Greg T., *Bioconjugate Techniques*, Academic Press, London, Amsterdam, Burlington, Mass., USA, 2008 and *Thermo Scientific Pierce Crosslinking Technical Handbook*; available for download or hard copy request from Thermo Scientific 3747 N Meridian Rd, Rockford, Ill. USA 61101, ph 800-874-3723 or at: http://www.piercenet.com/ and references within. Many differentially activated molecules for formation of spacer groups are commercially available from vendors, for example Thermo Scientific.

For haptens bearing an amino group, modes of attachment of the spacer to the hapten include reaction of the amine on the hapten with a spacer building block bearing an acyl halide or active ester. "Active esters" are defined as esters that undergo reaction with a nucleophilic group, for example an amino group, under mild conditions to form a stable linkage. A stable linkage is defined as one that remains intact under conditions of further use, for example subsequent synthetic steps, use as an immunogen, or in a biochemical assay. A preferred example of a stable linkage is an amide bond. Active esters and methods of formation are described by Benoiton, N. L., in Houben-Weyl, *Methods of Organic Chemistry*, Thieme Stuttgart, New York, vol E22 section 3.2:443 and Benoiton, N. L., *Chemistry of Peptide Synthesis*, Taylor and Francis, NY, 2006. Preferred active esters include p-nitrophenyl ester (PNP), N-hydroxysuccinimide ester (NHS) and tetrafluorophenyl ester (TFP). Acyl halides may be prepared by many methods known to one skilled in the art for example, reaction of the carboxylic acid with thionyl chloride or oxalyl chloride, see: Fieser, L. F. and Fieser, M. *Reagents for Organic Synthesis*, John Wiley and Sons, NY, 1967 and references within. These may be converted to other active esters such as p-nitrophenyl esters (PNP) which may also be used in active bi-functional spacers as described by Wu et. al, *Organic Letters,* 2004, 6 (24):4407. N-hydroxysuccinimide (NHS) esters may be prepared by reaction of N,N-disuccinimidyl carbonate (CAS 74124-79-1) with the carboxylic acid of a compound in the presence of an organic base such as triethylamine or diisopropylethylamine in an aprotic solvent under anhydrous conditions as described in Example 35 of WO2012012595 or by using N-hydroxysuccinimide and dicyclohexylcarbodiimide (DCC) or other dehydrating agent, under anhydrous conditions. Tetrafluorophenyl esters (TFP) may be prepared by reaction of carboxylic acids with 2,3,5,6-tetrafluorophenyltrifluoroacetate in the presence of an organic base such as triethylamine or diisopropylethylamine in an aprotic solvent under anhydrous conditions as reported by Wilbur, et. al, *Bioconjugate Chem.*, 2004, 15(1):203. One skilled in the art will recognize that spacers shown in Table 1, among others, can be obtained using known methods and attached to amino-bearing haptens utilizing routine optimization of reaction conditions. These spacers allow attachment of the hapten to a thiol group on a carrier.

TABLE 1

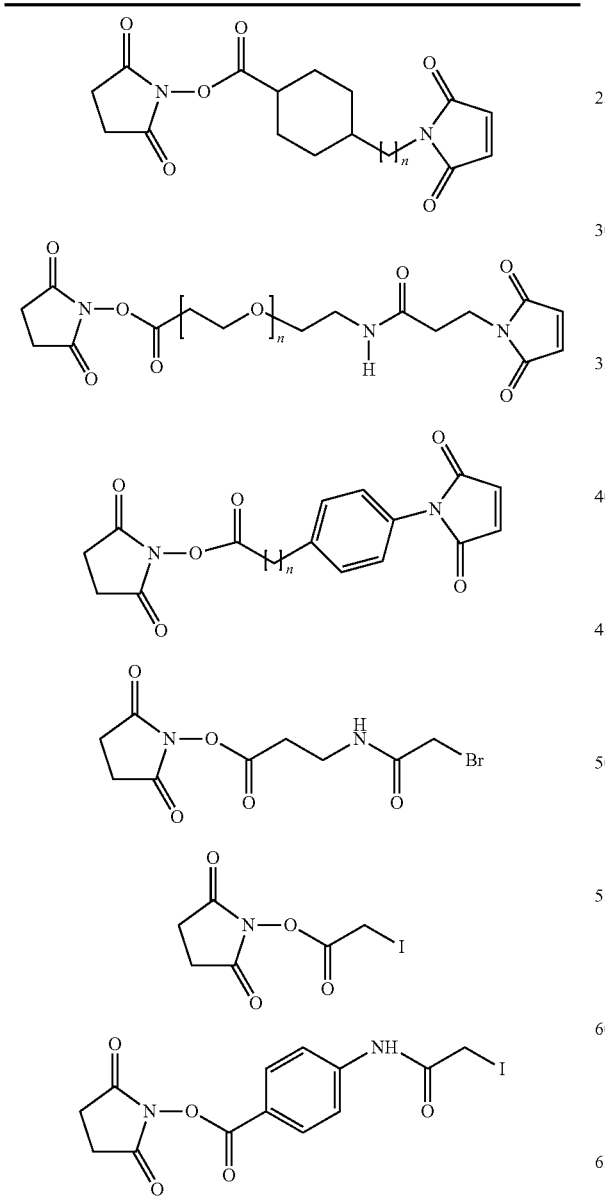

TABLE 1-continued

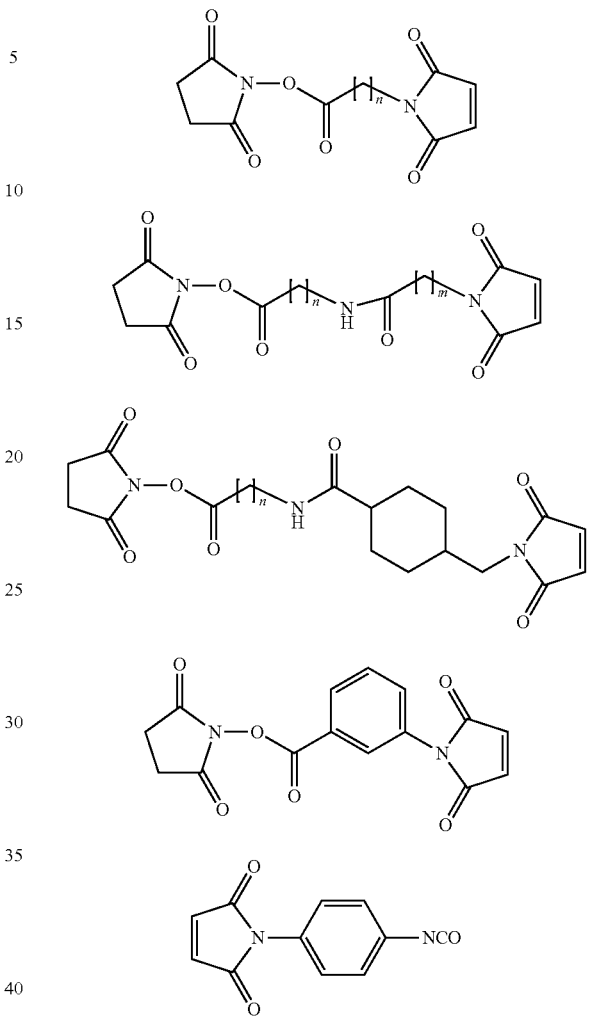

Reasonable values for m and n are between 1 and 10

Direct coupling of the amine on the hapten and a carboxylic acid functionality on the spacer building block in the presence of a coupling agent may also be used as a mode of attachment. Preferred reagents are those typically used in peptide synthesis. Peptide coupling reagents include but are not limited to O-(Benzotriazol-1-yl)-N,N,N',N'-tetramethyluronium tetrafluoroborate (TBTU, CAS #125700-67-6), see: Pruhs, S., *Org. Process. Res. Dev.* 2006, 10:441; N-Hydroxybenzotriazole (HOBT, CAS #2592-95-2) with a carbodiimide dehydrating agent, for example N—N-dicyclohexylcarbodiimide (DCC), diisopropylcarbodiimide (DIC), or 1-ethyl-3(3-dimethylaminopropyl)carbodiimidehydrochloride (EDC), see: Konig W., Geiger, R. *Chem. Ber.,* 1970, 103 (3):788; 3-(diethoxyphosphoryloxy)-1,2,3-benzotrazin-4(3H)-one (DEPBT, CAS#165534-43-0), see: Liu, H. et. al., *Chinese Chemical Letters,* 2002, 13(7):601; Bis(2-oxo-3-oxazolidinyl)phosphonic chloride; (BOP-Cl, CAS#68641-49-6), see: Diago-Meseguer, J et. al. *Synthesis,* 1980, 7:547-51 and others described in detail by Benoiton in *Chemistry of Peptide Synthesis*, CRC Press, Boca Raton, Fla., 2005, Chapter 2, and the technical bulletin provided by Advanced Automated Peptide Protein Technologies (aapptec), 6309 Shepardsville Rd., Louisville Ky. 40228, ph 888 692 9111; www.aapptec.com, and references within. These methods create a stable amide linkage attaching the hapten to the spacer. Examples of spacers that can be obtained using known methods and attached to amino-bearing haptens utilizing routine optimization of reaction conditions employing the methods described and cited above are shown, but not limited to those in Table 2. These spacers allow attachment of the hapten to a thiol group on a carrier.

TABLE 2

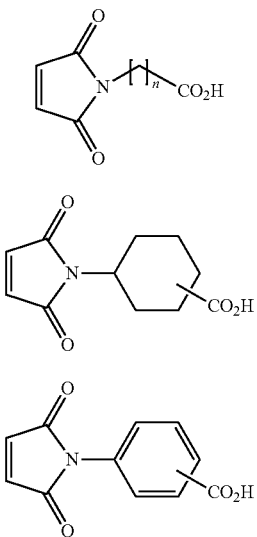

reasonable range for n is between 1-10

Spacers may also be constructed in a step-wise fashion by sequential attachment of appropriate chemical groups to the hapten including the step of forming the functional linking group that is capable of binding to the carrier. See illustrative examples under General Reaction Schemes.

Additionally, when the hapten has a nucleophilic group, for example a thiol group, an amino group or a hydroxyl group which will become the point of attachment of the spacer, the spacer may also be constructed by alkylation of the thiol, amine or hydroxyl group. Any alkyl group that is appropriately substituted with a moiety capable of undergoing a substitution reaction, for example, an alkyl halide, or sulfonic acid ester such as p-Toluenesulfonate, may be used to attach the spacer. Many examples of alkylation reactions are known to one skilled in the art and specific examples may be found in the general chemical literature and optimized through routine experimentation. A discussion of alkylation reactions with many references can be found in Chapter 10 of *March's Advanced Organic Chemistry*, Smith, M. B., and March, J., John Wiley & sons, Inc. NY, 2001. Other linkages may also be employed such as reaction of the nucleophilic moiety, for example an amine, on the hapten with an isocyanate to form a urea or reaction with an isothiocyanate to form a thiourea linkage, see: Li, Z., et. al., *Phosphorus, Sulfur and Silicon and the Related Elements*, 2003, 178(2):293-297. Spacers may be attached to haptens bearing hydroxyl groups via reaction with isocyanate groups to form carbamate or urethane linkages. The spacer may be differentially activated with the isocyanate functional group on one end and a functional linking group capable of reacting with the carrier, see: Annunziato, M. E., Patel, U. S., Ranade, M. and Palumbo, P. S., *Bioconjugate Chem.*, 1993, 4:212-218.

For haptens bearing a carboxylic acid group, modes of attachment of a spacer portion to the hapten include activation of the carboxylic acid group as an acyl halide or active ester, examples of which are shown in Table 3, preparation of which are described previously, followed by reaction with an amino (—NH$_2$—), hydrazino (—NH—NH$_2$—), hydrazido (—C(O)—NH—NH$_2$—) or hydroxyl group (—OH) on the spacer portion to form an amide, hydrazide, diacylhydrazine or ester linkage, or direct coupling of the carboxylic acid group with an amino group on the spacer portion or directly on the carrier with a peptide coupling reagent and/or carbodiimide dehydrating reagent, described previously, examples of which are shown in Tables 4 and 5. Procedures found in references cited previously for formation of activated esters and use of peptide coupling agents may be employed for attachment of carboxylic acid-bearing haptens to spacer building blocks and protein carriers with available amino groups utilizing routine optimization of reaction conditions.

TABLE 3

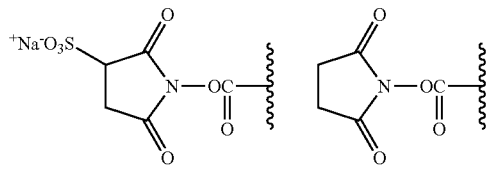

Sulfo NHS and NHS

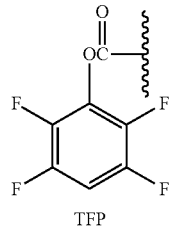

TFP

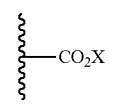

X = Cl, Br

Acyl chloride

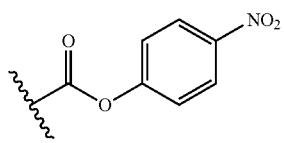

PNP

TABLE 4

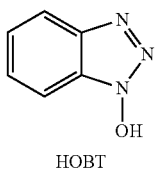

HOBT

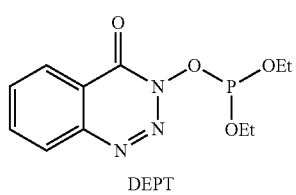 [SMILES: CCOP(OCC)On1nnc2ccccc2c1=O]

DEPT

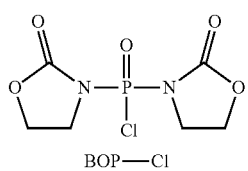

BOP—Cl

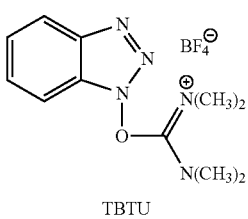

TBTU

TABLE 5

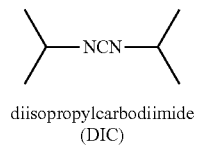

diisopropylcarbodiimide
(DIC)

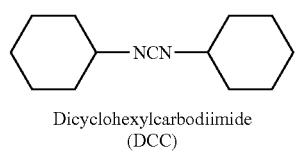

Dicyclohexylcarbodiimide
(DCC)

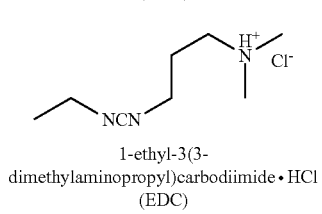

1-ethyl-3(3-
dimethylaminopropyl)carbodiimide • HCl
(EDC)

Other electrophilic groups may be present on the hapten to attach the spacer, for example, a sulfonyl halide

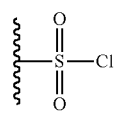

or electrophilic phosphorous group, for example:

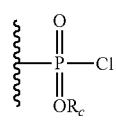

See: Malachowski, William P., Coward, James K., *Journal of Organic Chemistry*, 1994, 59 (25):7616 or:

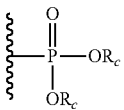

$R_c$ is alkyl, cycloalkyl, aryl, substituted aryl, aralkyl.

See: Aliouane, L., et. al, *Tetrahedron Letters*, 2011, 52(28): 8681.

Haptens that bear aldehyde or ketone groups may be attached to spacers using methods including but not limited to reaction with a hydrazide group $H_2N-NH-C(O)-$ on the spacer to form an acylhydrazone, see: Chamow, S. M., Kogan, T. P., Peers, D. H., Hastings, R. C., Byrn, R. A. and Askenaszi, A., *J. Biol. Chem.*, 1992, 267(22): 15916. Examples of bifunctional hydrazide spacer groups that allow attachment to a thiol group on the carrier are shown in Table 6.

TABLE 6

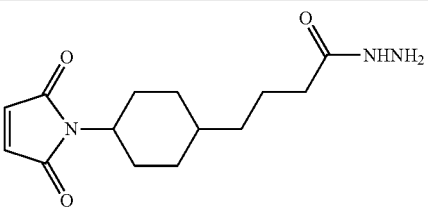 [SMILES: NNC(=O)CCCC1CCC(N2C(=O)C=CC2=O)CC1]

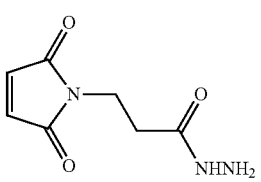 [SMILES: NNC(=O)CCN1C(=O)C=CC1=O]

Haptens may also contain thiol groups which may be reacted with the carrier provided that the carrier has been modified to provide a group that may react with the thiol. Carrier groups may be modified by methods including but not limited to attachment of a group containing a maleimide functional group by reaction of an amino group on the carrier with N-Succinimidyl maleimidoacetate, (AMAS, CAS #55750-61-3), Succinimidyl iodoacetate (CAS#151199-81-4), or any of the bifunctional spacer groups shown in Table 1 to introduce a group which may undergo a reaction resulting in attachment of the hapten to the carrier.

The functional linking group capable of forming a bond with the carrier may be any group capable of forming a stable linkage and may be reactive to a number of different groups on the carrier. The functional linking group may preferably react with an amino group, a carboxylic acid group or a thiol group on the carrier, or derivative thereof. Non-limiting examples of the functional linking group are a carboxylic acid group, acyl halide, active ester (as defined previously), isocyanate, isothiocyanate, alkyl halide, amino group, thiol group, maleimide group, acrylate group ($H_2C=CH-C(O)-$) or vinyl sulfone group $H_2C=CH-SO_2-$) See: Park, J. W., et. al., *Bioconjugate Chem.*, 2012, 23(3): 350. The functional linking group may be present as part of a differentially activated spacer building block that may be reacted stepwise with the hapten and the resulting hapten derivative may then be reacted with the carrier. Alternatively, the hapten may be derivatized with a spacer that bears a precursor group that may be transformed into the functional linking group by a subsequent reaction. When the functional linking group on the spacer is an amine or a carboxylic acid group, the coupling reaction with the carboxylic acid group or amine on the carrier may be carried out directly through the use of peptide coupling reagents according to procedures in the references cited above for these reagents.

Particular disulfide groups, for example, pyridyldisulfides, may be used as the functional linking group on the spacer which may undergo exchange with a thiol group on the carrier to from a mixed disulfide linkage, see: Ghetie, V., et al., *Bioconjugate Chem.*, 1990, 1:24-31. These spacers may be attached by reaction of the amine-bearing hapten with an active ester which is attached to a spacer bearing the pyridyldisulfide group, examples of which include but are not limited to those shown in Table 7.

TABLE 7

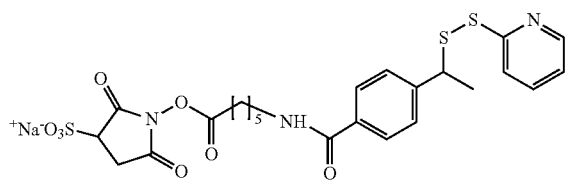

TABLE 7-continued

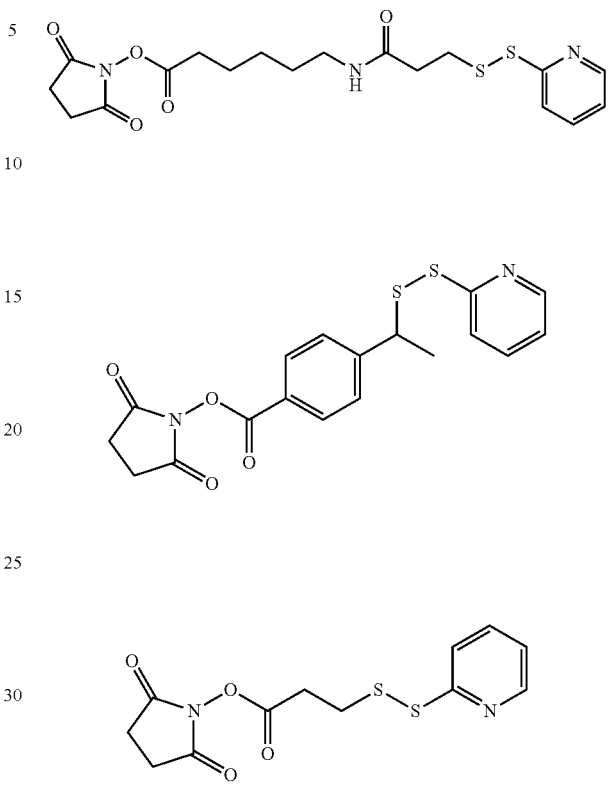

Most often the carrier is a protein and the ε-amino groups of the lysine residues may be used for attachment, either directly by reaction with an amine-reactive functional linking group or after derivitization with a thiol-containing group, including N-Succinimidyl S-Acetylthioacetate, (SATA, CAS 76931-93-6), or an analogue thereof, followed by cleavage of the actetate group with hydroxylamine to expose the thiol group for reaction with the functional linking group on the hapten. Thiol groups may also be introduced into the carrier by reduction of disulfide bonds within protein carriers with mild reducing reagents including but not limited to 2-mercaptoethylamine, see: Bilah, M., et. al., *Bioelectrochemistry*, 2010, 80(1):49, phosphine reagents, see: Kirley, T. L., *Analytical Biochemistry*, 1989, 180(2):231 or dithioerythritol (DTT, CAS 3483-12-3) Cleland, W., *Biochemistry*, 1964, 3:480-482.

General Reaction Schemes

Compounds useful for producing antibodies according to the subject invention can be synthesized in accordance with the general synthetic methods described below. Compounds of Formula I can be prepared by methods known to those who are skilled in the art. The following reaction schemes are only meant to represent examples of the invention and are in no way meant to be a limit of the invention.

Scheme 1

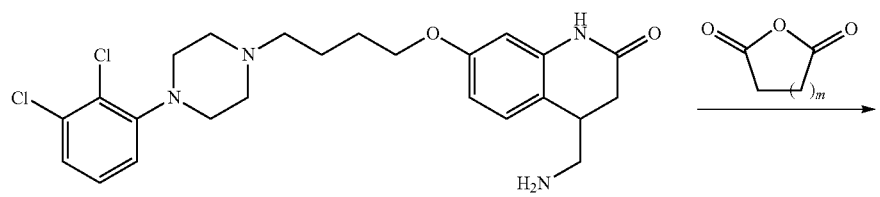

Example 1

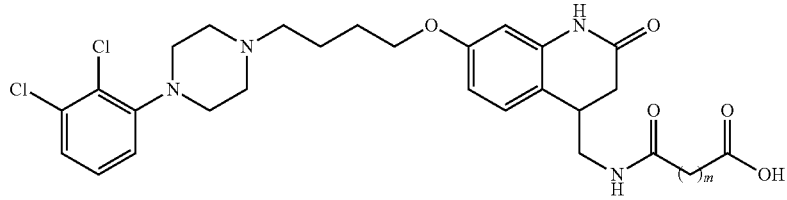

The hapten of Example 1 may be elaborated with spacers by reaction with a cyclic anhydride compound, such as succinic anhydride or glutaric anhydride, as shown in Scheme 1. The reaction may be carried out in a solvent such as THF, at room temperature, overnight.

Scheme 2

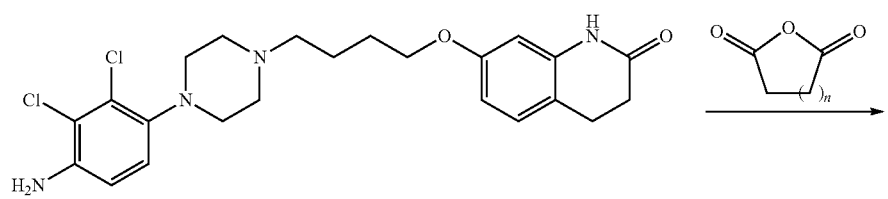

Example 2

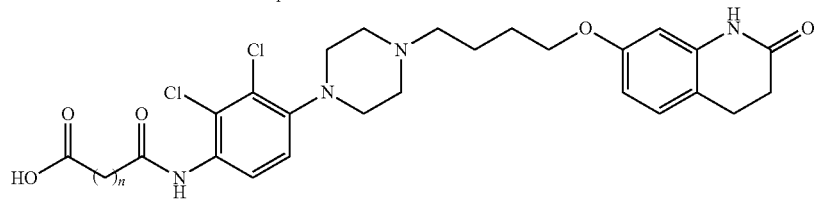

The hapten of Example 2 may be elaborated with spacers by reaction with a cyclic anhydride compound, such as succinic anhydride or glutaric anhydride, as shown in Scheme 2. The reaction may be carried out in a solvent such as pyridine, and heated to about 110° C. in a microwave oven for 3-6 hours.

Scheme 3

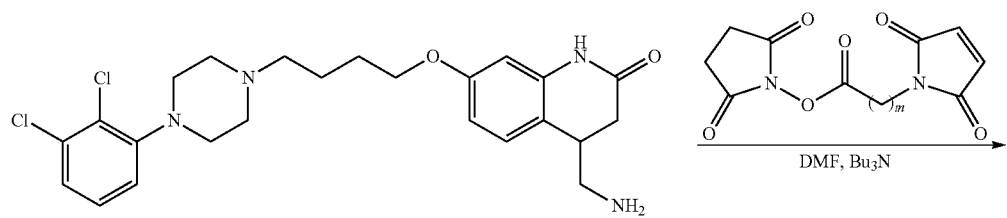

Example 1

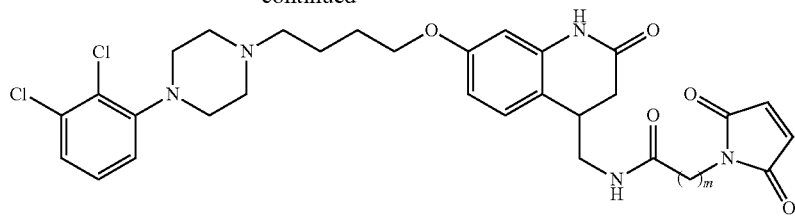

Haptens which terminate in an alkyl amine group, such as Example 1 may be further functionalized with a maleimide group. Those skilled in the art will recognize that the same methodology will be applicable to other alkyl amino derivatives of aripiprazole. Reaction of the aripiprazole derived amine with alkyl-maleimide functionalizing group, such as 2,5-dioxopyrrolidin-1-yl 2-(2,5-dioxo-2,5-dihydro-1H-pyrrol-1-yl)acetate, in a solvent such as DMF, in the presence of a base, such as tributyl amine, at 20° C., for one hour. generates haptens of aripiprazole with a maleimide spacer.

Scheme 4

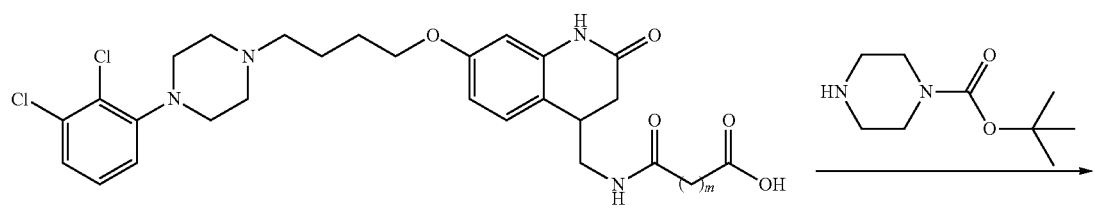

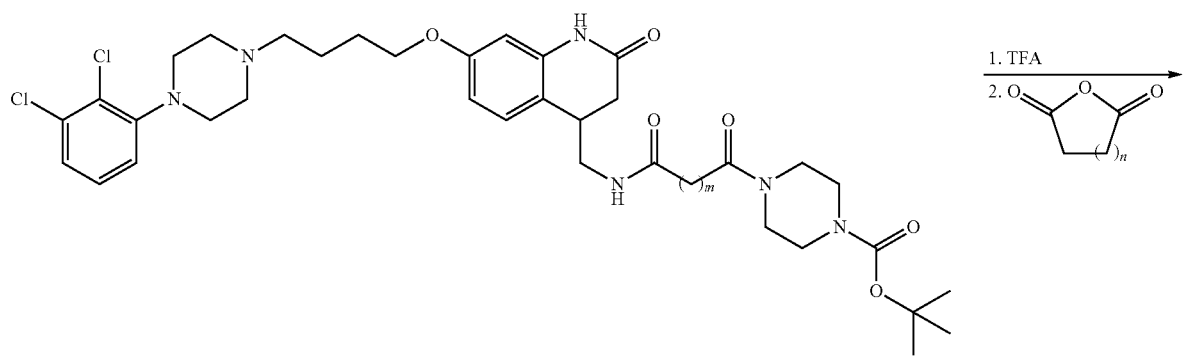

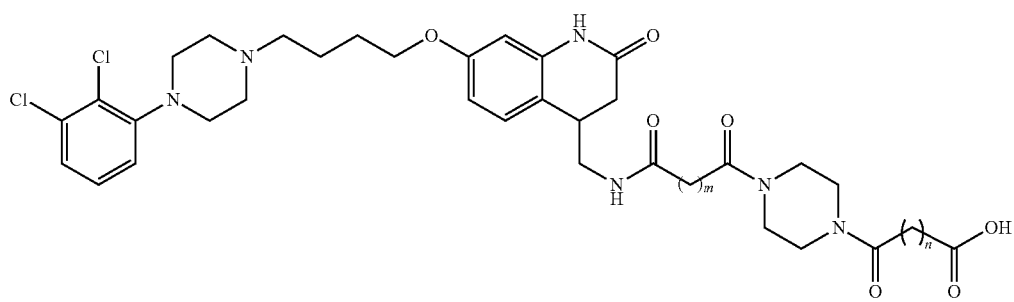

Spacers on haptens may be extended as shown in Scheme 4. Haptens with spacers bearing a carboxylic acid functionality may be dissolved in a suitable solvent, such as dichloromethane, under inert atmosphere, and treated with N-t-butoxycarbonylpiperazine and an appropriate base, such as diisopropylethylamine. The solution may then be treated with diethyl cyanophosphonate to install a piperazine moiety onto the spacer. Deprotection of the piperazine may be accomplished with trifluoroacetic acid or other methods known in the art. Reaction with a cyclic anhydride gives compounds of Formula I where $R^1$ is

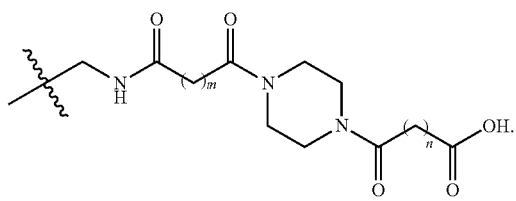

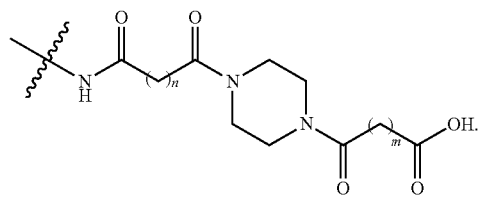

Haptens may also be generated directly from the parent molecule aripiprazole by either acylation or alkylation of the quinolinone nitrogen. Scheme 6 depicts a synthetic route in which an acyl group may be appended to aripiprazole by reaction with the acid chloride of 4-chlorobutyric acid using N,N-dimethyl-4-aminopyridine (DMAP) as a catalyst in the presence of a base such as pyridine in an aprotic solvent, for example N,N-dimethylformamide, see: Example 5, US20110230520. Nucleophilic substitution of the chloride by N-methyl-β-alanine methyl ester may be carried out in Scheme 5

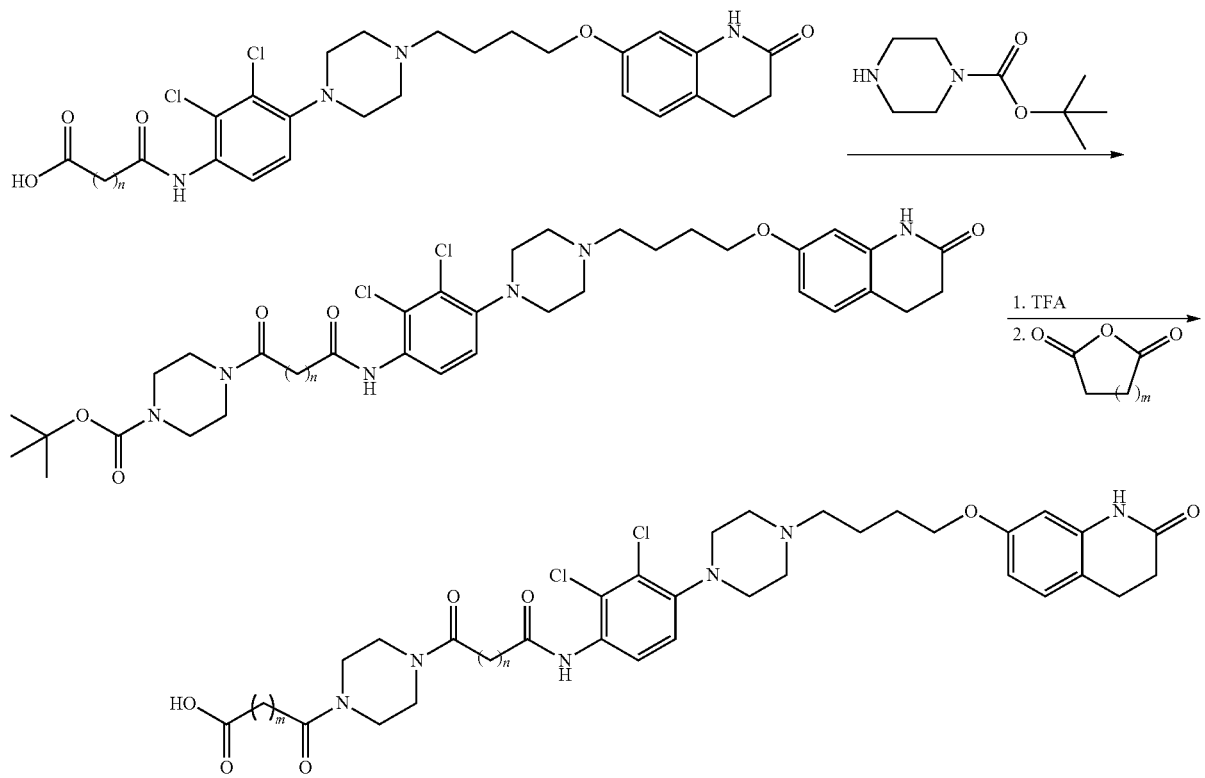

Spacers on haptens may also be extended as shown in Scheme 5. Haptens with spacers bearing carboxylic acid functionality may be dissolved in a suitable solvent, such as dichloromethane, under inert atmosphere, and treated with N-t-butoxycarbonylpiperazine and an appropriate base, such as diisopropylethylamine. The solution may then be treated with diethyl cyanophosphonate to install a piperazine moiety onto the spacer. Deprotection of the piperazine may be accomplished with trifluoroacetic acid or other methods known in the art. Reaction with a cyclic anhydride gives compounds of Formula I where $R^2$ is the presence of sodium iodide and a base, for example potassium carbonate in a dipolar aprotic solvent such as N,N-dimethylformamide, see: Penning, T., D., et. al., *J. Med Chem*, 2002, 45:3482. Hydrolysis of the ester group using standard methods known to one skilled in the art, such as exposure to aqueous base, yields a carboxy-functionalized hapten which may be further elaborated using the methods described previously, one example of which is depicted in Scheme 9 below, to provide a suitably functionalized compound for attachment to an immunogenic carrier.

Scheme 6:

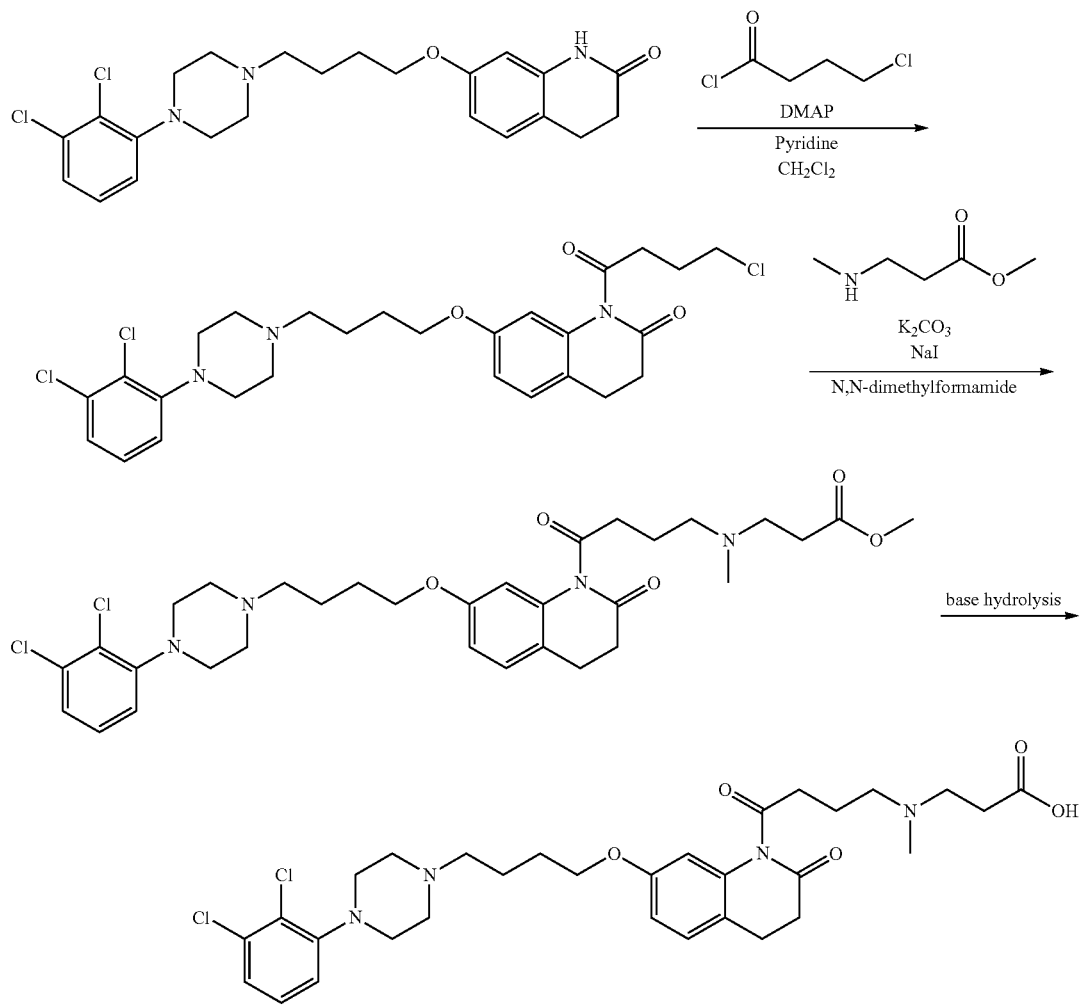

Scheme 7 illustrates a mode of attachment of an alkyl group to the nitrogen of the quinolinone group of aripiprazole using standard alkylation chemistry. An iodo compound, for example methyl-4-iodobutyrate may be reacted with aripiprazole in the presence of a base such as cesium carbonate in a dipolar aprotic solvent such as N,N-dimethylformamide using the method of Example 6 in US20120004165. Hydrolysis of the ester group using standard methods known to one skilled in the art, such as exposure to aqueous base, yields a carboxy-functionalized hapten which may be further elaborated using the methods described previously, one example of which is depicted in Scheme 9 below, to provide a suitably functionalized compound for attachment to an immunogenic carrier.

Scheme 7

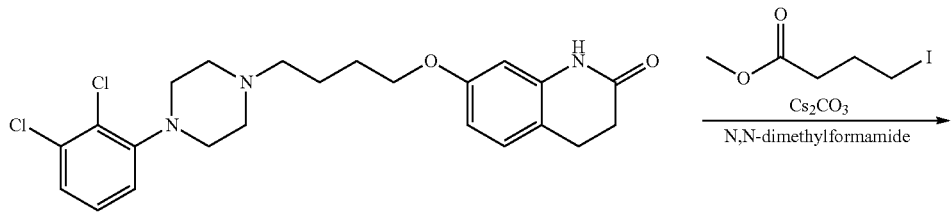

-continued

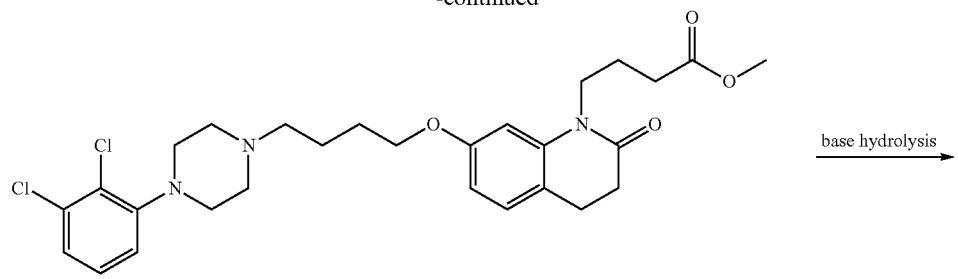

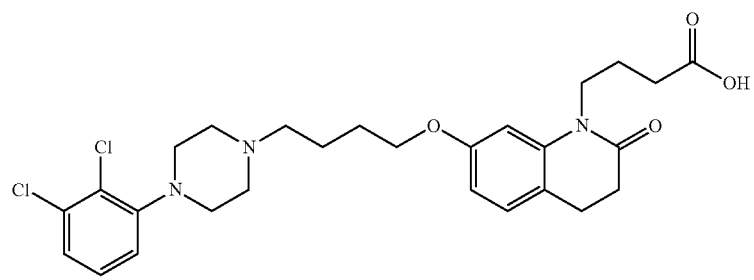

Scheme 8

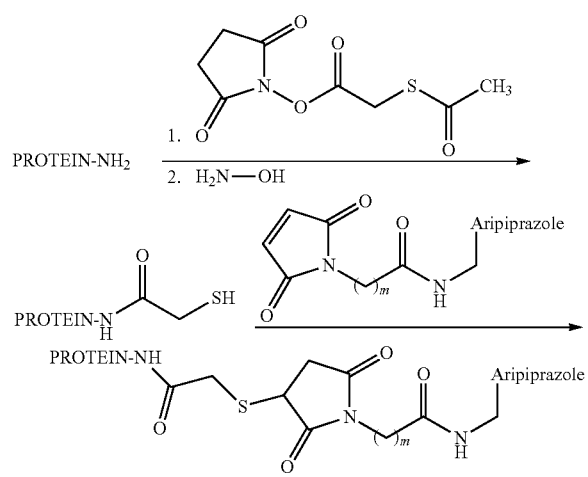

Maleimide functionalized haptens may be conjugated to proteins according to the method shown in Scheme 8. Activation of protein lysine residues by acylation of the epsilon-nitrogen with N-succinimidyl S-acetylthioacetate (SATA), followed by subsequent hydrolysis of the S-acetyl group with hydroxylamine produces a nucleophilic sulfhydryl group. Conjugation of the sulfhydryl activated protein with the maleimide derivatized hapten (prepared as described in general Scheme 3) proceeds via a Michael addition reaction. Suitable proteins are known to those skilled in the art and include keyhole limpet hemocyanin, bovine thyroglobulin, and ovalbumin. While Scheme 8 illustrates protein-hapten conjugation where $R^1$ is

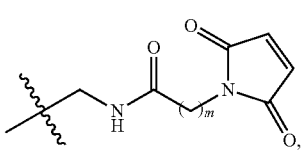

the same chemistry can be used to conjugate any maleimide functionalized hapten to a protein.

Scheme 9:

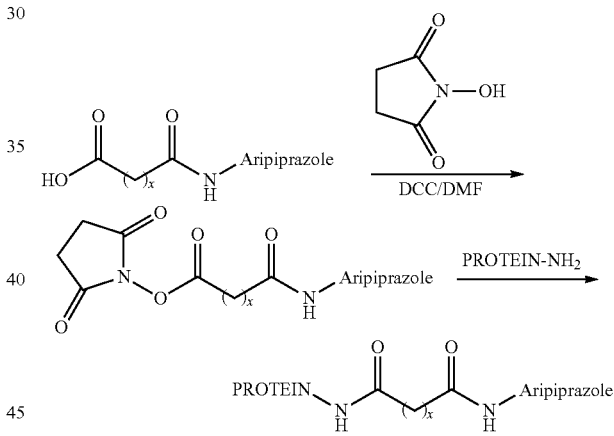

where x is m or n, as defined in Formula I.

Carboxylic acid functionalized haptens may be conjugated to proteins according to the method shown in Scheme 9. Reaction with N-hydroxysuccinimide and a suitable coupling agent, such as dicyclohexylcarbodiimide (DCC) and a base such as tributylamine ($Bu_3N$), in a solvent such as DMF at a temperature of about 20° C., for about 18 hours, activates the carboxylic acid with the hydroxypyrrolidine-2,5-dione leaving group. The activated spacer and hapten may then be conjugated to a protein in a solvent, such as pH 7.5 phosphate buffer, at about 20° C. for about 2.5 hours. Suitable proteins are known to those skilled in the art and include keyhole limpet hemocyanin, bovine thyroglobulin, and ovalbumin. While Scheme 9 illustrates protein-hapten conjugation where $R^2$ is $NHC(O)(CH_2)_nCO_2H$, the same chemistry can be used to conjugate any $CO_2H$ functionalized hapten to a protein.

Antibodies

The present invention is directed to an isolated antibody or a binding fragment thereof, which binds to aripiprazole and which: (i) is generated in response to a conjugate of a compound of Formula I and an immunogenic carrier; or (ii) competes for an epitope which is the same as an epitope bound by the antibody of (i). The term "antibody" refers to a specific protein capable of binding an antigen or portion thereof (in accordance with this invention, capable of binding to an anti-psychotic drug or metabolite thereof). An antibody is produced in response to an immunogen which may have been introduced into a host, e.g., an animal or a human, by injection. The generic term "antibody" includes polyclonal antibodies, monoclonal antibodies, and antibody fragments.

"Antibody" or "antigen-binding antibody fragment" refers to an intact antibody, or a fragment thereof, that competes with the intact antibody for binding. Generally speaking, an antibody or antigen-binding antibody fragment, is said to specifically bind an antigen when the dissociation constant is less than or equal to 1 µM, preferably less than or equal to 100 nM and most preferably less than or equal to 10 nM. Binding can be measured by methods know to those skilled in the art, an example being the use of a BIAcore™ instrument.

Antibody fragments comprise a portion of an intact antibody, preferably the antigen binding or variable region of the intact antibody. Binding fragments include Fab, Fab', $F(ab')_2$, and Fv fragments; diabodies; linear antibodies; single-chain antibody molecules; and multispecific antibodies formed from antibody fragments. An antibody other than a "bispecific" or "bifunctional" antibody is understood to have each of its binding sites identical.

As used herein, "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Two antibodies are said to "bind the same epitope" if one antibody is shown to compete with the second antibody in a competitive binding assay, by any of the methods well known to those skilled in the art (such as the BIAcore™ method referred to above). In reference to a hapten (such as aripiprazole or other anti-psychotic drug), an antibody can be generated against the non-antigenic hapten molecule by conjugating the hapten to an immunogenic carrier. An antibody is then generated which recognizes an "epitope" defined by the hapten.

"Isolated" when used in the context of an antibody means altered "by the hand of man" from any natural state; i.e., that, if it occurs in nature, it has been changed or removed from its original environment, or both. For example, a naturally occurring antibody naturally present in a living animal in its natural state is not "isolated", but the same antibody separated from the coexisting materials of its natural state is "isolated", as the term is employed herein. Antibodies may occur in a composition, such as an immunoassay reagent, which are not naturally occurring compositions, and therein remain isolated antibodies within the meaning of that term as it is employed herein.

"Cross-reactivity" refers to the reaction of an antibody with an antigen that was not used to induce that antibody.

Preferably, the antibody of the subject invention will bind to the drug and any desired pharmacologically active metabolites. By altering the location of the attachment of the immunogenic carrier to the compounds of the invention, selectivity and cross-reactivity with metabolites can be engineered into the antibodies. For aripiprazole, cross-reactivity with dehydroaripiprazole may be desirable. Antibodies may be generated that detect both aripiprazole and dehydroaripiprazole, or antibodies may be generated that detect each separately (thus defining the antibody "specific binding" properties). An antibody specifically binds one or more compounds when its binding of the one or more compounds is equimolar or substantially equimolar.

Methods of producing such antibodies comprise inoculating a host with the conjugate described herein. Suitable hosts include, but are not limited to, mice, rats, hamsters, guinea pigs, rabbits, chickens, donkeys, horses, monkeys, chimpanzees, orangutans, gorillas, humans, and any species capable of mounting a mature immune response. The immunization procedures are well established in the art and are set forth in numerous treatises and publications including "*The Immunoassay Handbook*", 2nd Edition, edited by David Wild (Nature Publishing Group, 2000) and the references cited therein.

Preferably, an immunogen embodying features of the present invention is administered to a host subject, e.g., an animal or human, in combination with an adjuvant. Suitable adjuvants include, but are not limited to, Freund's adjuvant, powdered aluminum hydroxide (alum), aluminum hydroxide together with *Bordetella pertussis*, and monophosphoryl lipid A-synthetic trehalose dicorynomycolate (MPL-TDM).

Typically, an immunogen or a combination of an immunogen and an adjuvant is injected into a mammalian host by one or multiple subcutaneous or intraperitoneal injections. Preferably, the immunization program is carried out over at least one week, and more preferably, over two or more weeks. Polyclonal antibodies produced in this manner can be isolated and purified utilizing methods well know in the art.

Monoclonal antibodies can be produced by the well-established hybridoma methods of Kohler and Milstein, e.g., *Nature* 256:495-497 (1975). Hybridoma methods typically involve immunizing a host or lymphocytes from a host, harvesting the monoclonal antibody secreting or having the potential to secrete lymphocytes, fusing the lymphocytes to immortalized cells, and selecting cells that secrete the desired monoclonal antibody.

A host can be immunized to elicit lymphocytes that produce or are capable of producing antibodies specific for an immunogen. Alternatively, the lymphocytes can be immunized in vitro. If human cells are desired, peripheral blood lymphocytes can be used, although spleen cells or lymphocytes from other mammalian sources are preferred.

The lymphocytes can be fused with an immortalized cell line to form hybridoma cells, a process which can be facilitated by the use of a fusing agent, e.g., polyethylene glycol. By way of illustration, mutant rodent, bovine, or human myeloma cells immortalized by transformation can be used. Substantially pure populations of hybridoma cells, as opposed to unfused immortalized cells, are preferred. Thus, following fusion, the cells can be grown in a suitable medium that inhibits the growth or survival of unfused, immortalized cells, for example, by using mutant myeloma cells that lack the enzyme hypoxanthine guanine phosphoribosyl transferase (HGPRT). In such an instance, hypoxanthine, aminopterin, and thymidine can be added to the medium (HAT medium) to prevent the growth of HGPRT-deficient cells while permitting hybridomas to grow.

Preferably, immortalized cells fuse efficiently, can be isolated from mixed populations by selection in a medium such as HAT, and support stable and high-level expression of antibody following fusion. Preferred immortalized cell lines include myeloma cell lines available from the American Type Culture Collection, Manassas, Va.

Because hybridoma cells typically secrete antibody extracellularly, the culture media can be assayed for the presence of monoclonal antibodies specific for the anti-psychotic drug. Immunoprecipitation of in vitro binding assays, for example, radioimmunoassay (RIA) or enzyme-linked immunosorbent assay (ELISA), can be used to measure the binding specificity of monoclonal antibodies.

Monoclonal antibody-secreting hybridoma cells can be isolated as single clones by limiting dilution procedures and sub-cultured. Suitable culture media include, but are not limited to, Dulbecco's Modified Eagle's Medium, RPMI-1640, and polypeptide-free, polypeptide-reduced, or serum-free media, e.g., Ultra DOMA PF or HL-1, available from Biowhittaker, Walkersville, Md. Alternatively, the hybridoma cells can be grown in vivo as ascites.

Monoclonal antibodies can be isolated and/or purified from a culture medium or ascites fluid by conventional immunoglobulin (Ig) purification procedures including, but not limited to, polypeptide A-SEPHAROSE, hydroxylapatite chromatography, gel electrophoresis, dialysis, ammonium sulfate precipitation, and affinity chromatography.

Monoclonal antibodies can also be produced by recombinant methods such as are described in U.S. Pat. No. 4,166,452. DNA encoding monoclonal antibodies can be isolated and sequenced using conventional procedures, e.g., using oligonucleotide probes that specifically bind to murine heavy and light antibody chain genes, preferably to probe DNA isolated from monoclonal antibody hybridoma cells lines secreting antibodies specific for anti-psychotic drugs.

Antibody fragments which contain specific binding sites for the anti-psychotic drug may also be generated. Such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., Science 256:1270-1281 (1989)). Fab, Fv and ScFv antibody fragments can all be expressed in and secreted from Escherichia coli, allowing for the production of large amounts of these fragments. Alternatively, Fab'-SH fragments can be directly recovered from E. coli and chemically coupled to form F(ab')$_2$ fragments (Carter et al., BioTechnology 10:163-167 (1992)). Other techniques for the production of antibody fragments are known to those skilled in the art. Single chain Fv fragments (scFv) are also envisioned (see U.S. Pat. Nos. 5,761,894 and 5,587,458). Fv and sFv fragments are the only species with intact combining sites that are devoid of constant regions; thus, they are likely to show reduced non-specific binding. The antibody fragment may also be a "linear antibody" e.g., as described in U.S. Pat. No. 5,642,870, for example. Such linear antibody fragments may be monospecific or bispecific.

Assay Kits and Devices

An assay kit (also referred to as a reagent kit) can also be provided comprising an antibody as described above. A representative reagent kit may comprise an antibody that binds to the anti-psychotic drug, aripiprazole, a complex comprising an analog of an anti-psychotic drug or a derivative thereof coupled to a labeling moiety, and may optionally also comprise one or more calibrators comprising a known amount of an anti-psychotic drug or a related standard.

The phrase "assay kit" refers to an assembly of materials and reagents that is used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. An assay kit embodying features of the present invention comprises antibodies which bind aripiprazole. The kit may further comprise competitive binding partners of aripiprazole and calibration and control materials.

The phrase "calibration and control material" refers to any standard or reference material containing a known amount of an analyte. A sample suspected of containing an analyte and the corresponding calibration material are assayed under similar conditions. The concentration of analyte is calculated by comparing the results obtained for the unknown specimen with the results obtained for the standard. This is commonly done by constructing a calibration curve.

Antibodies embodying features of the present invention can be included in a kit, container, pack, or dispenser together with instructions for their utilization. When the antibodies are supplied in a kit, the different components of the immunoassay may be packaged in separate containers and admixed prior to use. Such packaging of the components separately may permit long-term storage without substantially diminishing the functioning of the active components. Furthermore, reagents can be packaged under inert environments, e.g., under a positive pressure of nitrogen gas, argon gas, or the like, which is especially preferred for reagents that are sensitive to air and/or moisture.

Reagents included in kits embodying features of the present invention can be supplied in all manner of containers such that the activities of the different components are substantially preserved while the components themselves are not substantially adsorbed or altered by the materials of the container. Suitable containers include, but are not limited to, ampules, bottles, test tubes, vials, flasks, syringes, envelopes, e.g., foil-lined, and the like. The containers may be comprised of any suitable material including, but not limited to, glass, organic polymers, e.g., polycarbonate, polystyrene, polyethylene, etc., ceramic, metal, e.g., aluminum, metal alloys, e.g., steel, cork, and the like. In addition, the containers may comprise one or more sterile access ports, e.g., for access via a needle, such as may be provided by a septum. Preferred materials for septa include rubber and polytetrafluoroethylene of the type sold under the trade name TEFLON by DuPont (Wilmington, Del.). In addition, the containers may comprise two or more compartments separated by partitions or membranes that can be removed to allow mixing of the components.

Reagent kits embodying features of the present invention may also be supplied with instructional materials. Instructions may be printed, e.g., on paper and/or supplied in an electronically-readable medium. Alternatively, instructions may be provided by directing a user to an internet website, e.g., specified by the manufacturer or distributor of the kit and/or via electronic mail.

The antibody may also be provided as part of an assay device. Such assay devices include lateral flow assay devices. A common type of disposable lateral flow assay device includes a zone or area for receiving the liquid sample, a conjugate zone, and a reaction zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

Another type of assay device is a non-porous assay device having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

In a non-porous assay device, the assay device generally has at least one sample addition zone, at least one conjugate zone, at least one reaction zone, and at least one wicking zone. The zones form a flow path by which sample flows from the sample addition zone to the wicking zone. Also included are capture elements, such as antibodies, in the reaction zone, capable of binding to the analyte, optionally deposited on the device (such as by coating); and a labeled conjugate material also capable of participating in reactions that will enable determination of the concentration of the analyte, deposited on the device in the conjugate zone, wherein the labeled conjugate material carries a label for detection in the reaction zone. The conjugate material is dissolved as the sample flows through the conjugate zone forming a conjugate plume of dissolved labeled conjugate material and sample that flows downstream to the reaction zone. As the conjugate plume flows into the reaction zone, the conjugated material will be captured by the capture elements such as via a complex of conjugated material and analyte (as in a "sandwich" assay) or directly (as in a "competitive" assay). Unbound dissolved conjugate material will be swept past the reaction zone into the at least one wicking zone. Such devices can include projections or micropillars in the flow path.

An instrument such as that disclosed in US Patent Publication Nos. US20060289787A1 and US 20070231883A1, and U.S. Pat. Nos. 7,416,700 and 6,139,800, all of which are incorporated herein by reference in their entireties, is able to detect the bound conjugated material in the reaction zone. Common labels include fluorescent dyes that can be detected by instruments which excite the fluorescent dyes and incorporate a detector capable of detecting the fluorescent dyes.

Immunoassays

The antibodies thus produced can be used in immunoassays to recognize/bind to the anti-psychotic drug, thereby detecting the presence and/or amount of the drug in a patient sample. Preferably, the assay format is a competitive immunoassay format. Such an assay format and other assays are described, among other places, in Hampton et al. (*Serological Methods, A Laboratory Manual*, APS Press, St. Paul, Minn. 1990) and Maddox et al. (*J. Exp. Med.* 158:12111, 1983).

The term "analyte" refers to any substance or group of substances, the presence or amount of which is to be determined. Representative anti-psychotic drug analytes include, but are not limited to, risperidone, paliperidone, olanzapine, aripiprazole, and quetiapine.

The term "competitive binding partner" refers to a substance or group of substances, such as may be employed in a competitive immunoassay, which behave similarly to an analyte with respect to binding affinity to an antibody. Representative competitive binding partners include, but are not limited to, anti-psychotic drug derivatives and the like.

The term "detecting" when used with an analyte refers to any quantitative, semi-quantitative, or qualitative method as well as to all other methods for determining an analyte in general, and an anti-psychotic drug in particular. For example, a method that merely detects the presence or absence of an anti-psychotic drug in a sample lies within the scope of the present invention, as do methods that provide data as to the amount or concentration of the anti-psychotic drug in the sample. The terms "detecting", "determining", "identifying", and the like are used synonymously herein, and all lie within the scope of the present invention.

A preferred embodiment of the subject invention is a competitive immunoassay wherein antibodies which bind the anti-psychotic drug, or the drug or competitive binding partner thereof, are attached to a solid support (such as the reaction zone in a lateral flow assay device) and labeled drug or competitive binding partner thereof, or labeled antibody, respectively, and a sample derived from the host are passed over the solid support and the amount of label detected attached to the solid support can be correlated to a quantity of drug in the sample.

Any sample that is suspected of containing an analyte, e.g., an anti-psychotic drug, can be analyzed in accordance with the methods of the presently preferred embodiments. The sample can be pretreated if desired and can be prepared in any convenient medium that does not interfere with the assay. Preferably, the sample comprises an aqueous medium such as a body fluid from a host, most preferably plasma or serum.

It is to be understood that all manner of immunoassays employing antibodies are contemplated for use in accordance with the presently preferred embodiments, including assays in which antibodies are bound to solid phases and assays in which antibodies are in liquid media. Methods of immunoassays that can be used to detect analytes using antibodies embodying features of the present invention include, but are not limited to, competitive (reagent limited) assays wherein labeled analyte (analyte analog) and analyte in a sample compete for antibodies and single-site immunometric assays wherein the antibody is labeled; and the like.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., *Molecular Cloning: A Laboratory Manual*, 2nd Ed., Cold Spring Harbor Laboratory Press, Cold Spring Harbor, N.Y. (1989).

Copending applications entitled "Haptens of Aripiprazole", U.S. Provisional Patent Appl. No. 61/691,450, filed Aug. 21, 2012, and US 20140163206, filed Aug. 20, 2013), "Haptens of Olanzapine", U.S. Provisional Patent Appl. No. 61/691,454, filed Aug. 21, 2012, and US 20140213766, filed Aug. 20, 2013), "Haptens of Paliperidone", U.S. Provisional Patent Appl. No. 61/691,459, filed Aug. 21, 2012, and US 20140213767, filed Aug. 20, 2013), "Haptens of Quetiapine", U.S. Provisional Patent Appl. No. 61/691,462, filed Aug. 21, 2012, and US 20140221616, filed Aug. 20, 2013), "Haptens of Risperidone and Paliperidone", U.S. Provisional Patent Appl. No. 61/691,469, filed Aug. 21, 2012, and US 20140155585, Aug. 20, 2013), "Antibodies to Aripiprazole Haptens and Use Thereof", U.S. Provisional Patent Appl. No. 61/691,544, filed Aug. 21, 2012, and US 20140057299, filed Aug. 20, 2013), "Antibodies to Olanzapine Haptens and Use Thereof", U.S. Provisional Patent Appl. No. 61/691,572, filed Aug. 21, 2012, US 20140057303, filed Aug. 20, 2013), "Antibodies to Quetiapine Haptens and Use Thereof", U.S. Provisional Patent Appl. No. 61/691,598, filed Aug. 21, 2012, and US 20140057305, filed Aug. 20, 2013), "Antibodies to Risperidone Haptens and Use Thereof", U.S. Provisional Patent Appl. No. 61/691,615, filed Aug. 21, 2012, and US 20140057301, filed Aug. 20, 2013), "Antibodies to Aripiprazole and Use Thereof", U.S. Provisional Patent Appl. No. 61/691,522, filed Aug. 21, 2012, and US 20140031640, filed Aug. 20, 2013), "Antibodies to Olanzapine and Use Thereof", U.S. Provisional Patent Appl. No. 61/691,645, filed Aug. 21, 2012, and US 20140057304, filed Aug. 20, 2013), "Antibodies to Paliperidone and Use Thereof", US Provisional Patent Appl. No. 61/691,692, filed Aug. 21, 2012, and US 20140057298, filed Aug. 20, 2013), "Antibodies to Quetiapine and Use Thereof", U.S. Provisional Patent Appl. No. 61/691,659, filed Aug. 21, 2012, and US 20140057306, filed Aug. 20, 2013), "Antibodies to Risperidone and Use Thereof", U.S. Provisional Patent Appl. No. 61/691,675, filed Aug. 21, 2012, and US 20140057302, filed Aug. 20, 2013), and "Antibodies to Risperidone and Use Thereof", U.S. Provisional Patent Appl. No. 61/790,880, filed Mar. 15, 2013, and US 20140057302, filed Aug. 20, 2013) are all incorporated herein by reference in their entireties.

Example 1

4-(aminomethyl)-7-(4-(4-(2,3-dichlorophenyl)piperazin-1-yl)butoxy)-3,4-dihydroquinolin-2(1H)-one

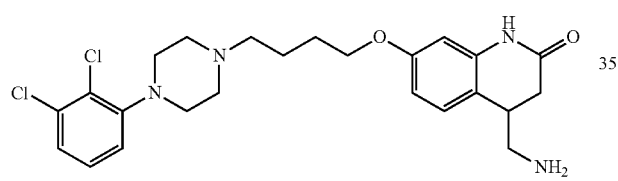

Step A 1-(bromomethyl)-4-methoxy-2-nitrobenzene

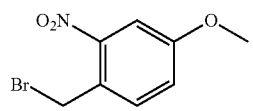

To a well-stirred solution of compound 4-methoxy-1-methyl-2-nitrobenzene (218 g, 1.30 mol) in CCl$_4$ (1500 mL) was added AIBN (21.7 g, 0.13 mol), and NBS (348 g, 1.96 mol). After the reaction mixture was heated at reflux for 16 h under N$_2$, water was added and the product extracted from the aqueous phase with CH$_2$Cl$_2$. The resultant organic phase was washed with brine, dried over Na$_2$SO$_4$ and the solvent was evaporated to give a solid which was purified by silica gel chromatography (eluting with petroleum ether/ethyl acetate, 20:1) to the title compound as a yellow solid. ESI-MS (M+1) 246. $^1$H NMR: (CDCl$_3$, 400 MHz): δ (ppm) 7.55 (s, 1H), 7.46-7.42 (d, 1H), 7.14-7.11 (d, 1H), 4.79 (s, 2H), 3.90 (s, 3H).

Step B 2-(4-methoxy-2-nitrophenyl)acetonitrile

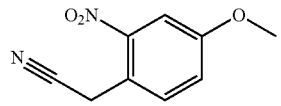

To a stirred solution of 1-(bromomethyl)-4-methoxy-2-nitrobenzene, prepared as described in Step A, (40 g, 0.163 mol) in THF (500 mL) and ETOH (100 mL) was added a solution of KCN (26.6 g, 0.408 mol) in water (100 mL). The reaction mixture was stirred at 0° C. for 1 h and then further for 3 h at room temperature. The reaction mixture was diluted with water (500 mL) and aqueous phase was extracted with DCM (500 mL) and then washed with brine, dried over Na$_2$SO$_4$ and evaporated in vacuo. The residue was purified by chromatography on a silica gel column to give the title compound. ESI-MS (M+1) 193. $^1$H NMR: (CDCl$_3$, 400 MHz): δ (ppm) 7.72 (s, 1H), 7.63-7.61 (d, 1H), 7.26-7.23 (d, 1H), 4.14 (s, 2H), 3.93 (s, 3H).

Step C ethyl 3-cyano-3-(4-methoxy-2-nitrophenyl)propanoate

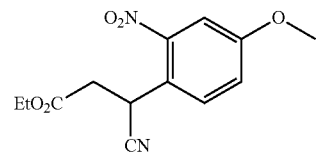 [SMILES: CCOC(=O)CC(C#N)c1ccc(OC)cc1[N+](=O)[O-]]

To a solution of 2-(4-methoxy-2-nitrophenyl)acetonitrile, prepared as described in Step B, (5.5 g, 0.0286 mol) in DMF (100 mL) was added BrCH$_2$CO$_2$Et (5.71 g, 0.034 mol) and K$_2$CO$_3$ (11.86 g, 0.086 mol) at 0° C. The reaction mixture was stirred at 0° C. for 1 h and at room temperature for another 2 h. After the reaction was completed by TLC monitoring, water was added. The reaction was extracted with ethyl acetate; the organic phase was washed with brine, dried over Na$_2$SO$_4$, and concentrated in vacuo. The crude product was purified by chromatography on a silica gel column to give the title compound. ESI-MS (M+1) 279. $^1$H NMR: (CDCl$_3$, 400 MHz): δ (ppm) 7.70-7.68 (d, 1H), 7.57-7.56 (s, 1H), 7.24-7.21 (d, 1H), 5.13-4.98 (m, 1H), 4.20-4.18 (m, 2H), 3.89 (s, 3H), 2.99-2.97 (d, 2H), 1.28-1.24 (t, 3H).

Step D 7-methoxy-2-oxo-1,2,3,4-tetrahydroquinoline-4-carbonitrile

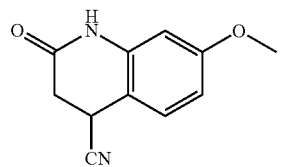

To a solution of ethyl 3-cyano-3-(4-methoxy-2-nitrophenyl)propanoate, prepared as described in Step C, (9.0 g, 0.032 mol) in MeOH (100 mL), Sn (19.3 g, 0.162 mol) was added, followed by hydrochloric acid/MeOH (40 ml, 1:1) all at once. The reaction was stirred at room temperature for 2 h. The solvent was removed in vacuo. Then ethyl acetate was added, and aqueous NaHCO₃ solution was added to neutralize the solution. The organic phase was concentrated to get crude product which was used for next step without further purification.

Step E 4-(aminomethyl)-7-methoxy-3,4-dihydroquinolin-2(1H)-one

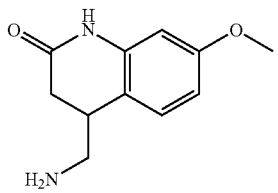

Crude 7-methoxy-2-oxo-1,2,3,4-tetrahydroquinoline-4-carbonitrile, prepared as described in Step D, (6 g, 0.03 mol) and Raney Ni (10 g) was suspended in a mixture of MeOH (100 mL) and 3 mL of triethylamine. The reaction mixture was stirred under H₂ (50 Psi) atmosphere at room temperature for 4 h. After the reaction was completed by monitoring by TLC, the catalyst was filtered off, and then the solvent was removed in vacuo to afford the crude product which was used for next step without further purification.

Step F 4-(aminomethyl)-7-hydroxy-3,4-dihydroquinolin-2(1H)-one

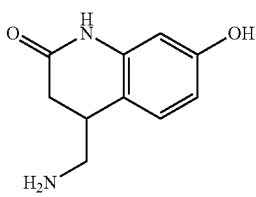 [SMILES: NCC1CC(=O)Nc2cc(O)ccc21]

To a solution of crude 4-(aminomethyl)-7-methoxy-3,4-dihydroquinolin-2(1H)-one, prepared as described in Step E, (8.8 g, 0.0427 mol) in dichloromethane (100 mL), BBr₃ (85 g, 0.342 mol) in dichloromethane (1M) was added dropwise at −14° C., and the reaction was stirred at room temperature overnight. After the reaction was completed by monitoring through TLC, methanol was added slowly at 0° C. to quench the reaction, and the solvent was evaporated in vacuo to get crude product which was used directly in the next step.

Step G tert-butyl ((7-hydroxy-2-oxo-1,2,3,4-tetrahydroquinolin-4-yl)methyl)carbamate

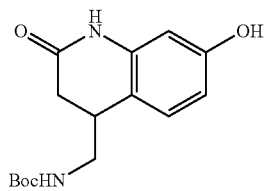 [SMILES: CC(C)(C)OC(=O)NCC1CC(=O)Nc2cc(O)ccc21]

Crude 4-(aminomethyl)-7-hydroxy-3,4-dihydroquinolin-2(1H)-one, prepared as described in Step F, (8.2 g, 0.0427 mol) and (Boc)₂O (4.65 g, 0.021 mol), triethylamine (10 mL) were added to 100 mL of methanol. The reaction was stirred at room temperature for 2 h. After the reaction was stopped, the solvent was removed in vacuo, and ethyl acetate was added. The organic phase was washed with water, aqueous NaHCO₃ solution, dried over Na₂SO₄ and concentrated in vacuo. The crude product was purified by chromatography to give the title compound. ESI-MS (M+1) 292. ¹H NMR: (DMSO-d₆, 400 MHz): δ (ppm) 9.96 (s, 1H), 9.31 (s, 1H), 6.95-6.89 (m, 2H), 6.33 (d, 2H), 3.00-2.97 (m, 2H), 2.90-2.96 (m, 1H), 2.56 (m, 1H), 2.30-2.34 (m, 1H), 1.37 (s, 9H).

Step H tert-butyl ((7-(4-bromobutoxy)-2-oxo-1,2,3,4-tetrahydroquinolin-4-yl)methyl)carbamate

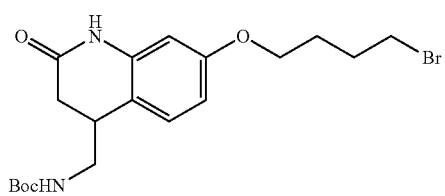 [SMILES: CC(C)(C)OC(=O)NCC1CC(=O)Nc2cc(OCCCCBr)ccc21]

To a solution of tert-butyl ((7-hydroxy-2-oxo-1,2,3,4-tetrahydroquinolin-4-yl)methyl)carbamate, prepared as described in Step H, (1.0 mmol, 292 mg) and 1,4-dibromobutane (1.1 mmol, 237.5 mg) in DMF (1.5 mL) was added anhydrous K₂CO₃ (1.2 mmol, 166 mg). The mixture was stirred at room temperature overnight until HPLC and LC/MS indicated that the reaction was complete to give the title compound, which was subjected to next reaction without purification. MS m/z 428 (MH⁺).

Step I tert-butyl ((7-(4-(4-(2,3-dichlorophenyl)piperazin-1-yl)butoxy)-2-oxo-1,2,3,4-tetrahydroquinolin-4-yl)methyl)carbamate

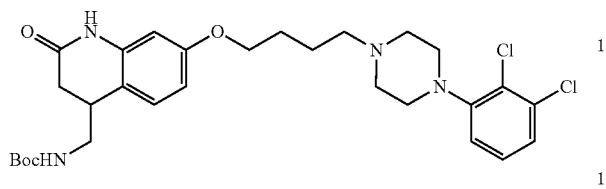

To a solution of tert-butyl ((7-(4-bromobutoxy)-2-oxo-1,2,3,4-tetrahydroquinolin-4-yl)methyl)carbamate, prepared as described in Step H, in DMF was added 1-(2,3-dichlorophenyl)-piperazine hydrochloride (1.0 mmol, 268 mg) and $K_2CO_3$ (1.23 mmol, 170 mg). The mixture was stirred at room temperature overnight. The solvent was evaporated in vacuo and the residue was partitioned between dichloromethane and saturated aqueous $NaHCO_3$ solution. The organic layer was separated and aqueous layer was extracted with additional dichloromethane. Organic layers were combined, concentrated. The residue was then subjected to column chromatography on silica gel with gradient 0-10% methanol in dichloromethane to give the title compound as a solid. MS m/z 578 ($MH^+$).

Step J 4-(aminomethyl)-7-(4-(4-(2,3-dichlorophenyl)piperazin-1-yl)butoxy)-3,4-dihydroquinolin-2(1H)-one

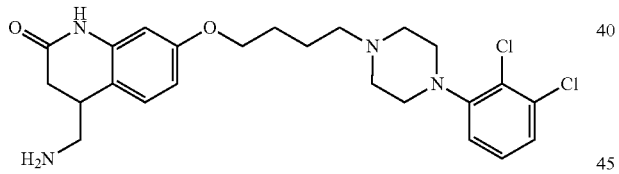

To a solution of tert-butyl ((7-(4-(4-(2,3-dichlorophenyl)piperazin-1-yl)butoxy)-2-oxo-1,2,3,4-tetrahydroquinolin-4-yl)methyl)carbamate, prepared as described in Step I, (200 mg, 0.35 mmol) in dichloromethane (5 mL) was added 1 mL of TFA. The mixture was stirred at room temperature for 2.5 hr. The solvent was evaporated in vacuo and the residue was partitioned between dichloromethane and saturated $NaHCO_3$ solution. The organic layer was separated and aqueous layer was extracted with additional dichloromethane. The organic layers were combined, dried over $Na_2SO_4$, filtered and concentrated. The residue was then subjected to column chromatography on silica gel with 10% methanol in dichloromethane, followed by 10% 7N ammonia methanol in dichloromethane, to give the title compound as a solid. This product was further purified by recrystalization from dichloromethane and heptanes to give final product as a white solid. MS m/z 477 ($MH^+$). $^1$H NMR: ($CDCl_3$, 400 MHz): δ (ppm) 7.40 (s, 1H), 7.25-7.05 (m, 3H), 7.00 (d, 1H), 6.60 (d, 1H), 6.30 (s, 1H), 4.00 (m, 2H), 3.10 (m, 4H), 3.00-2.60 (m, 9H), 2.50 (m, 2H), 1.90-1.40 (m, 6H). Calculated for $C_{24}H_{30}Cl_2N_4O_2$; C, 60.38; H, 6.33; N, 11.74. Found C, 60.32; H, 5.89; N, 11.26.

Example 2

7-(4-(4-(4-amino-2,3-dichlorophenyl)piperazin-1-yl)butoxy)-3,4-dihydroquinolin-2(1H)-one

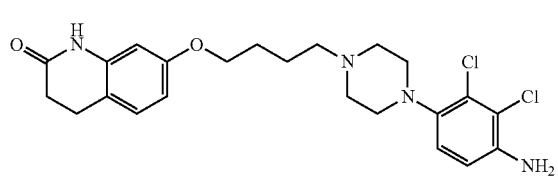 [SMILES: Nc1ccc(N2CCN(CCCCOc3ccc4c(c3)NC(=O)CC4)CC2)c(Cl)c1Cl]

Step A 4-bromo-2,3-dichloro-N-(4-methoxybenzyl)aniline

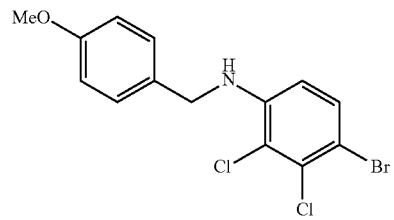 [SMILES: COc1ccc(CNc2ccc(Br)c(Cl)c2Cl)cc1]

To a solution of 4-bromo-2,3-dichloro-phenylamine (3.215 g, 13.3 mmol) and 1-chloromethyl-4-methoxy-benzene (2.297 g, 14.7 mmol) in 23 mL of DMF was added potassium iodide (2.214 g, 13.3 mmol) and 647 mg of sodium hydride (60% oil dispersion). After stirring at room temperature overnight, the reaction mixture was evaporated in vacuo and the residue was partitioned between dichloromethane and saturated $NaHCO_3$ aqueous solution. The organic layer was separated and aqueous layer was extracted with additional dichloromethane. The organic layers were combined, dried over $Na_2SO_4$, filtrated, and concentrated. The residue was then subjected to column chromatography on silica gel with 30% ethyl acetate in heptanes to give the title compound as a yellow solid; MS m/z 362 ($MH^+$).

Step B 2,3-dichloro-N-(4-methoxybenzyl)-4-(piperazin-1-yl)aniline

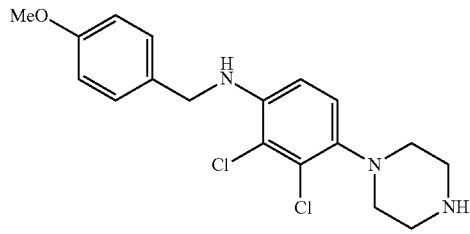 [SMILES: COc1ccc(CNc2ccc(N3CCNCC3)c(Cl)c2Cl)cc1]

A mixture of 4-bromo-2,3-dichloro-N-(4-methoxybenzyl) aniline, prepared as described in the previous step, (3.61 g, 10 mmol), piperizine (1.034 g, 12 mmol), sodium t-butoxide (1.16 g, 12 mmol), and tris(dibenzylideneacetone) dipalladium(0) (180 mg, 2 mol %) in 16 mL of toluene in a sealed thick-wall flask was stirred and heated in an oil bath at 100° C. for 2.5 days. After cooling to room temperature, the reaction mixture was partitioned between dichloromethane and water. The organic layer was separated and aqueous layer was extracted with additional dichloromethane. The organic layers were combined, dried over $Na_2SO_4$, filtered, and concentrated. The residue was purified by column chromatography on silica gel column with 10% methanol in dichloromethane, followed by 10% 7N ammonia methanol in dichloromethane, to give the title compound as a light brown solid. MS m/z 367 (MH+). $^1$H NMR: ($CDCl_3$, 400 MHz): δ (ppm) 7.28 (d, 2H), 6.98 (d, 2H), 6.50 (d, 1H), 4.60 (s, 1H), 4.30 (m, 2H), 3.80 (m, 3H), 3.10-2.85 (m, 8H), 2.30 (s, 1H).

Step C 2,3-dichloro-4-(piperazin-1-yl)aniline

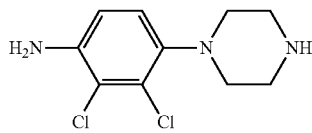 [SMILES: Nc1ccc(N2CCNCC2)c(Cl)c1Cl]

To a solution of 2,3-dichloro-N-(4-methoxybenzyl)-4-(piperazin-1-yl)aniline, prepared as described in the previous step, (562 mg, 1.54 mmol) in dichloromethane (5 mL) was added 5 mL of TFA. The reaction mixture was stirred at room temperature for 5 hr, and then was evaporated in vacuo to dryness. The residue was re-dissolved in dichloromethane and evaporated to dryness. The title compound was used in the next reaction without purification. MS m/z 245 (MH+).

Step D 7-(4-(4-(4-amino-2,3-dichlorophenyl)piperazin-1-yl) butoxy)-3,4-dihydroquinolin-2(1H)-one

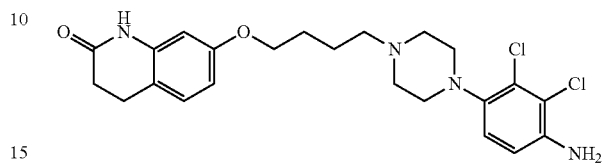

To a solution of 2,3-dichloro-4-(piperazin-1-yl)aniline, prepared as described in the previous step, (1.535 mmol) as TFA salt in DMF (6 mL) was added a solution of commercially available 7-(4-bromo-butoxy)-3,4-dihydro-1H-quinolin-2-one (1.535 mmol) in DMF (1 mL), $K_2CO_3$ (2.121 g), and 1 mL of DMF. The resultant mixture was stirred at room temperature overnight. The solid was filtered and rinsed with dichloromethane. The solution was evaporated in vacuo and the residue was then subjected to column chromatography on silica gel with gradient 0-10% methanol in dichloromethane, followed by 10% 7N ammonia methanol in dichloromethane, to give the title compound as a solid. MS m/z 463 (MH+). $^1$H NMR: (DMSO-$d_6$, 400 MHz): δ (ppm) 10.0 (s, 1H), 7.05 (d, 1H), 6.95 (d, 1H), 6.75 (d, 1H), 6.50 (d, 1H), 6.45 (s, 1H), 5.3 (s, 2H), 3.90 (m, 2H), 2.90-2.70 (m, 6H), 2.50-2.30 (m, 8H), 1.80-1.50 (m, 4H). Calculated for $C_{23}H_{28}Cl_2N_4O_2$ is C, 59.61; H, 6.09; N, 12.09. Found C, 59.44; H, 5.87; N, 11.77.

Example 3

4-((2,3-dichloro-4-(4-(4-((2-oxo-1,2,3,4-tetrahydroquinolin-7-yl)oxy)butyl)piperazin-1-yl)phenyl) amino)-4-oxobutanoic acid

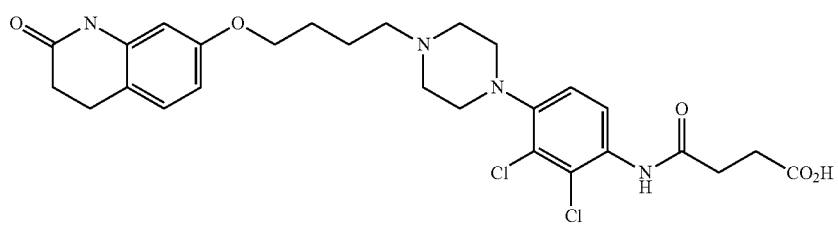 [SMILES: O=C(O)CCC(=O)Nc1ccc(N2CCN(CCCCOc3ccc4c(c3)NC(=O)CC4)CC2)c(Cl)c1Cl]

A solution of Example 2 (115.5 mg, 0.25 mmol) and succinic anhydride (50 mg, 0.5 mmol) in pyridine (1.5 mL) was stirred and heated at 110° C. in a microwave oven for 5.5 hr. The solution was evaporated in vacuo to dryness. The residue was re-dissolved in dichloromethane and evaporated to dryness; and then re-dissolved in methanol and evaporated to dryness. The crude product was purified on a Agela hilic column with gradient 0-20% methanol in dichloromethane to give a solid, which was further purified by recrystalization from methanol and dried at 40-50° C. in a vacuum oven to give the title compound. MS m/z 563 (MH$^+$). $^1$H NMR: (DMSO-d$_6$, 400 MHz): δ (ppm) 12.1 (s, 1H), 10.0 (s, 1H), 9.60 (s, 1H), 7.5 (d, 1H), 7.15 (d, 1H), 7.05 (d, 1H), 6.50 (d, 1H), 6.45 (s, 1H), 3.90 (m, 2H), 3.00 (m, 4H), 2.30 (m, 2H), 2.20-2.30 (m, 12H), 1.80-1.55 (m, 4H). Calculated for C$_{27}$H$_{33}$Cl$_2$N$_4$O$_5$ is C, 57.55; H, 5.72; N, 9.94. Found C, 55.92; H, 5.85; N, 9.58.

Example 4

5-((2,3-dichloro-4-(4-(4-((2-oxo-1,2,3,4-tetrahydroquinolin-7-yl)oxy)butyl)piperazin-1-yl)phenyl)amino)-5-oxopentanoic acid

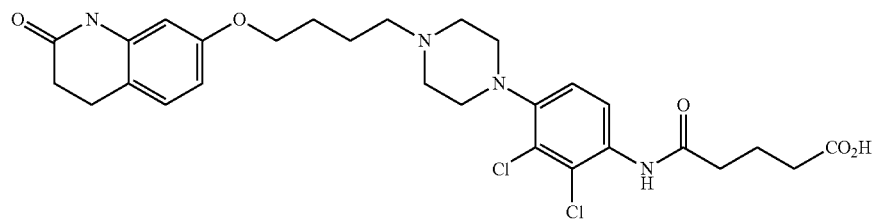 [SMILES: O=C(O)CCCC(=O)Nc1ccc(N2CCN(CCCCOc3ccc4c(c3)NC(=O)CC4)CC2)c(Cl)c1Cl]

A solution of Example 2 (83 mg, 0.18 mmol) and glutaric anhydride (41 mg, 0.36 mmol) in pyridine (1.0 mL) was stirred and heated at 110° C. in a microwave oven for 4.5 hr. The solution was evaporated in vacuo to dryness. The residue was purified on an Agela hilic column (12 g) with gradient 0-30% methanol and dried at 40-50° C. in a vacuum oven to give the title compound. MS m/z 578 (MH$^+$).

Example 5

4-(((7-(4-(4-(2,3-dichlorophenyl)piperazin-1-yl)butoxy)-2-oxo-1,2,3,4-tetrahydroquinolin-4-yl)methyl)amino)-4-oxobutanoic acid

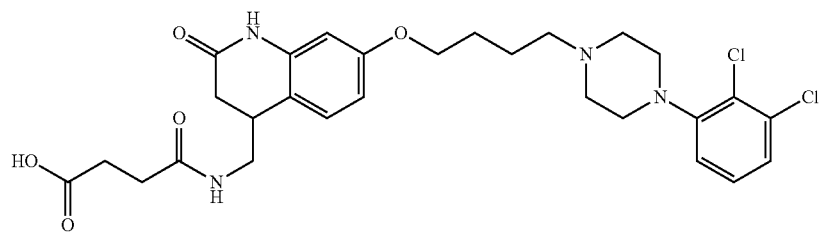 [SMILES: O=C(O)CCC(=O)NCC1CC(=O)Nc2cc(OCCCCN3CCN(c4cccc(Cl)c4Cl)CC3)ccc21]

A solution of Example 1 (24.1 mg, 0.05 mmol) and succinic anhydride (10 mg, 0.10 mmol) in THF (1.0 mL) was stirred at room temperature overnight. The solution was evaporated in vacuo to dryness. The residue was purified on a silica gel column (12 g) with gradient 0-30% methanol in dichloromethane and dried at 40-50° C. in a vacuum oven to give the title compound. MS m/z 578 (MH$^+$).

Example 6

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide

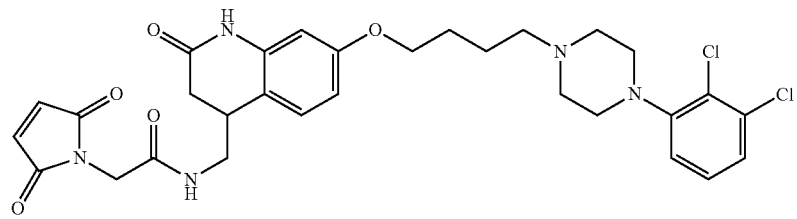 [SMILES: O=C(CN1C(=O)C=CC1=O)NCC1CC(=O)Nc2cc(OCCCCN3CCN(c4cccc(Cl)c4Cl)CC3)ccc21]

To a solution of Example 1 (MW 477.4 2.2 mg, 4.61 μmoles) in 110 μL of DMF and 2.3 μL of tributylamine was added 116 μL of a DMF solution of N-(α-maleimidoacetoxy) succinimide ester (AMAS, MW 252.2, 10 mg/mL, 1.16 mg, 4.61 μmoles). The resulting solution was allowed to stir for 90 minutes at 20° C., and then used as such in conjugation reaction with thiol-activated protein.

Example 7

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide—Keyhole Limpet Hemocyanin Conjugate To 3.23 mL of a solution of keyhole limpet hemocyanin (KLH MW 100,000 14.6 mg, 0.146 μmoles) in 100 mM phosphate buffer, 0.46M sodium chloride, pH 7.4 was added 33.7 μL of a DMF solution of N-Succinimidyl-S-acetylthioacetate (SATA MW 231.2, 25 mg/mL, 0.84 mg, 3.65 μmoles). The resulting solution was incubated at 20° C. for 1 hour on a roller mixer. The reaction was purified on a Sephadex G-25 column using 100 mM phosphate buffer, 0.46M sodium chloride, and 5 mM EDTA, at pH 6.0. To 6.46 mL of the KLH-SATA solution (13.7 mg, 0.137 μmoles) was added 646 μL of 2.5M hydroxylamine, and 50 mM EDTA, at pH 7.0. The resulting solution was incubated at 20° C. for 1 hour on a roller mixer. The reaction was treated with 169.6 μL of N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide solution (prepared as described in example 6) (3.43 μmoles). The resulting cloudy mixture was incubated for 2 hours at 20° C. on a roller mixer. The reaction was filtered through a 0.2 μm syringe filter then purified on a Sephadex G-25 column using 100 mM phosphate buffer and 0.46M sodium chloride at pH 7.4, to give the KLH conjugate of Example 6.

Example 8

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide—Bovine Thyroglobulin Conjugate To 2.14 mL of a solution of bovine thyroglobulin (BTG, MW 660,000, 21.8 mg, 0.033 μmoles) in a 100 mM phosphate buffer at pH 7.5 was added 61.1 μL of a DMF solution of N-succinimidyl-S-acetylthioacetate (SATA, MW 231.2, 25 mg/mL, 1.53 mg, 6.6 μmoles). The resulting solution was incubated at 20° C. for 1 hour on a roller mixer. The reaction was purified on a Sephadex G-25 column using 100 mM phosphate buffer, 5 mM EDTA, at pH 6.0.

To 5.79 mL of BTG-SATA (20.5 mg, 0.031 μmoles) was added 579 μL of 2.5M hydroxylamine, and 50 mM EDTA, at pH 7.0. The resulting solution was incubated at 20° C. for 1 hour on a roller mixer. The reaction was treated with 304.0 μL of N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide solution (prepared as described in example 6) (6.2 μmoles). The resulting cloudy mixture was incubated for 2 hours at 20° C. on a roller mixer. The reaction was filtered through a 0.45 μm syringe filter then purified on a Sephadex G-25 column using 100 mM phosphate buffer and 0.14M sodium chloride at pH 7.4, to give the bovine thyroglobulin conjugate of Example 6.

Example 9

N-((7-(4-(4-(2,3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide—Ovalbumin Conjugate Step A To 1.0 mL of a solution of ovalbumin (MW 44,300, 10.0 mg, 0.23 μmoles) in 100 mM phosphate buffer at pH 7.5 was added 31.3 μL of a DMF solution of N-Succinimidyl-S-acetylthioacetate (SATA, MW 231.2, 25 mg/mL, 0.78 mg, 3.4 μmoles). The resulting solution was incubated at 20° C. for 1 hour on a roller mixer. The reaction was treated with 100 μL of 2.5M hydroxylamine and 50 mM EDTA at pH 7.0. The resulting solution was incubated at 20° C. for 15 minutes on a roller mixer. The reaction was purified on a Sephadex G-25 column using 100 mM phosphate buffer and 5 mM EDTA at pH 6.0.

Step B

To the ovalbumin-SH, (3.1 mL, 8.3 mg, 0.187 μmol), prepared as described in Step A, was added N-((7-(4-(4-(2, 3-dichlorophenyl)piperazin-1-yl)butoxy)-2-oxo-1,2,3,4-tetrahydroquinolin-4-yl)methyl)-2-(2,5-dioxo-2,5-dihydro-1H-pyrrol-1-yl)acetamide solution (prepared as described in example 6) ((185.7 μL, 3.75 μmoles). The resulting cloudy mixture was incubated for 2.5 hours at 20° C. on a roller mixer. The reaction was filtered through a 0.45 μm syringe filter, then purified on a Sephadex G-25 column using 100 mM phosphate buffer, 0.14M sodium chloride at pH 7.4, to give the ovalbumin conjugate of Example 6.

Example 10

Competitive Immunoassay for Aripiprazole and Multiplex Competitive Immunoassay for Aripiprazole, Olanzapine, Quetiapine, and Risperidone Following a series of immunizations with the immunogen having Formula II (compound 6) described above, mouse tail bleeds were tested for reactivity using an ELISA. Hybridoma supernatants were also tested, and the ELISA data shown in Table 8 below shows reactivity of several hybridomas (fusion partner was NSO cells).

TABLE 8

| Dilution | Plate 1 | | | | |
|---|---|---|---|---|---|
| | 1 | 2 | 3 | 4 | 5 |
| 400 | 3C1 | 3D7 | 5C6 | 5C7 | 5H11 |
| 400 | | | | | |
| 1200 | | | | | |
| 1200 | | | | | |
| 3600 | | | | | |
| 3600 | | | | | |
| 10800 | | | | | |
| 10800 | | | | | |
| 400 | 0.8165 | 0.7299 | 0.196 | 3.2953 | 0.0373 |
| 400 | 0.7057 | 0.5671 | 0.1525 | 2.9591 | 0.0371 |
| 1200 | 0.2413 | 0.2186 | 0.0701 | 1.9242 | 0.0348 |
| 1200 | 0.2474 | 0.2278 | 0.0653 | 1.7829 | 0.0336 |
| 3600 | 0.102 | 0.0963 | 0.0472 | 0.739 | 0.0288 |
| 3600 | 0.099 | 0.0954 | 0.051 | 0.7225 | 0.0281 |
| 10800 | 0.0534 | 0.0526 | 0.0381 | 0.2878 | 0.0215 |
| 10800 | 0.0644 | 0.0588 | 0.0411 | 0.2799 | 0.0326 |

Figure 2:
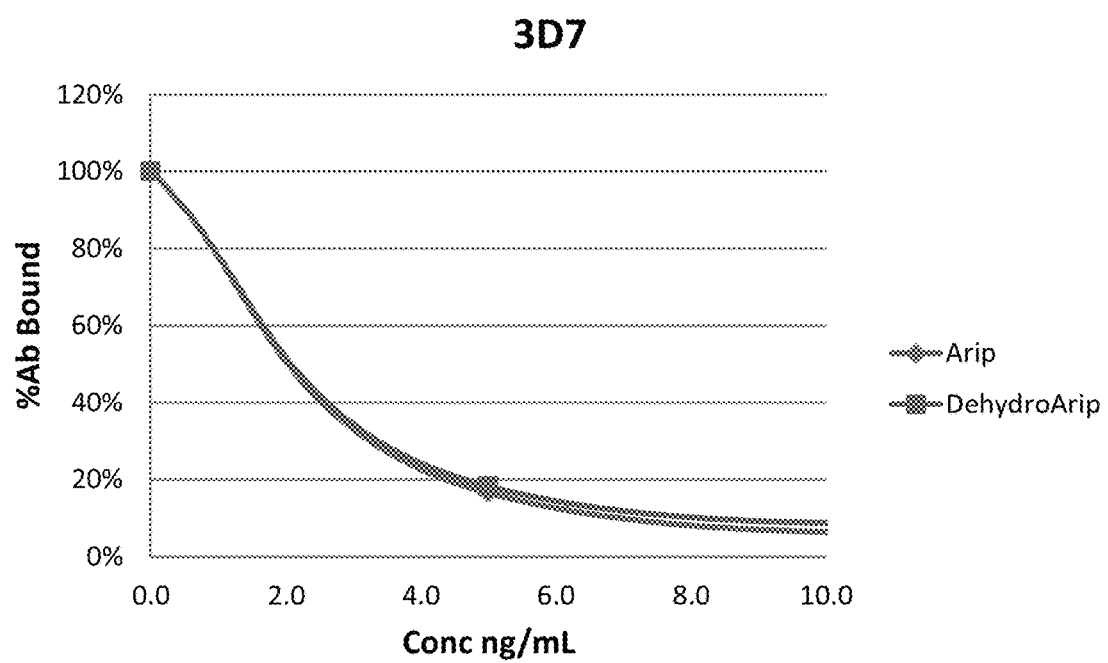
FIG. 2 shows Competitive ELISA results generated with hybridoma 3D7.

Supernatant was then tested by competition ELISA to determine if the signal was specific to either aripiprazole or dehydroaripiprazole. FIGS. 1 and 2 show the results from two representative hybridomas, 3C1 and 3D7. Data shows reactivity to both aripiprazole and dehydroaripiprazole.

Figure 3:
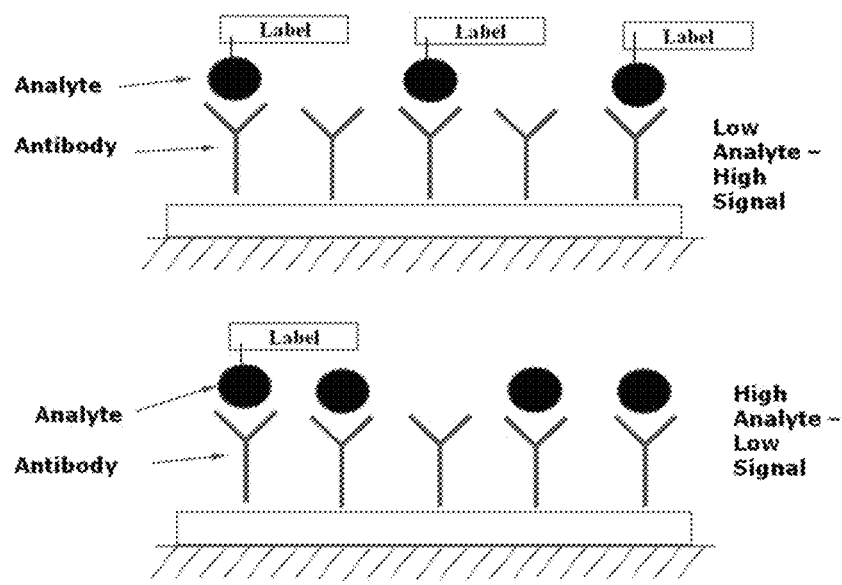
FIG. 3 shows the competitive immunoassay format used on a lateral flow assay device.

FIG. 3 shows the competitive immunoassay format used on a lateral flow assay device in which the capture antibody, aripiprazole clone 5C7, was deposited on a chip along with a detection conjugate consisting of aripiprazole conjugated to a fluorophore. In this competitive format as show in FIG. 3, a low level of analyte (aripiprazole) results in high signal, whereas a high level of analyte (aripiprazole) results in low signal.

Figure 4:
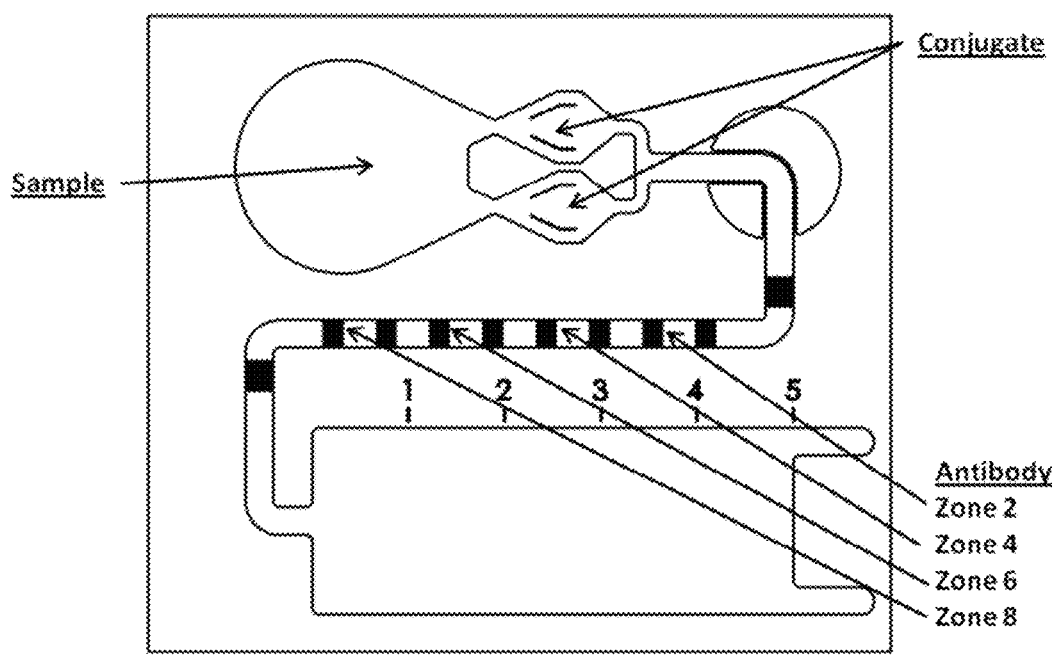
FIG. 4 shows the chip design of a lateral flow assay device according to the subject invention.
Figure 5:
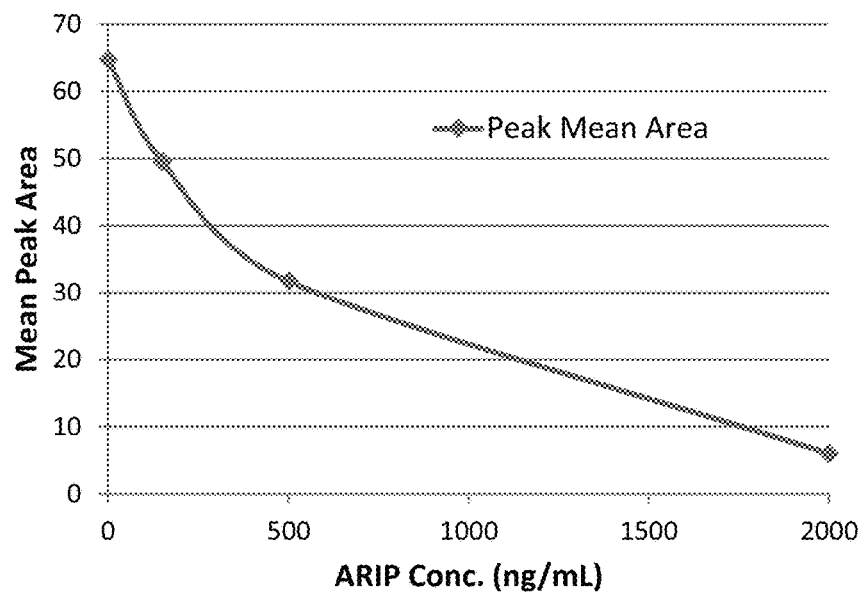
FIG. 5 shows a typical dose response curve for an aripiprazole positive control generated with antibody 5C7 and a labeled aripiprazole competitive binding partner.
Figure 6:
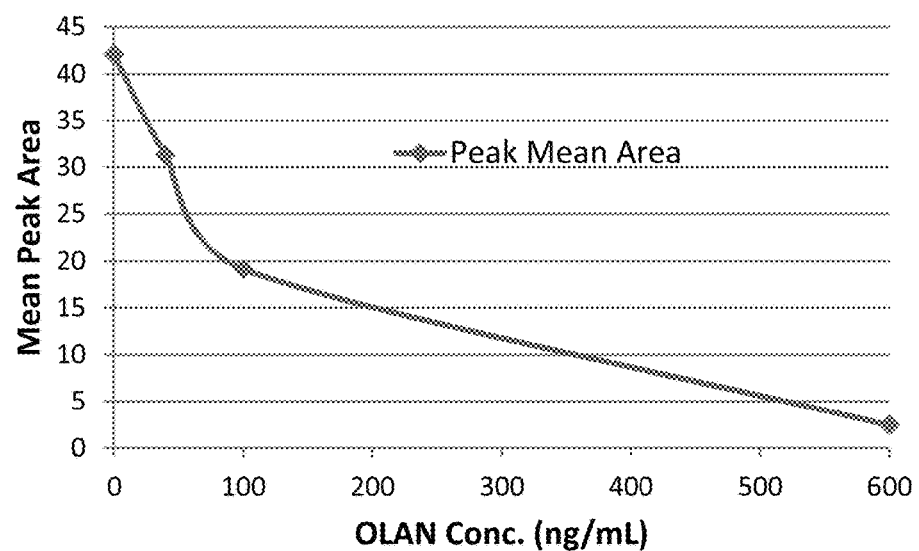
FIG. 6 shows a typical dose response curve for an olanzapine positive control generated with antibody 4G9-1 and a labeled olanzapine competitive binding partner.
Figure 7:
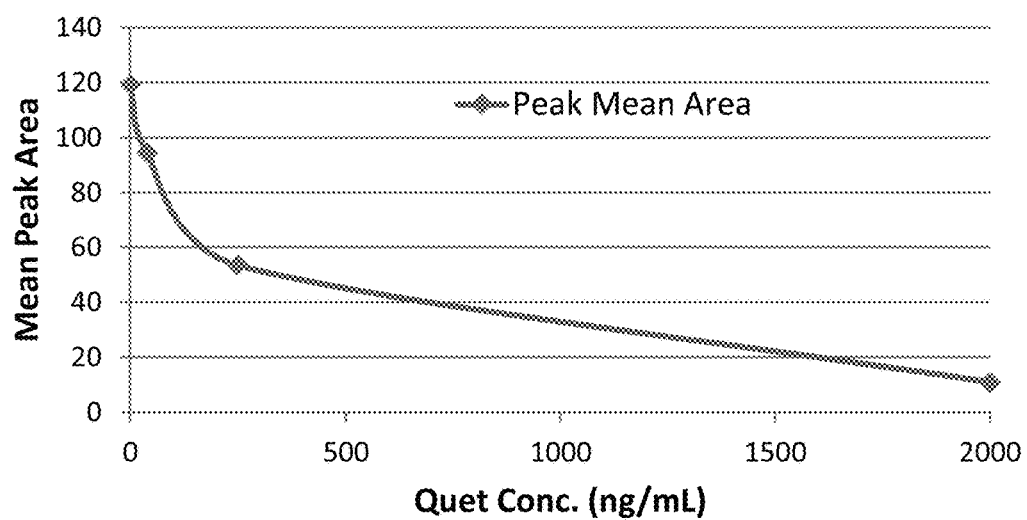
FIG. 7 shows a typical dose response curve for a quetiapine positive control generated with antibody 11 and a labeled quetiapine competitive binding partner.

FIG. 4 shows the chip design of a lateral flow assay device according to one embodiment of the subject invention. The device includes a zone or area for receiving the sample, a conjugate zone (which contains desired labeled competitive binding partner(s)), and a reaction zone (eight areas within the reaction zone are indicated; each area can contain a separate desired antibody). Sample flows from the sample zone through the conjugate zone and to the reaction zone.

Figure 8:
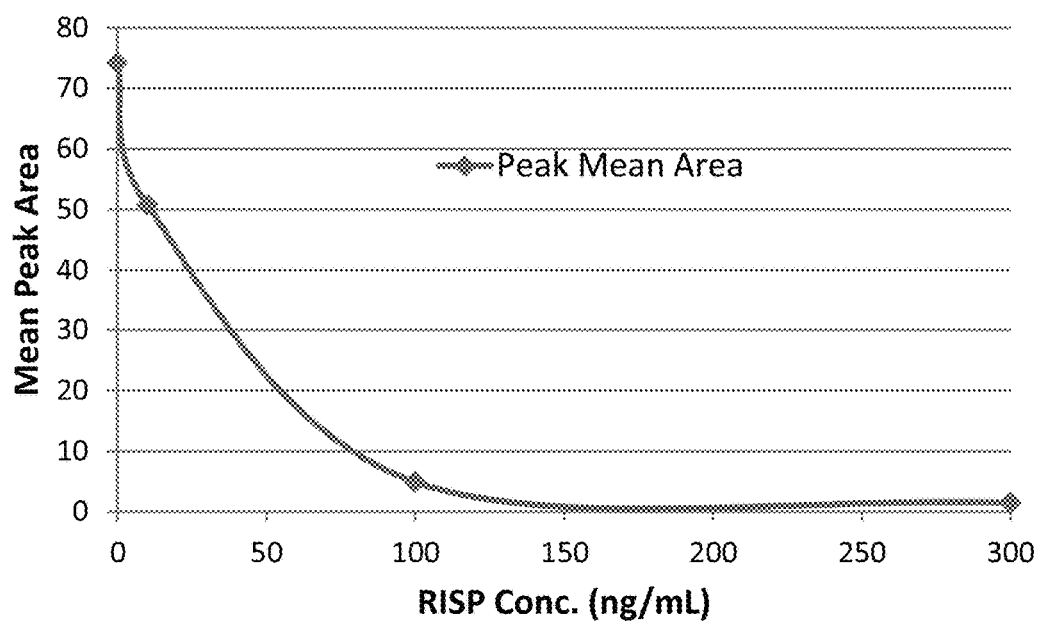
FIG. 8 shows a typical dose response curve for a risperidone positive control generated with antibody 5-9 and a labeled risperidone competitive binding partner.

FIGS. 5-8 show typical dose response curves for an aripiprazole positive control (sample containing aripiprazole) generated with antibody 5C7 deposited in reaction zone 2 and a labeled aripiprazole competitive binding partner in the conjugate zone (FIG. 5), an olanzapine positive control (sample containing olanzapine) generated with antibody 4G9-1 deposited in reaction zone 4 and a labeled olanzapine competitive binding partner in the conjugate zone (FIG. 6), a quetiapine positive control (sample containing quetiapine) generated with antibody 11 deposited in reaction zone 6 and a labeled quetiapine competitive binding partner in the conjugate zone (FIG. 7), and a risperidone positive control (sample containing risperidone) generated with antibody 5-9 deposited in reaction zone 8 and a labeled risperidone competitive binding partner in the conjugate zone (FIG. 8). The labeled competitive binding partners in the conjugate zone compete with the drugs present in the samples for binding to the antibodies. The amount of label is detected and is an indication of the amount of drug present in the sample (the amount of signal being inversely proportional to the amount of drug in the sample—see FIG. 3).

In order to confirm that conjugates of labeled competitive binding partners do not bind to antibodies deposited in the reaction zones, negative controls were conducted by using samples containing no drugs. Referring to Table 9, a sample containing no aripiprazole is deposited in the sample zone and moves by capillary action through the conjugate zone (this time containing labeled olanzapine, labeled quetiapine, and labeled risperidone, but no labeled aripiprazole) and to the reaction zone. The reaction zone again contains aripiprazole antibody (5C7) in reaction zone 2. Table 9 below shows the results, confirming that there is no dose response and the olanzapine, quetiapine, and risperidone conjugates that move by capillary action through the reaction zone do not bind to the aripiprazole antibody.

TABLE 9

| Aripiprazole-Clone 5C7-Math Model 1 (0 ng/mL Conc.) | | | | | | |
|---|---|---|---|---|---|---|
| Assay-MM | Conj | Reaction Zone | Read Position | Peak Mean Area | Peak Heigh | Mean Background |
| ARIP-MM1 | OLAN, QUET, RISP | ARIP | 2 | 0.77 | 1.56 | 3.99 |
| ARIP-MM1 | OLAN, QUET, RISP | | 4 | −0.02 | 0.06 | 4.14 |
| ARIP-MM1 | OLAN, QUET, RISP | | 6 | 0.09 | 0.10 | 4.29 |
| ARIP-MM1 | OLAN, QUET, RISP | | 8 | 0.13 | 0.12 | 4.61 |

Other Conjugates do not bind to Aripiprazole

Referring to Table 10, a sample containing no olanzapine is deposited in the sample zone and moves by capillary action through the conjugate zone (this time containing labeled aripiprazole, labeled quetiapine, and labeled risperidone, but no labeled olanzapine) and to the reaction zone. The reaction zone again contains olanzapine antibody (4G9-1) in reaction zone 4. Table 10 below shows the results, confirming that there is no dose response and the aripiprazole, quetiapine, and risperidone conjugates that move by capillary action through the reaction zone do not bind to the olanzapine antibody.

TABLE 10

OLAN-Clone 4G9-1-Math Model 1 (0 ng/mL Conc.)

| Assay-MM | Conj | Reaction Zone | Read Position | Peak Mean Area | Peak Mean Height | Mean Background |
|---|---|---|---|---|---|---|
| OLAN-MM1 | ARIP, QUET, RISP | | 2 | −0.03 | 0.05 | 4.38 |
| OLAN-MM1 | ARIP, QUET, RISP | OLAN | 4 | 0.74 | 1.10 | 4.56 |
| OLAN-MM1 | ARIP, QUET, RISP | | 6 | 0.06 | 0.09 | 4.79 |
| OLAN-MM1 | ARIP, QUET, RISP | | 8 | 0.11 | 0.13 | 5.17 |

Other Conjugates do not bind to Olanzapine

Referring to Table 11, a sample containing no quetiapine is deposited in the sample zone and moves by capillary action through the conjugate zone (this time containing labeled aripiprazole, labeled olanzapine, and labeled risperidone, but no labeled quetiapine) and to the reaction zone. The reaction zone again contains quetiapine antibody (11) in reaction zone 6. Table 11 below shows the results, confirming that there is no dose response and the aripiprazole, olanzapine, and risperidone conjugates that move by capillary action through the reaction zone do not bind to the quetiapine antibody.

TABLE 11

Quetiapine-Clone 11-Math Model 1 (0 ng/mL Conc.)

| Assay-MM | Conj | Reaction Zone | Read Position | Peak Mean Area | Peak Mean Height | Mean Background |
|---|---|---|---|---|---|---|
| QUET-MM1 | ARIP, OLAN, RISP | | 2 | −0.01 | 0.07 | 3.85 |
| QUET-MM1 | ARIP, OLAN, RISP | | 4 | 0.01 | 0.12 | 4.01 |
| QUET-MM1 | ARIP, OLAN, RISP | QUET | 6 | 0.03 | 0.08 | 4.24 |
| QUET-MM1 | ARIP, OLAN, RISP | | 8 | 0.04 | 0.07 | 4.56 |

Other Conjugates do not bind to Quetiapine

Referring to Table 12, a sample containing no risperidone is deposited in the sample zone and moves by capillary action through the conjugate zone (this time containing labeled aripiprazole, labeled olanzapine, and labeled quetiapine, but no labeled risperidone) and to the reaction zone. The reaction zone again contains risperidone antibody (5-9) in reaction zone 8. Table 12 below shows the results, confirming that there is no dose response and the aripiprazole, olanzapine, and quetiapine conjugates that move by capillary action through the reaction zone do not bind to the risperidone antibody.

TABLE 12

Risperidone-Clone 5-9-Math Model 1 (0 ng/mL Conc.)

| Assay-MM | Conj | Reaction Zone | Read Position | Peak Mean Area | Peak Mean Height | Mean Background |
|---|---|---|---|---|---|---|
| RISP-MM1 | ARIP, OLAN, QUET | | 2 | 0.02 | 0.11 | 7.43 |
| RISP-MM1 | ARIP, OLAN, QUET | | 4 | 0.05 | 0.14 | 7.73 |
| RISP-MM1 | ARIP, OLAN, QUET | | 6 | 0.20 | 0.19 | 8.11 |
| RISP-MM1 | ARIP, OLAN, QUET | RISP | 8 | 1.97 | 3.23 | 8.85 |

Other Conjugates do not bind to Risperidone

In order to confirm that conjugates of labeled competitive binding partners bind only to their respective antibodies deposited in the reaction zones, additional negative controls were conducted by again using samples containing no drugs. Referring to Table 13, a sample containing no aripiprazole is deposited in the sample zone and moves by capillary action through the conjugate zone (this time containing labeled aripiprazole) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 13 below shows the results, confirming that there is no dose response except to the aripiprazole antibody 5C7 (in reaction zone 2).

TABLE 13

Aripiprazole-Clone 5C7-Math Model 1 (0 ng/mL Conc.)

| Assay-MM | Conj | Reaction Zone | Read Position | Peak Mean Area | Peak Mean Height | Mean Background |
|---|---|---|---|---|---|---|
| ARIP-MM1 | ARIP, OLAN, QUET, RISP | ARIP | 2 | 60.34 | 97.53 | 5.44 |
| ARIP-MM1 | ARIP, OLAN, QUET, RISP | | 4 | 2.86 | 3.91 | 11.66 |
| ARIP-MM1 | ARIP, OLAN, QUET, RISP | | 6 | 1.12 | 1.23 | 11.03 |
| ARIP-MM1 | ARIP, OLAN, QUET, RISP | | 8 | 3.14 | 4.19 | 12.94 |

Only the Aripiprazole Reaction Zone is binding

Referring to Table 14, a sample containing no olanzapine is deposited in the sample zone and moves by capillary action through the conjugate zone (this time containing labeled olanzapine) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 14 below shows the results, confirming that there is no dose response except to the olanzapine antibody 4G9-1 (in reaction zone 4).

TABLE 14

OLAN-Clone 4G9-1-Math Model 1 (0 ng/mL Conc.)

| Assay-MM | Conj | Reaction Zone | Read Position | Peak Mean Area | Peak Mean Height | Mean Background |
|---|---|---|---|---|---|---|
| OLAN-MM1 | ARIP, OLAN, QUET, RISP | | 2 | 0.02 | 0.08 | 4.86 |
| OLAN-MM1 | ARIP, OLAN, QUET, RISP | OLAN | 4 | 34.23 | 51.80 | 5.39 |
| OLAN-MM1 | ARIP, OLAN, QUET, RISP | | 6 | 0.22 | 0.32 | 5.39 |
| OLAN-MM1 | ARIP, OLAN, QUET, RISP | | 8 | 0.15 | 0.17 | 5.59 |

Only the Olanzapine Reaction Zone is binding

Referring to Table 15, a sample containing no quetiapine is deposited in the sample zone and moves by capillary action through the conjugate zone (this time containing labeled quetiapine) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 15 below shows the results, confirming that there is no dose response except to the quetiapine antibody 11 (in reaction zone 6).

TABLE 15

Quetiapine-Clone 11-Math Model 1 (0 ng/mL Conc.)

| Assay-MM | Conj | Reaction Zone | Read Position | Peak Mean Area | Peak Mean Height | Mean Background |
|---|---|---|---|---|---|---|
| QUET-MM1 | ARIP, OLAN, QUET, RISP | | 2 | 0.13 | 0.41 | 10.02 |
| QUET-MM1 | ARIP, OLAN, QUET, RISP | | 4 | 0.08 | 0.23 | 10.47 |
| QUET-MM1 | ARIP, OLAN, QUET, RISP | QUET | 6 | 140.35 | 181.33 | 7.91 |
| QUET-MM1 | ARIP, OLAN, QUET, RISP | | 8 | 1.58 | 2.61 | 11.53 |

Only the Quetiapine Reaction Zone is binding

Referring to Table 16, a sample containing no risperidone is deposited in the sample zone and moves by capillary action through the conjugate zone (this time containing labeled risperidone) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 16 below shows the results, confirming that there is no dose response except to the risperidone antibody 5-9 (in reaction zone 8).

TABLE 16

Risperidone-Clone 5-9-Math Model 1 (0 ng/mL Conc.)

| Assay-MM | Conj | Reaction Zone | Read Position | Peak Mean Area | Peak Mean Height | Mean Background |
|---|---|---|---|---|---|---|
| RISP-MM1 | ARIP, OLAN, QUET, RISP | | 2 | 1.03 | 1.51 | 9.07 |
| RISP-MM1 | ARIP, OLAN, QUET, RISP | | 4 | 0.65 | 0.91 | 9.60 |
| RISP-MM1 | ARIP, OLAN, QUET, RISP | | 6 | 2.61 | 6.39 | 10.48 |
| RISP-MM1 | ARIP, OLAN, QUET, RISP | RISP | 8 | 55.98 | 100.91 | 11.58 |

Only the Risperidone Reaction Zone is binding

The results shown above confirm that conjugates of labeled competitive binding partners bind only to their respective antibodies in the reaction zone.

Figure 9:
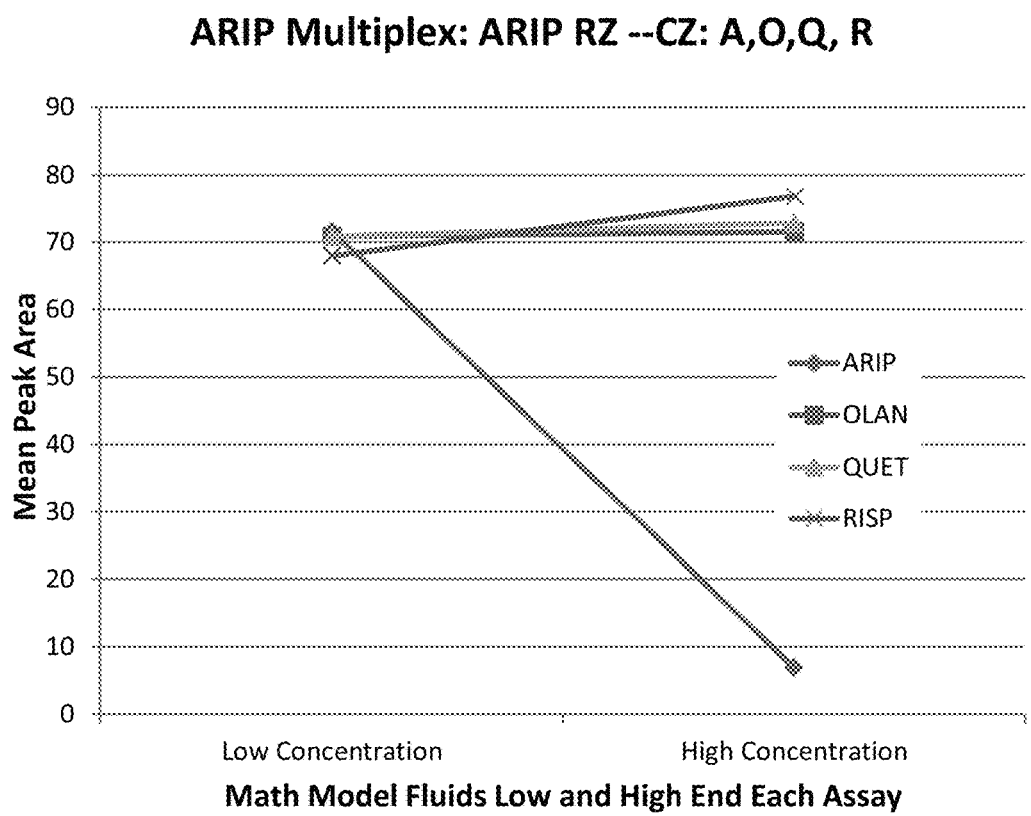
FIG. 9 shows a typical dose response curve for a sample containing aripiprazole generated with aripiprazole antibody 5C7 in the presence of labeled aripiprazole competitive binding partner, with no dose response curve for olanzapine, quetiapine, or risperidone in the presence of a labeled competitive binding partner for each.

FIGS. 9-12 show typical dose response curves in specific antibody reaction zones, and proof of dose response low/high concentration for each specific assay in the presence of other conjugates. In FIG. 9, a sample containing aripiprazole is deposited in the sample zone and moves by capillary action through the conjugate zone (this time containing labeled aripiprazole, labeled olanzapine, labeled quetiapine, and labeled risperidone) and to the reaction zone. The reaction zone again contains aripiprazole antibody (5C7) in reaction zone 2. A typical dose response curve was generated as is shown in FIG. 9 only for aripiprazole, and not for olanzapine, quetiapine, or risperidone.

Figure 10:
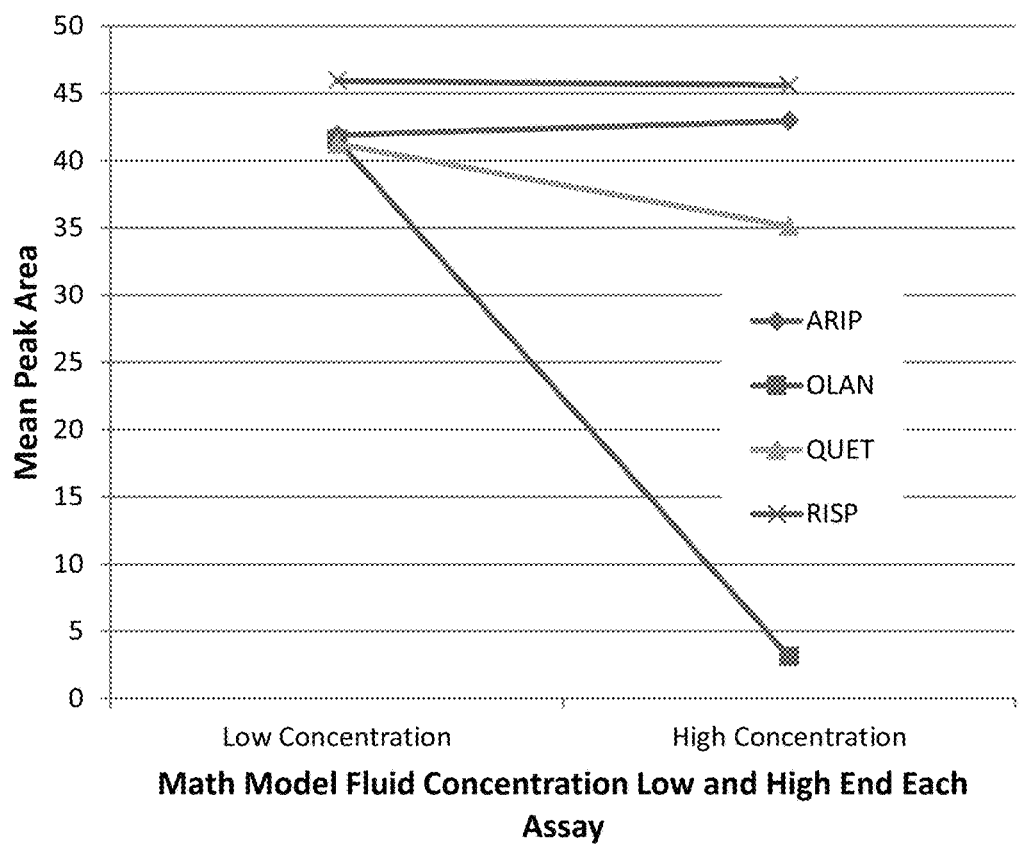
FIG. 10 shows a typical dose response curve for a sample containing olanzapine generated with olanzapine antibody 4G9-1 in the presence of a labeled olanzapine competitive binding partner, with no dose response curve for aripiprazole, quetiapine, or risperidone in the presence of a labeled competitive binding partner for each.

In FIG. 10, a sample containing olanzapine is deposited in the sample zone and moves by capillary action through the conjugate zone (this time containing labeled aripiprazole, labeled olanzapine, labeled quetiapine, and labeled risperidone) and to the reaction zone. The reaction zone again contains olanzapine antibody (4G9-1) in reaction zone 4. A typical dose response curve was generated as is shown in FIG. 10 only for olanzapine, and not for aripiprazole, quetiapine, or risperidone.

Figure 11:
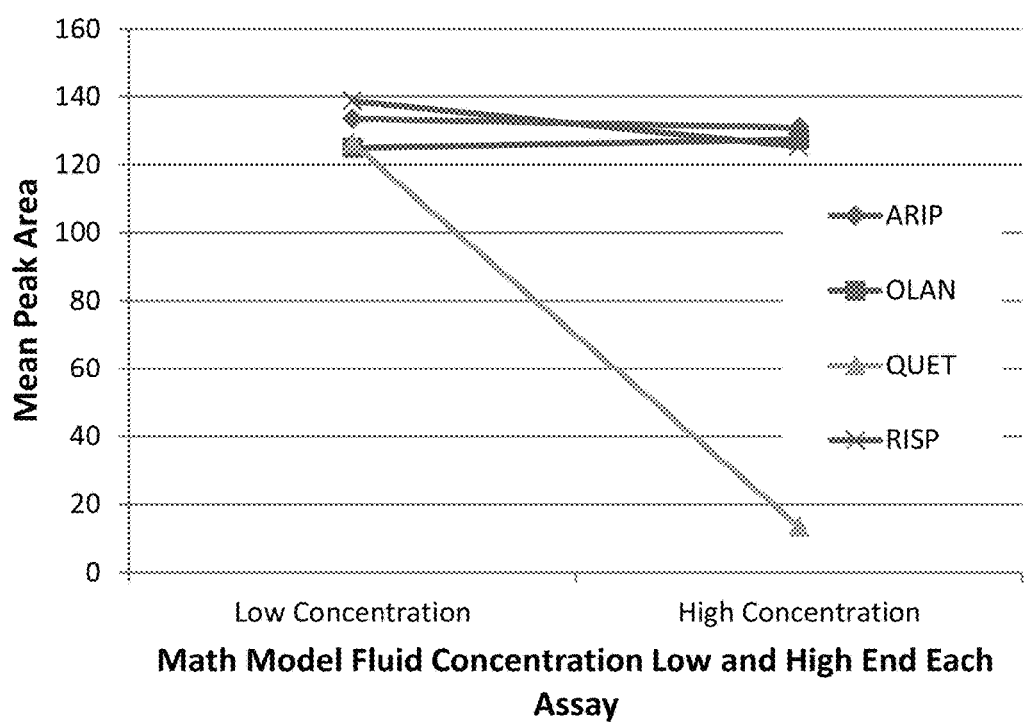
FIG. 11 shows a typical dose response curve for a sample containing quetiapine generated with quetiapine antibody 11 in the presence of a labeled quetiapine competitive binding partner, with no dose response curve for aripiprazole, olanzapine, or risperidone in the presence of a labeled competitive binding partner for each.

In FIG. 11, a sample containing quetiapine is deposited in the sample zone and moves by capillary action through the conjugate zone (this time containing labeled aripiprazole, labeled olanzapine, labeled quetiapine, and labeled risperidone) and to the reaction zone. The reaction zone again contains quetiapine antibody (11) in reaction zone 6. A typical dose response curve was generated as is shown in FIG. 10 only for quetiapine, and not for aripiprazole, olanzapine, or risperidone.

Figure 12:
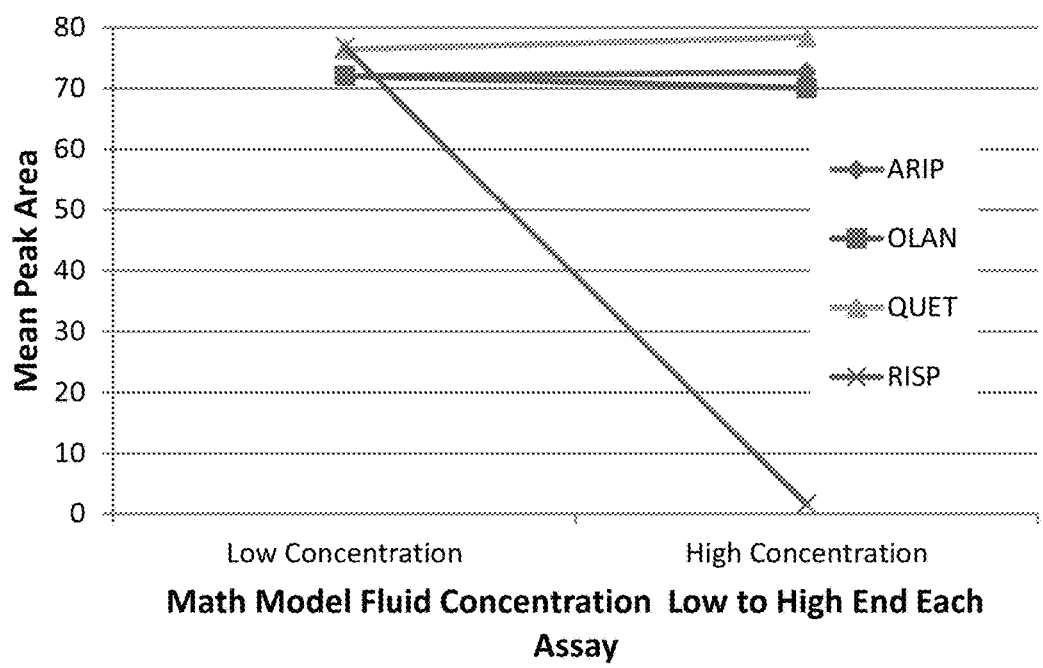
FIG. 12 shows a typical dose response curve for a sample containing risperidone generated with risperidone antibody 5-9 in the presence of a labeled risperidone competitive binding partner, with no dose response curve for aripiprazole, olanzapine, or quetiapine in the presence of a labeled competitive binding partner for each.

In FIG. 12, a sample containing risperidone is deposited in the sample zone and moves by capillary action through the conjugate zone (this time containing labeled aripiprazole, labeled olanzapine, labeled quetiapine, and labeled risperidone) and to the reaction zone. The reaction zone again contains risperidone antibody (5-9) in reaction zone 8. A typical dose response curve was generated as is shown in FIG. 12 only for risperidone, and not for aripiprazole, olanzapine, or quetiapine.

Figure 13:
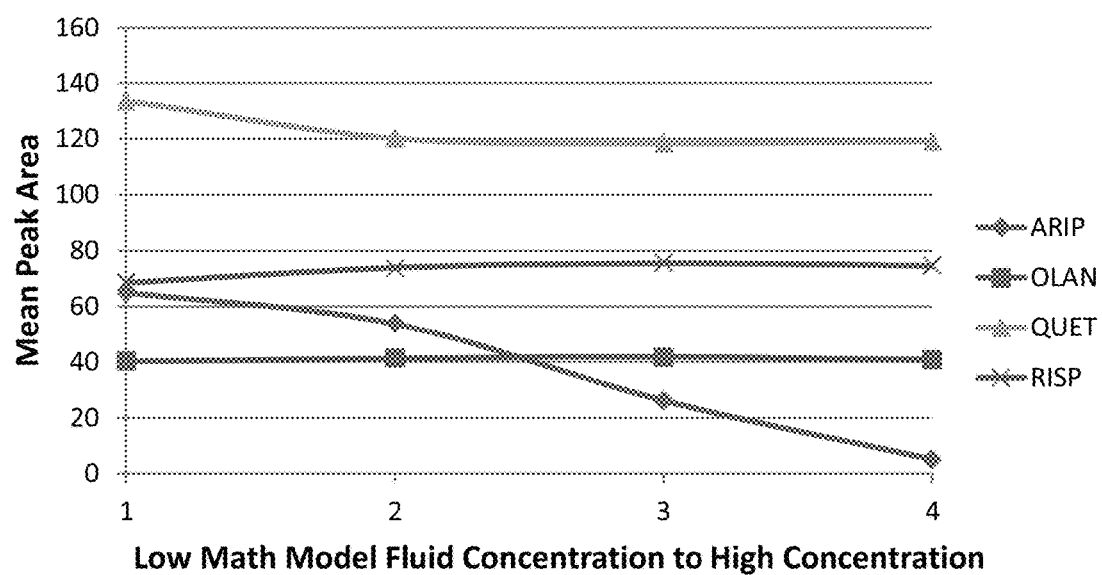
FIG. 13 shows a typical dose response curve for a sample containing aripiprazole generated with aripiprazole antibody 5C7 in the presence of a labeled aripiprazole competitive binding partner, with no dose response curve for olanzapine, quetiapine, or risperidone in the presence of antibody and labeled competitive binding partner for each.
Figure 14:
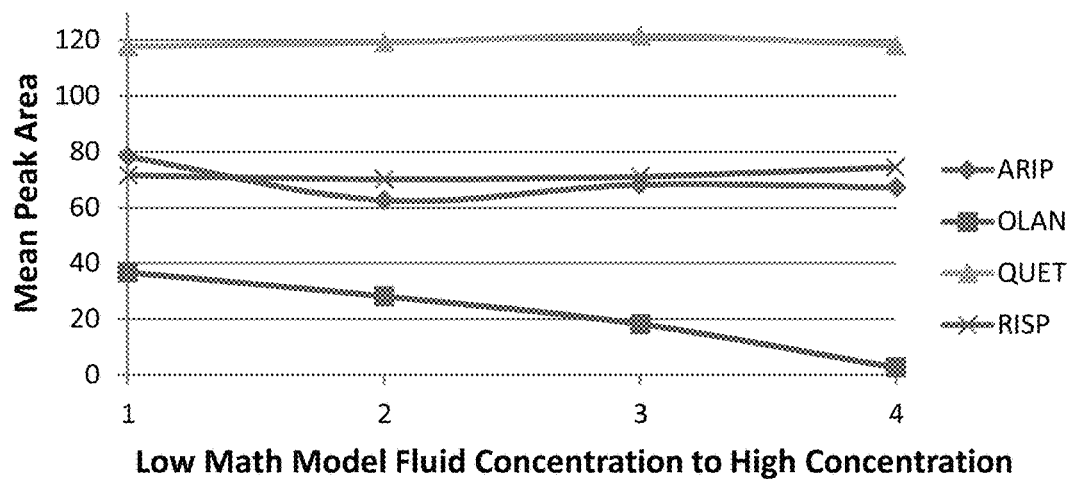
FIG. 14 shows a typical dose response curve for a sample containing olanzapine generated with olanzapine antibody 4G9-1 in the presence of a labeled olanzapine competitive binding partner, with no dose response curve for aripiprazole, quetiapine, or risperidone in the presence of antibody and labeled competitive binding partner for each.
Figure 15:
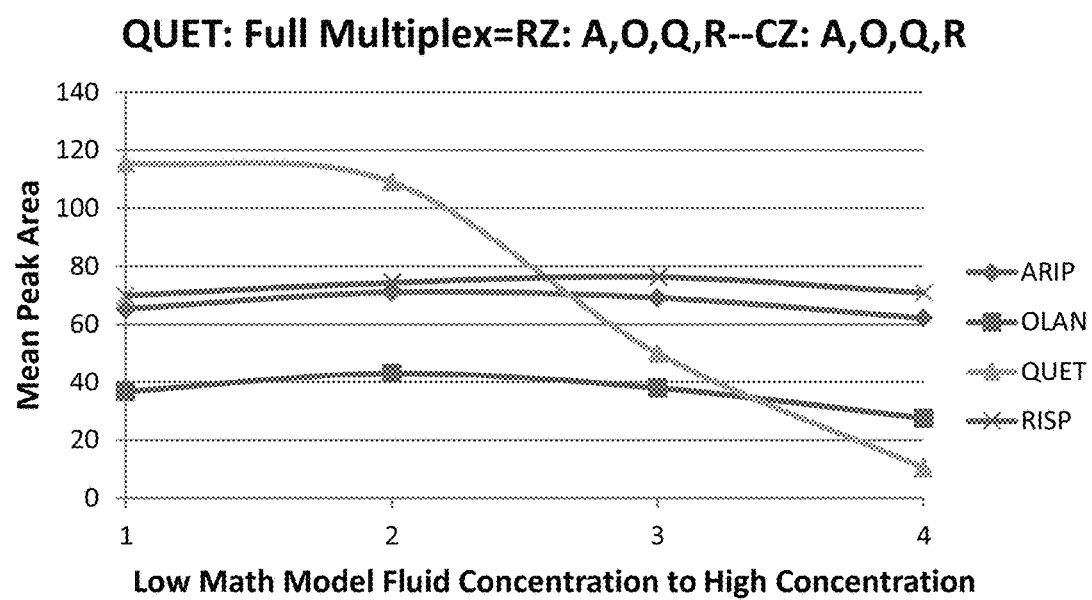
FIG. 15 shows a typical dose response curve for a sample containing quetiapine generated with quetiapine antibody 11 in the presence of labeled quetiapine competitive binding partner, with no dose response curve for aripiprazole, olanzapine, or risperidone in the presence of antibody and labeled competitive binding partner for each.
Figure 16:
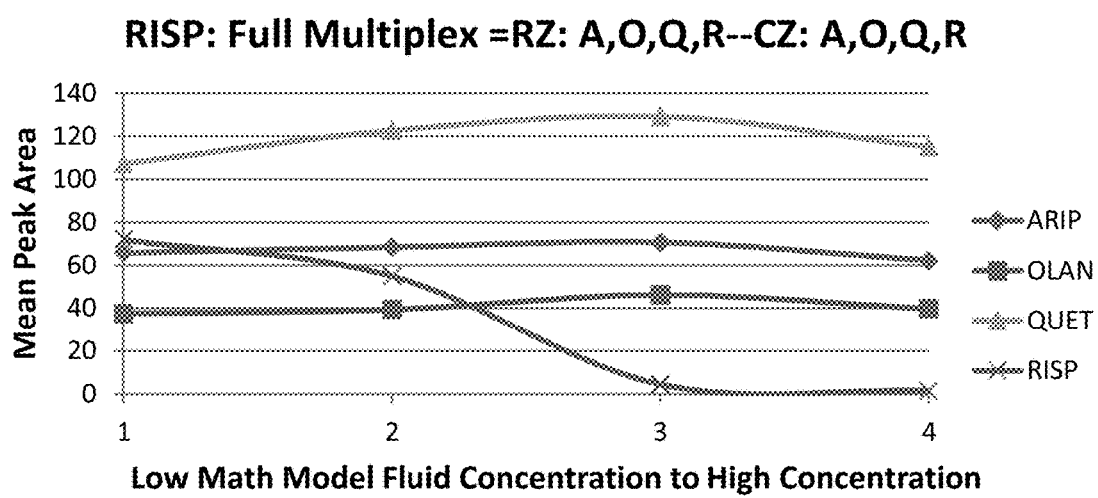
FIG. 16 shows a typical dose response curve for a sample containing risperidone generated with risperidone antibody 5-9 in the presence of a labeled risperidone competitive binding partner, with no dose response curve for aripiprazole, olanzapine, or quetiapine in the presence of antibody and labeled competitive binding partner for each.

FIGS. 13-16 show typical dose response curves for each assay in the presence of other conjugates and antibodies. In FIG. 13, a sample containing aripiprazole is deposited in the sample zone and moves by capillary action through the conjugate zone (again containing labeled aripiprazole, labeled olanzapine, labeled quetiapine, and labeled risperidone) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. A typical dose response curve was generated for aripiprazole, as is shown in FIG. 13. When a sample containing olanzapine was deposited in the sample zone of this chip, a typical dose response curve was generated for olanzapine as shown in FIG. 14. When a sample containing quetiapine was deposited in the sample zone of this chip, a typical dose response curve for quetiapine was generated as shown in FIG. 15. When a sample containing risperidone was deposited in the sample zone of this chip, a typical dose response curve for risperidone was generated as shown in FIG. 16.

Figure 17:
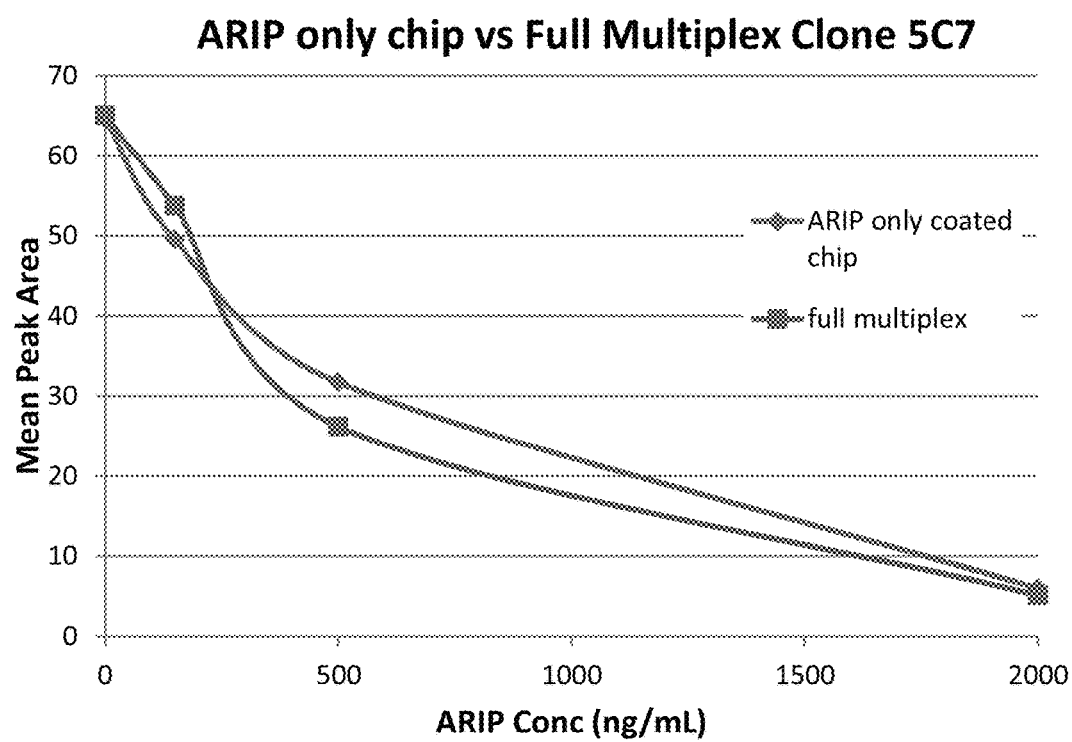
FIG. 17 shows a comparison of the aripiprazole dose response curve generated as a positive control to the aripiprazole dose response curve generated in the multiplex format.
Figure 18:
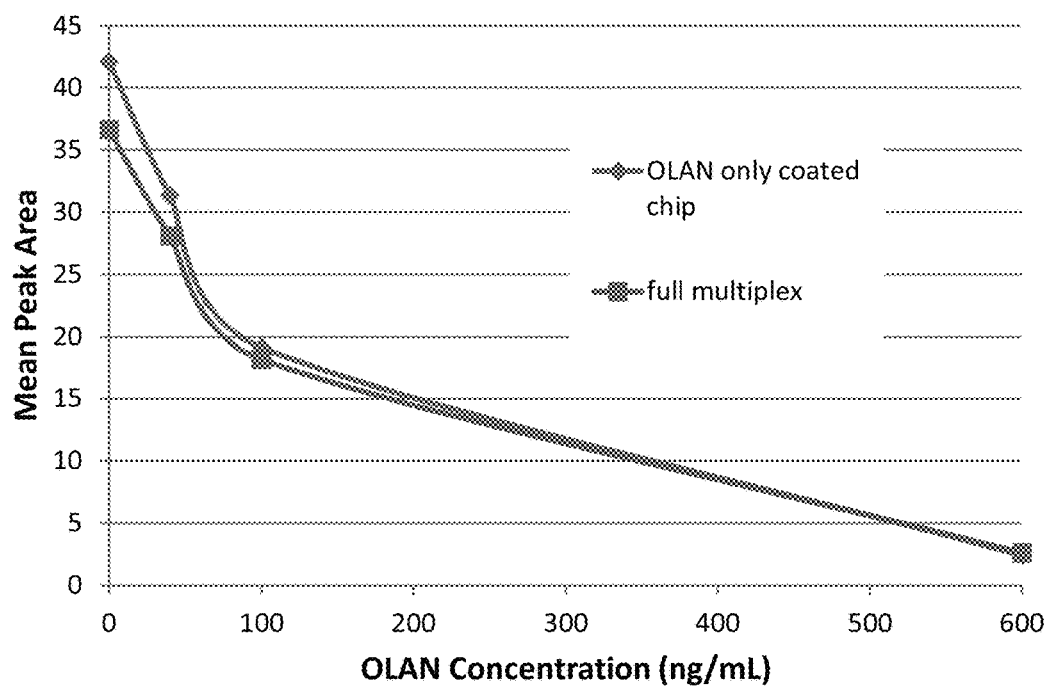
FIG. 18 shows a comparison of the olanzapine dose response curve generated as a positive control to the olanzapine dose response curve generated in the multiplex format.
Figure 19:
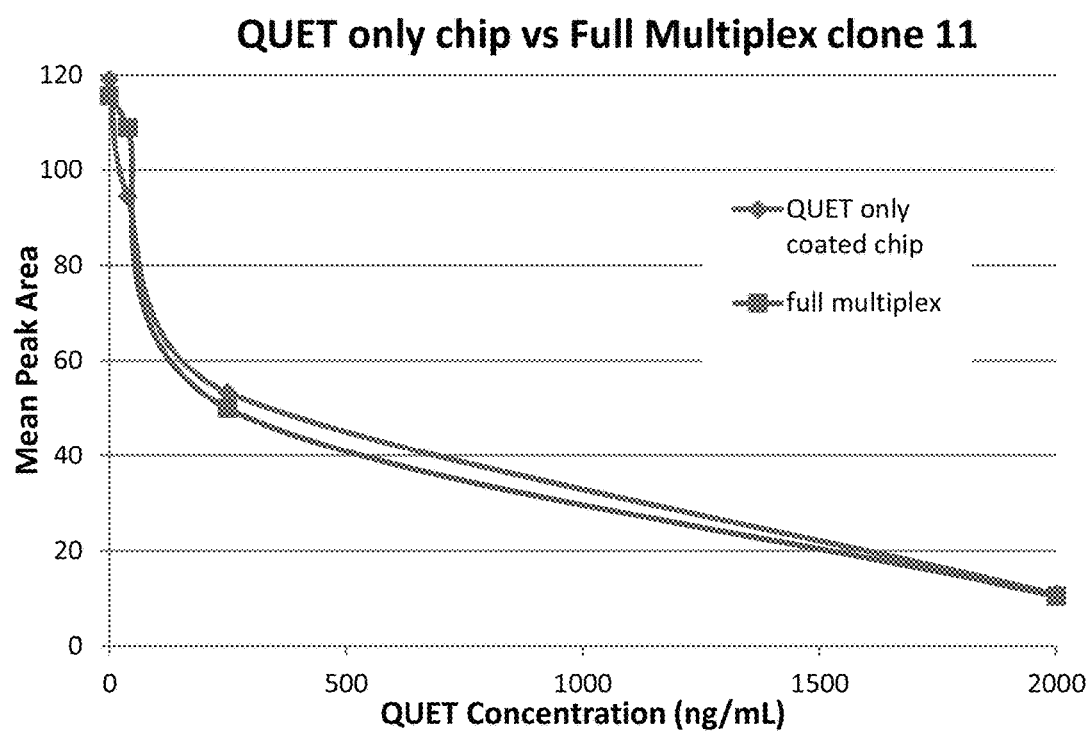
FIG. 19 shows a comparison of the quetiapine dose response curve generated as a positive control to the quetiapine dose response curve generated in the multiplex format.
Figure 20:
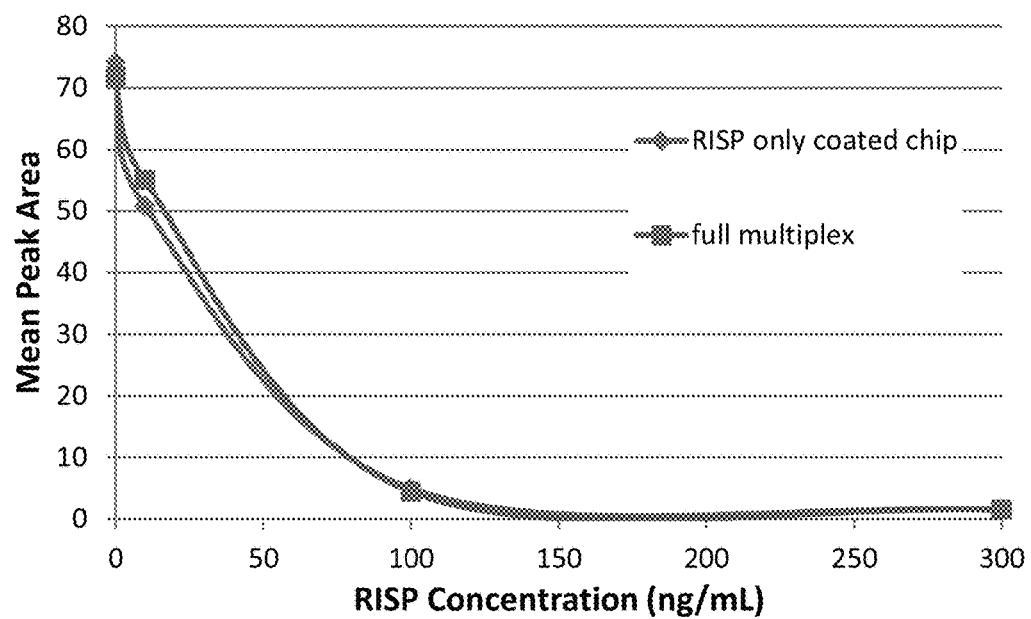
FIG. 20 shows a comparison of the risperidone dose response curve generated as a positive control to the risperidone dose response curve generated in the multiplex format.

FIGS. 17-20 show comparisons of dose response curves generated as positive controls (FIGS. 5-8) to dose response curves generated in the multiplex format (FIGS. 13-16). The comparison for aripiprazole is shown in FIG. 17; for olanzapine in FIG. 18; for quetiapine in FIG. 19; and for risperidone in FIG. 20. These figures show that the positive control curves are similar to the multiplex curves.

These data show that a lateral flow assay device of the subject invention can be used to detect multiple anti-psychotic drugs using a single sample from a patient on one portable, point-of-care device.

What is claimed is:

1. A method of producing an antibody which binds to aripiprazole, the method comprising:
   (i) selecting a host for antibody production; and
   (ii) inoculating the host with a conjugate of a compound of Formula I and an immunogenic carrier, wherein the host produces an antibody which binds to aripiprazole, Formula I wherein:
$R^1$ is H,

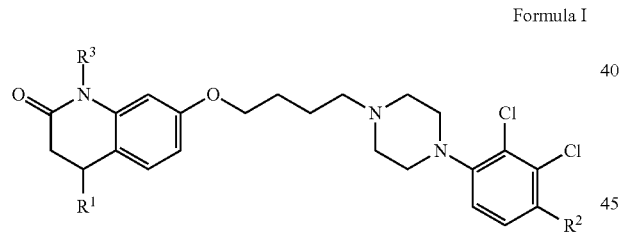

$CH_2NH_2$, or
$CH_2NHC(O)(CH_2)_mCO_2H$;

$R^2$ is H, $NH_2$, or $NHC(O)(CH_2)_mCO_2H$;

$R^3$ is H; provided that either $R^1$ or $R^2$ must be H, and further provided that $R^1$ and $R^2$ may not all be H simultaneously;

m is 1, 2, 3, 4, or 5; and n is 1, 2, 3, 4, or 5.

2. A method of producing a hybridoma cell line capable of producing a monoclonal antibody which binds to aripiprazole, the method comprising:
   (i) selecting a host for antibody production;
   (ii) inoculating the host with a conjugate of a compound of Formula I and an immunogenic carrier;
   (iii) fusing a cell line from said inoculated host with a continuously dividing cell to create a fused cell capable of producing a monoclonal antibody which binds to aripiprazole; and
   (iv) cloning the fused cell so as to obtain a hybridoma cell line, Formula I wherein:
$R^1$ is H, $CH_2NH_2$ or
$CH_2NHC(O)(CH_2)_mCO_2H$;

$R^2$ is H,

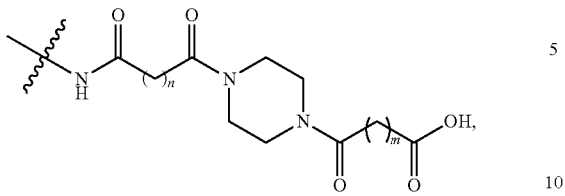

$NH_2$, or $NHC(O)(CH_2)_mCO_2H$;

$R^3$ is H; provided that either $R^1$ or $R^2$ must be H, and further provided that $R^1$ and $R^2$ may not all be H simultaneously;

m is 1, 2, 3, 4, or 5; and n is 1, 2, 3, 4, or 5.

3. The method of claim 1, wherein the immunogenic carrier is a protein.

4. The method of claim 3, wherein the protein is keyhole limpet hemocyanin, bovine thyroglobulin, or ovalbumin.

5. The method of claim 2, wherein the immunogenic carrier is a protein.

6. The method of claim 5, wherein the protein is keyhole limpet hemocyanin, bovine thyroglobulin, or ovalbumin.

7. The method of claim 1, wherein the antibody binding fragment is selected from the group of fragments consisting of Fv, F(ab'), F(ab')2, scFv, minibody and diabody fragments.

8. The method of claim 1, wherein the antibody is a monoclonal antibody.

* * * * *